(12) United States Patent
Iwata et al.

(10) Patent No.: US 6,425,769 B1
(45) Date of Patent: Jul. 30, 2002

(54) TISSUE-DERIVED TUMOR GROWTH INHIBITORS, METHODS OF PREPARATION AND USES THEREOF

(75) Inventors: Kenneth K. Iwata, Westbury; John R. Stephenson, Rockville Centre; Peter ten Dijke, Port Washington, all of NY (US)

(73) Assignee: OSI Pharmaceuticals, Inc., Uniondale, NY (US)

( * ) Notice: Subject to any disclaimer, the term of this patent is extended or adjusted under 35 U.S.C. 154(b) by 0 days.

(21) Appl. No.: 08/457,097

(22) Filed: Jun. 1, 1995

Related U.S. Application Data

(63) Continuation of application No. 08/317,283, filed on Oct. 3, 1994, now abandoned, which is a continuation of application No. 08/110,796, filed on Aug. 23, 1993, now abandoned, which is a continuation of application No. 07/913,744, filed on Jul. 14, 1992, now abandoned, which is a continuation of application No. 07/568,244, filed on Aug. 15, 1990, now abandoned, which is a division of application No. 07/111,022, filed on Oct. 20, 1987, now abandoned, which is a continuation-in-part of application No. 06/922,121, filed on Oct. 20, 1986, now abandoned, which is a continuation-in-part of application No. 06/847,931, filed on Apr. 7, 1986, now abandoned, which is a continuation-in-part of application No. 06/725,003, filed on Apr. 19, 1985, now abandoned.

(51) Int. Cl.[7] .......................... C07H 21/04; C12P 21/06; C12N 5/00; C12N 15/00
(52) U.S. Cl. .................... 439/69.1; 435/70.1; 435/69.7; 435/71.1; 435/71.2; 435/252.3; 435/254.11; 435/257.3; 435/320.1; 435/325; 435/410; 536/23.5; 935/6; 935/13; 935/22; 935/66; 935/109
(58) Field of Search ................................ 435/325, 69.1, 435/69.7, 71.1, 71.2, 70.1, 320.1, 410, 252.3, 254.11, 257.3; 536/23.5; 935/6, 13, 22, 66, 109

(56) References Cited

U.S. PATENT DOCUMENTS

| | | | | |
|---|---|---|---|---|
| 4,886,747 A | * | 12/1989 | Derynck et al. | 435/69.4 |
| 5,104,977 A | | 4/1992 | Sporn | 530/399 |
| 5,168,051 A | * | 12/1992 | Derynck | 435/69.4 |
| 5,284,763 A | * | 2/1994 | Derynck et al. | 435/240.1 |

OTHER PUBLICATIONS

Maniatis et al. in "Molecular Cloning A Laboratory Manual" Chapter 12 pp. 406–433 Cold Spring Harbor Laboratory Press, 1982.*
Massague, J., Cell, (1987) 49:457–458 (Exhibit A).
Sporn, M. B., Science, (1986) 233:532–534 (Exhibit B).

* cited by examiner

Primary Examiner—Patricia A. Duffy
(74) Attorney, Agent, or Firm—John P. White; Cooper & Dunham LLP

(57) ABSTRACT

The invention provides a recombinant nucleic acid vector comprising a nucleic acid encoding a polypeptide of 112 amino acids having the amino acid sequence shown in FIG. 29 beginning with alanine at position 1 and ending with serine at position 112. The sequence of FIG. 29 represents a member of the TGF-β family of tumor growth factors. The invention also provides a method for producing a protein which comprises culturing the host cell under conditions suitable to express the protein in the host cell and recovering the protein so produced.

21 Claims, 43 Drawing Sheets

TGF-β cDNA

*FIGURE 27*

| | | | | | | | | | | | | | | | | |
|---|---|---|---|---|---|---|---|---|---|---|---|---|---|---|---|---|
| | S | T | E | K | N | C | C | V | R | Q | L | Y | I | D | F |
| TGF-B1 | TCC | ACG | GAG | AAG | AAC | TGC | TGC | GTG | CGG | CAG | CTG | TAC | ATT | GAC | TTC |
| (A) | AAC | TTG | GAG | GAG | AAC | TGC | TGT | GTG | CGC | CCC | CTC | TAC | ATT | GAC | TTC |
| | N | L | E | E | N | C | C | V | R | P | L | Y | I | D | F |

| | | | | | | | | | | | | | | | | | |
|---|---|---|---|---|---|---|---|---|---|---|---|---|---|---|---|---|---|
| | R | K | D | L | G | W | K | W | I | H | E | P | K | G | Y |
| TGF-B1 | CGC | AAG | GAC | CTC | GGC | TGG | AAG | TGG | ATC | CAC | GAG | CCC | AAG | GGC | TAC |
| (A) | CGA | CAG | GAT | CTG | GGC | TGG | AAG | TGG | GTC | CAT | GAA | CCT | AAG | GGC | TAC |
| | R | Q | D | L | G | W | K | W | V | H | E | P | K | G | Y |

| | | | | | | | | | | | |
|---|---|---|---|---|---|---|---|---|---|---|---|
| | H | A | N | F | C | L | G | P | C | P | Y |
| TGF-B1 | CAT | GCC | AAC | TTC | TGC | CTC | GGG | CCC | TGC | CCC | TAC |
| (A) | TAT | GCC | AAC | TTC | TGC | TCA | GGC | CCT | TGC | CCA | TAC |
| | Y | A | N | F | C | S | G | P | C | P | Y |

*(A)= the protein having tumor growth inhibitory activity*

FIGURE 29A

```
-120        -110        -101
---  ---  ---  ---  ---  ---  ---
-100                    -90        -81
---  ---  ---  ---  ---  ---  TGG CTG TTG AGA AGA GAG TCC AAC TTA GGT
                               Trp Leu Leu Arg Arg Glu Ser Asn Leu Gly
-80                     -70                             -61
CTA GAA ATC AGC ATT CAC TGT CCA TGT CAC ACC TTT CAG CCC AAT GGA GAT ATC CTG GAA
Leu Glu Ile Ser Ile His Cys Pro Cys His Thr Phe Gln Pro Asn Gly Asp Ile Leu Glu
-60                     -50                             -41
AAC ATT CAC GAG GTG ATG GAA ATC AAA TTC AAA GGC GTG GAC AAT GAG GAT GAC CAT GGC
Asn Ile His Glu Val Met Glu Ile Lys Phe Lys Gly Val Asp Asn Glu Asp Asp His Gly
-40                     -30                             -21
CGT GGA GAT CTG GGG CGC CTC AAG CAG AAG CAG GAT CAC CAC AAC CCT CAT CTA ATC CTC
Arg Gly Asp Leu Gly Arg Leu Lys Lys Lys Gln Asp His His Asn Pro His Leu Ile Leu
-20                     -10                             -1
ATG ATG ATT CCC CCA CAC CGG CTC GAC AAC CCG GGC CAG GGG GGT CAG AGG AAG AAG CGG
Met Met Ile Pro Pro His Arg Leu Asp Asn Pro Gly Gln Gly Gly Gln Arg Lys Lys Arg
```

*FIGURE 29B*

```
                                                                                    10                                              20
(A)    1  GCT TTG GAC ACC AAT TAC TGC TTC CGC AAC TTG GAG GAG AAC TGC TGT GTG CCC CTC
          Ala Leu Asp Thr Asn Tyr Cys Phe Arg Asn Leu Glu Glu Asn Cys Cys Val Arg Pro Leu 30                                              40
(A)   21  TAC ATT GAC TTC CGA CAG GAT CTG GGC AAG TGG GTC CAT GAA CCT AAG GGC TAC TAT
          Tyr Ile Asp Phe Arg Gln Asp Leu Gly Lys Trp Val His Glu Pro Lys Gly Tyr Tyr 50                                              60
(A)   41  GCC AAC TTC TGC TCA GGC CCT TGC CCA TAC CTC CGC AGT GCA GAC ACA CAC AGC ACG
          Ala Asn Phe Cys Ser Gly Pro Cys Pro Tyr Leu Arg Ser Ala Asp Thr His Ser Thr 70                                              80
(A)   61  GTG CTG GGA CTG TAC AAC ACT CTG AAC CCT GAA GCA TCT GCC TCG CCT TGC TGC GTG CCC
          Val Leu Gly Leu Tyr Asn Thr Leu Asn Pro Glu Ala Ser Ala Ser Pro Cys Cys Val Pro 90                                             100
(A)   81  CAG GAC CTG GAG CCC CTG ACC ATC CTG TAC TAT GTT GGG AGG ACC CCC AAA GTG GAG CAG
          Gln Asp Leu Glu Pro Leu Thr Ile Leu Tyr Tyr Val Gly Arg Thr Pro Lys Val Glu Gln 110
(A)  101  CTC TCC AAC ATG GTG GTG AAG TCT TGT AAA TGT AGC tga
          Leu Ser Asn Met Val Val Lys Ser Cys Lys Cys Ser
```

FIGURE 31A

```
                 -120                                                          -110                                                        -101
(A)              ---  ---  ---  ---  ---  ---  ---  ---  ---  ---  ---  ---  ---  ---  ---  ---  ---  ---  ---
TGF-B1           AGG  CTC  AAG  ATT  CAC  GAG  CAG  GTG  GAG  CTG  TAC  CAG  AAA  TAC  AGC  AAC  AAT  TCC
                 Arg  Leu  Lys  Leu  Lys  Val  Glu  Gln  His  Val  Glu  Leu  Tyr  Gln  Lys  Tyr  Ser  Asn  Asn  Ser

-100                                                           -90                                                         -81
(A)              ---  ---  ---  ---  ---  ---  ---  ---  ---  ---  ---  ---  ---  ---  ---  ---  ---  ---  ---
TGF-B1           TGG  CGA  TAC  CTC  AGC  AAC  CGG  AAC  CGG  CTG  GCA  CCC  CTG  TTG  AGA  AGA |GAG  TCC  AAC  TTA  GGT
                 Trp  Arg  Tyr  Leu  Ser  Asn  Arg  Asn  Arg  Leu  Ala  Pro  Leu  Leu  Arg  Arg |Glu  Ser  Met  Leu  Gly

-80                                                            -70                                                         -61
(A)              CTA  GAA  ATC  AGC  ATT  CAC  TGT  CCA  TGT  CAC  ACC  TTT  CAG  CCC  AAT  GGA  GAT  ATC  CTG  GAA
                 Leu  Glu  Ile  Ser  Ile  His  Cys  Pro  Cys  His  Thr  Phe  Gln  Pro  Asn  Gly  Asp  Ile  Leu  Glu
TGF-B1           GAT  GTC  ACC  GGA  CAC  GTG  GTT  GTG  CGG  CTG  TTG  AGC  CGT  GGA  GGG  GAA  ATT  GAG  GGC  TTT  CGC
                 Asp  Val  Thr  Gly  His  Val  Val  Arg  Leu  Leu  Ser  Arg  Gly  Gly  Glu  Ile  Glu  Gly  Phe  Arg

-60                                                            -50                                                         -41
(A)              AAC  ATT  CAC  GAG  GTG  ATG  GAA  ATC  AAA  TTC  AAA  GGT  GTG  GAC  AAT  CAC  AAC  CCT  CAT  CTA  ATC |GGC
                 Asn  Ile  His  Glu  Val  Met  Glu  Ile  Lys  Phe  Lys  Gly  Val  Asp  Asn  His  Asn  Pro  His  Leu  Ile |Gly
TGF-B1           AGC  GCC  CAC  TGC  TCC  TGT  GAC  AGC  AGG  GAT  AAC  ACA  CTG  CAA  GTG  CAT  ATT  CAT  GGC  ATC  TTC |GGG
                 Ser  Ala  His  Cys  Ser  Cys  Asp  Ser  Arg  Asp  Asn  Thr  Leu  Gln  Val  His  Ile  His  Gly  Phe  Arg |Gly

-40                                                            -30                                                         -21
(A)              CGT  GGA  GAT  CTG  GGC |CGC  CTC  AAG  CAG  AAG  CAG |CAC  CAC  AAC  CCT  CAT  CTA  ATC |CTC
                 Arg  Gly  Asp  Leu  Gly |Arg  Leu  Lys  Gln  Lys  Gln |His  His  Asn  Pro  His  Leu  Ile |Leu
TGF-B1           TTC  ACT  ACC  AGC  GGC |CGA  CGG  AGC  AGG  GAT  GAC |CAT  CAT  GGC  ATG  ATC  TTC  CTG |CTG
                 Phe  Thr  Thr  Ser  Gly |Arg  Arg  Ser  Arg  Asp  Asp |His  His  Gly  Met  Ile  Phe  Leu |Leu
```

FIGURE 31B

```
              -20                                                          -10
(A)    ATG  ATG  ATT  CCC  CCA  CAC  CGG  CTC  GAC  AAC  CTG  GGC  CAG  GGT  CAG  AAG  AAG  CGG   -1
       Met  Met  Ile  Pro  Pro  His  Arg  Leu  Asp  Asn  Leu  Gly  Gln  Gly  Gln  Lys  Lys  Arg
TGF-B1 CTT  CTC  ATG  GCC  ACC  CCG  GAG  CAG  GCC  CAT  CTG  CAG  CAC  CGC  CAC  CGC  CGA
       Leu  Leu  Met  Ala  Thr  Pro  Glu  Gln  Ala  His  Gln  Ala  His  Arg  His  Arg  Arg 20
(A)    GCT  TTG  GAC  ACC  AAT  TAC  TGC  TTC  CGC  AAC  TTG  GAG  AAC  TGC  TGT  GTG  CGC  CCC  CTC
       Ala  Leu  Asp  Thr  Asn  Tyr  Cys  Phe  Arg  Asn  Leu  Glu  Asn  Cys  Cys  Val  Arg  Pro  Leu
TGF-B1 GCC  CTG  GAC  ACC  AAC  TAT  TGC  TTC  TCC  AGC  ACG  GAG  AAG  AAC  TGC  TGT  GTG  CGG  CTG
       Ala  Leu  Asp  Thr  Asn  Tyr  Cys  Phe  Ser  Ser  Thr  Glu  Lys  Asn  Cys  Cys  Val  Arg  Leu
TGF-B2                                                 Ala  Leu  Asp  Tyr  Cys  Phe  Arg  Asn  Val  Gln  Asp  Asn  Cys  Cys  Leu  Arg  Pro  Leu 21                                                     30                                           40
(A)    TAC  ATT  GAC  TTC  TGC  CAG  GAT  CTG  GGC  TGG  AAG  TGG  GTC  CAT  GAA  CCT  AAG  GGC  TAC  TAT
       Tyr  Ile  Asp  Phe  Cys  Gln  Asp  Leu  Gly  Trp  Lys  Trp  Val  His  Glu  Pro  Lys  Gly  Tyr  Tyr
TGF-B1 TAC  ATT  GAC  TTC  CGA  CAG  GAT  CTG  GGC  TGG  AAG  TGG  ATC  CAC  GAG  CCC  AAG  GGC  TAC  CAT
       Tyr  Ile  Asp  Phe  Arg  Gln  Asp  Leu  Gly  Trp  Lys  Trp  Ile  His  Glu  Pro  Lys  Gly  Tyr  His
TGF-B2 Tyr  Ile  Asp  Phe  Lys  Arg  Asp  Leu  Gly  Trp  Lys  Trp  Ile  His  Glu  Pro  Lys  Gly  Tyr  Asn 41                                                     50                                           60
(A)    GCC  AAC  TTC  TGC  TCA  GGC  CCT  TGC  CCA  TAC  CTC  CGC  AGT  GCA  GAC  ACA  CAC  AGC  ACG
       Ala  Asn  Phe  Cys  Ser  Gly  Pro  Cys  Pro  Tyr  Leu  Arg  Ser  Ala  Asp  Thr  His  Ser  Thr
TGF-B1 GCC  AAC  TTC  TGC  CTC  GGG  CCC  TGC  CCC  TAC  ATT  TGG  AGC  CTG  GAC  ACG  CAG  TAC  AAG
       Ala  Asn  Phe  Cys  Leu  Gly  Pro  Cys  Pro  Tyr  Ile  Trp  Ser  Leu  Asp  Thr  Gln  Tyr  Lys
TGF-B2 Ala  Asn  Phe  Cys  Ala  Gly  Gly  Cys  Pro  Tyr   ---  ---  ---  ---  ---  ---  ---  ---  ---
```

FIGURE 31C

```
        61
(A)    GTG CTG GGA CTG TAC AAC ACT CTG AAC CCT GAA GCA TCT GCC TCG CCT TGC TGC GTG CCC
       Val Leu Gly Leu Tyr Asn Thr Leu Asn Pro Glu Ala Ser Ala Ser Pro Cys Cys Val Pro
                                                70                                    80
TGF-B1 GTC CTG GCC CTG TAC AAC CAG CAT AAC CCG GGC GCG TCG GCG CCG TGC TGC GTG CCG
       Val Leu Ala Leu Tyr Asn Gln His Asn Pro Gly Ala Ser Ala Ala Pro Cys Cys Val Pro 81
(A)    CAG GAC CTG GAG CCC CTG ACC ATC CTG TAC TAT GTT GGG AGG ACC CCC AAA GTG GAG CAG
       Gln Asp Leu Glu Pro Leu Thr Ile Leu Tyr Tyr Val Gly Arg Thr Pro Lys Val Glu Gln
                                                90                                   100
TGF-B1 CAG GCG CTG GAG CCG CTG CCC ATC GTG TAC TAC GTG GGC CGC AAG CCC AAG GTG GAG CAG
       Gln Ala Leu Glu Pro Leu Pro Ile Val Tyr Tyr Val Gly Arg Lys Pro Lys Val Glu Gln 101
(A)    CTC TCC AAC ATG GTG GTG AAG TCT TGT AAA TGT AGC tga
       Leu Ser Asn Met Val Val Lys Ser Cys Lys Cys Ser
                                        110
TGF-B1 CTG TCC AAC ATG ATC GTG CGC TCC TGC AAG TGC AGC tga
       Leu Ser Asn Met Ile Val Arg Ser Cys Lys Cys Ser
```

(A) The gene encoding the protein having tumor growth inhibitory activity.
TGF-B1 Human TGF-beta type I (Sequence from Derynck et al. (1985) Nature 316)
TGF-B2 Porcine TGF-beta type II
--- Amino acid sequence to be determined (A) = the protein having tumor growth inhibitory activity.

(A) = the protein having tumor growth inhibitory activity.

FIGURE 39
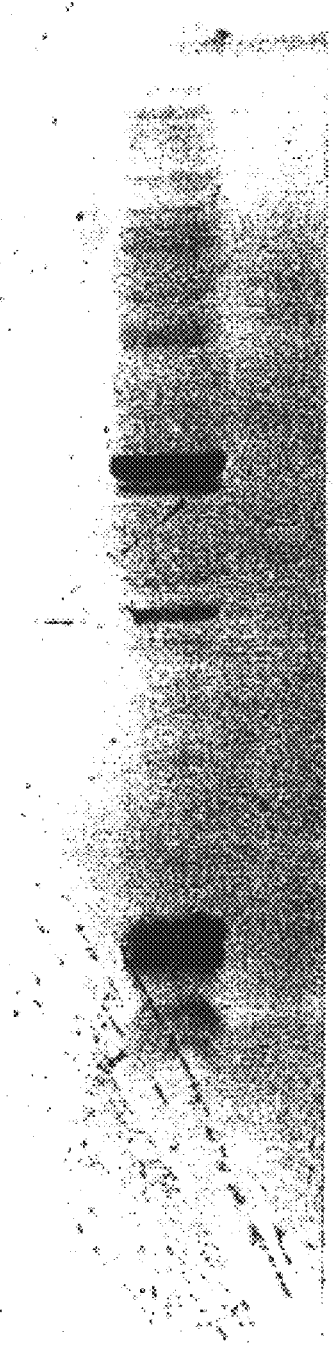
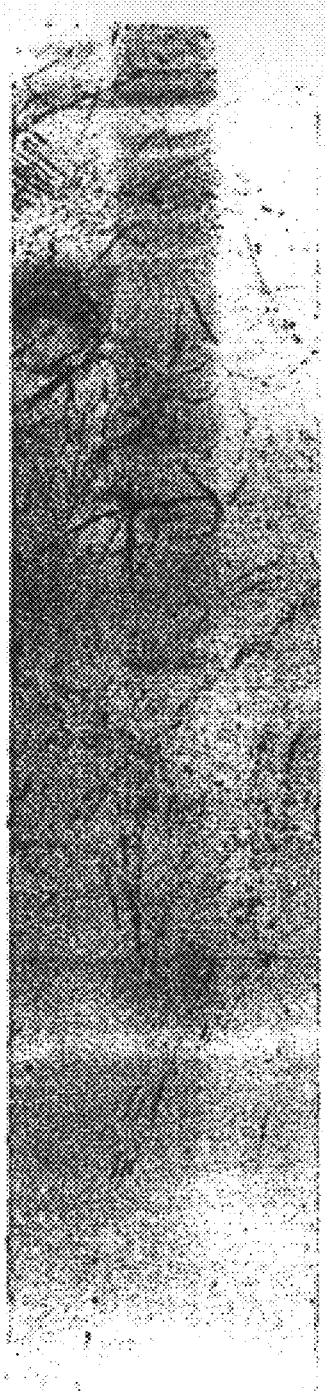

TISSUE-DERIVED TUMOR GROWTH INHIBITORS, METHODS OF PREPARATION AND USES THEREOF

This application is a continuation of U.S. Ser. No. 08/317,283, filed Oct. 3, 1994 now abandoned, which was a continuation of U.S. Ser. No. 08/110,796, filed Aug. 23, 1993, now abandoned, which was a continuation of U.S. Ser. No. 07/913,744, filed Jul. 14, 1992, now abandoned, which was a continuation of U.S. Ser. No. 07/568,244, filed Aug. 15, 1990, now abandoned, which was a divisional of U.S. Ser. No. 07/111,022, filed Oct. 20, 1987, now abandoned, which was a continuation-in-part of U.S. Ser. No. 06/922,121, filed Oct. 20, 1986, now abandoned, which was a continuation-in-part of U.S. Ser. No. 06/847,931, filed Apr. 7, 1986, now abandoned, which was a continuation-in-part of U.S. Ser. No. 06/725,003, filed Apr. 19, 1985, now abandoned. The contents of all of the above applications are hereby incorporated by reference into the present application.

BACKGROUND OF THE INVENTION

Throughout this application, various publications are referenced. The disclosures of these publications in their entireties are hereby incorporated by reference into this application in order to more fully describe the state of the art as known to those skilled therein as of the date of the invention described and claimed herein.

Bichel [Bichel, Nature 231: 449–450 (1971)] reported that removing most of the tumor from mice bearing ascites tumors at a plateau of tumor growth, was followed by a marked increase in the growth of the remaining tumor cells. Injection of cell-free ascites, obtained from mice bearing fully developed ascites tumors, into mice with growing ascites tumors, resulted in a pronounced inhibition of ascites growth. Bichel, supra, also observed that two surgically joined mice (parabiotic), one mouse with an advanced tumor and the other with an early tumor, resulted in a pronounced inhibition of growth of the early tumor. Based upon these observations, [Bichel, Europ. J. Cancer 6: 291–296 (1970) and Bichel, supra] the existence of a diffusible inhibitory principle which circulated through the peritoneum of parabiotic mice and was present in the cell-free ascites fluid produced by the fully developed ascites tumors was postulated. The nature of this inhibiting principle was not characterized, but it was speculated that the rate of growth of ascites tumors was dependent upon the amount of tumor tissue present in the mouse and that the amount of tumor tissue was determined by the amount inhibitory principle produced.

Substances having tumor growth inhibitory activity have been described. McMahon, et al. [Proc. Natl. Acad. Sci. USA 79, 456–460 (1982)] have purified from rat liver a 26,000 dalton substance which inhibits the proliferation of nonmalignant rat liver cells, but does not inhibit the proliferation of malignant rat liver cells. Other growth inhibitory substances have been identified in cultured chicken spinal cord cells [Kage, et al., Experimental Neurology 58: 347–360 (1970); Harrington, et al., Proc. Natl. Acad. Sci. USA 77: 423–427 (1980) and Steck, et al., J. Cell Biol. 83: 562–575 (1979)].

Holley et al., [Proc. Natl. Acad. Sci. 77; 5989 (1980) and Cell Biol. Int. Reports 7: 525–526 (1983)] reported that a substance isolated from African green monkey BSC-1 cells inhibited the growth of BSC-1 cells, human mammary tumor cells and normal human mammary cells. More recently, biochemical characterization of this inhibitory substance [Tucker, et al., Science 226: 705–707 (1984); Roberts, et al. Proc. Nat. Acad. Sci. 82: 119–123 (1985)] showed it to be identical, or highly related, to a 25,000 dalton two chain human platelet-derived polypeptide designated TGF-$\beta$ [Assoian, et al., J. Biol. Chem 258: 7155–7160 (1983)]. TGF-$\beta$ derived from either human platelets [Sporn and Roberts, international patent number WO 84/01106] or from human placenta [Frolik et al., (1983) PNAS 80 3676–3680; Sporn and Roberts (WO84/01106)] induces anchorage independent colony growth in soft agar of non-neoplastic rat kidney fibroblasts and other cells in the presence of transforming growth factor alpha or epidermal growth factor. More recently, the bifunctional nature of this molecule as a regulator of cellular growth has been confirmed by Roberts et al. [Proc. Natl. Acad. Sci. 82: 119–123 (1985)]. Iwata et al., [J. Cellular Biochem. Suppl. 5: 401 (1982)] previously described a microtiter plate system for assaying growth stimulation and growth inhibition activity. Todaro et al., [Todaro et al., in *Tumor Cell Heterogeneity; Origins and Implications*, Bristol-Myers Cancer Symposia, Volume 4, Owens, A. H., Coffey, D. S., and Baylin, S. B., Eds. (Academic Press, 1982), pp. 205–224)] and Iwata et al., [Fed. Proc. Fed. AM. Soc. Exp. Biol. 42: 1833 (1983)] reported the isolation of tumor inhibitory activity from tissue culture fluids of human tumor cells propagated in culture. The observations described in these reports were preliminary and little detail was provided.

On Apr. 20, 1984, a patent application was filed with the United States Patent and Trademark Office under U.S. Ser. No. 602,520, entitled "Substantially Purified Tumor Growth Inhibitory Factor (TIF)" on which one of us, Keneneth K. Iwata, is named as coinventor. This application concerns the preliminary identification of a not well-defined substance or substances present in, and derived from, human tumor cells propagated in culture. This substance or substances resembles the tumor inhibitory activity previously reported. [Todaro, et al., in *Tumor Cell Heterogeneity; Origins and Implications*, Bristol-Myers Cancer Symposia, Volume 4, Owens, A. H., D. S., and Baylin, S. B., Eds. (Academic Press, 1982), pp. 205–224; Iwata, et al., Fed. Proc. Fed. Am. Soc. Exp. Biol. 42: 1833 (1983).]

Todaro [Todaro, G. J. in *Epigenetic Regulation of Cancer*, Terry Fox Cancer Research Conference (University of British Columbia; Vancouver, B.C., Canada) Abs. 13 (1984)] subsequently reported two factors with tumor cell growth inhibitory properties which were reportedly sequenced and shown to consist of 70 and 90 amino acid residues, respectively. However, Todaro failed to report the source of the factors, their tissue type, the species the factors were derived from or the method of the factor purification.

SUMMARY OF THE INVENTION

The invention concerns an acidified, ethanol extract derived from human tissue which comprises a plurality of acidic proteins, each of which has a molecular weight of about 26,000 daltons, is a dimer composed of two polypeptides each of which has an apparent molecular weight of about 13,000 daltons and is joined to the other one by one or more disulfide bonds. This extract has the property of inhibiting the growth of human tumor cells and of an established mink lung cell line (CCL 64) while stimulating the growth of normal human foreskin fibroblasts. The inhibitory activity against human tumor cell growth is not destroyed upon increasing the temperature of the acidified, ethanol extract to about 100° C. for about 3 minutes or upon adding acetic acid and the inhibitory activity is enhanced when the acidified, ethanol extract is prepared at about 4° C. rather than about 23° C.

This invention also concerns an acidified, ethanol extract derived from human umbilical cord which has been treated to remove substantially all blood, all extracellular soluble components and substantially all intracellular soluble components, which comprises at least two acidic proteins each of which has an apparent molecular weight of about 26,000 daltons and each of which is a dimer composed of two polypeptides having apparent molecular weights of about 13,000 daltons and being joined to each other by disulfide bonds under nonreducing conditions. Each extract has the property of inhibiting the growth of human tumor cells and of an established mink lung cell line (CCL 64) while stimulating the growth of normal human foreskin fibroblasts, the inhibitory activity against human tumor cell growth not being destroyed upon increasing the temperature of the acidified, ethanol extract to about 100° C. for about 3 minutes or upon adding acetic acid until the acidified, ethanol extract is up to about 1.0 molar in acetic acid.

The invention further concerns a method for preparing an acidified, ethanol extract from human tissue, e.g., human umbilical cord or human placenta, the acidified, ethanol extract comprising a plurality of acidic proteins, each of which has a molecular weight of about 26,000 daltons and each of which has the property of inhibiting the growth of human tumor cells and of an established mink lung cell line (CCL 64) while stimulating the growth of normal human foreskin fibro-blasts. The method comprises treating under suitable conditions, the tissue source to produce acid soluble proteins, recovering the solubilized proteins, separately recovering from the solubilized extract proteins having an apparent molecular weight of about 26,000 daltons, assaying the proteins so recovered to identify those which either inhibit the growth of human tumor cells or inhibit the growth of an established mink lung cell line (CCL 64), or enhance the growth of normal human foreskin fibroblasts and recovering an acidified, ethanol extract containing the proteins so identified.

This invention also concerns a method for preparing an acidified, ethanol extract from human umbilical cord, the acidified, ethanol extract comprising tissue-derived growth inhibitor (TGI), a mixture of proteins of apparent molecular weight of about 26,000 daltons, which has the property of inhibiting the growth of human tumor cells and of an established mink lung cell line (CCL 64) while stimulating the growth of normal human foreskin fibroblasts. The method comprises under suitable conditions, removing the tissue, washing the tissue to remove all traces of blood and contaminating proteins, solubilizing and isolating the remaining proteins from the tissue by acidified ethanol extraction to produce solubilized proteins, separately recovering from the solubilized TGI proteins having an apparent molecular weight of about 26,000 daltons, assaying the separately recovered TGI proteins to identify the activity which inhibits the growth of human tumor cells, inhibits the growth of an established mink lung cell line (CCL 64) and enhances the growth of normal human foreskin fibroblasts, and recovering the acidified, ethanol extract containing the TGI so identified.

The invention additionally provides a composition of matter designated tissue-derived growth inhibitor-1 (TGI-1) which comprises a protein which is a dimer composed of two polypeptides each having an apparent molecular weight of about 13,000 daltons and being joined to each other by disulfide bonds. TGI-I has the property of inhibiting the growth of human tumor cells and of an established mink lung cell line (CCL 64) but not the growth of normal human foreskin fibroblasts. TGI-I has an apparent molecular weight of about 26,000 daltons, and is recoverable as a defined activity on hydrophobic interaction chromatography on phenyl-Sepharose after ether-ethanol precipitation at about 1.5M ammonium acetate and 31% ethylene glycol and on high performance liquid chromatography of an acidified, ethanol extract with a separating gradient of acetonitrile on a µBondapack® C18 column containing 0.05% trifluoracetic acid at about 27% acetonitrile and recoverable as a defined activity on high performance liquid chromatography of an acidified, ethanol extract with a separating gradient of 2-propanol containing 0.05% trifluoracetic acid at about 40–41% 2-propanol. The invention additionally provides a method for preparing TGI-1.

The invention also provides a composition of matter designated tissue-derived growth inhibitor (TGI) which comprises at least two proteins and has the property of inhibiting the growth of human tumor cells and of an established mink lung cell line (CCL 64) but not the growth of normal human foreskin fibroblasts, each protein having an apparent molecular weight of about 26,000 daltons. Their composition is recoverable as a defined activity on high performance liquid chromatography of an acidified, ethanol extract with a linear gradient of acetonitrile containing 0.05% trifluoracetic acid at about 28–34% acetonitrile and is resolved as a single peak of defined activity from a cation exchange resin when eluted by a linear NaCl gradient at about 0.6–0.7 M NaCl and is recoverable as a defined activity on high performance liquid chromatography of an acidified, ethanol extract from human umbilical cord with a separating gradient of phenyl-Sepharose.

The invention further provides a composition of matter designated tissue-derived growth inhibitor-2 (TGI-2) which comprises a protein having the property of inhibiting the growth of human tumor cells and of an established mink lung cell line (CCL 64) but not the growth of normal human foreskin fibroblasts and having an apparent molecular weight of about 26,000 daltons. TGI-2 is a dimer composed of two polypeptides each having an apparent molecular weight of about 13,000 daltons and being joined to each other by disulfide bonds. TGI-2 is recoverable as a defined activity on hydrophobic interaction chromatography on a phenyl-Sepharose after ether-ethanol precipitation at about 1.5M ammonium acetate and 31% ethylene glycol and on high performance liquid chromatography of an acidified, ethanol extract with a separating gradient of acetonitrile containing 0.05% trifluorocetic acid at about 28–30% acetonitrile on a C18 column and is recoverable as a defined activity on high performance liquid chromatography of an acidified, ethanol extract with a linear gradient of 2-propanol on a CN column containing 0.05% trifluoracetic acid at about 44% 2-propanol. The invention additionally provides a method for preparing TGI-2.

The invention also provides a polypeptide from conditioned media of A431 cells having an apparent molecular weight less than about 30,000 daltons and having the property of substantially inhibiting the growth of a human tumor cell line (A549) but not of an established mink lung cell line (CCL 64).

Furthermore, the invention provides a polypeptide designated CM-I which has the property of substantially inhibiting the growth of human tumor cells but not the growth of an established mink lung cell line (CCL 64).

This invention also provides a protein having an apparent molecular weight of about 26,000 daltons. The protein is a dimer composed of two polypeptides having an apparent molecular weight of about 13,000 daltons and being joined by disulfide bonds. The protein demonstrates tumor growth inhibitory activity of human tumor cell line (A549) and of an established mink lung cell line (CCL 64). It is acid soluble in 1.0 M acetic acid; and 0.1% trifluoracetic acid and is stable in heat to about 100° C.; and is stable in up to 39% acetonitrile and 45% 2-propanol. The protein may be designated TGI-1 or TGI-2.

This invention also provides a protein having tumor growth inhibitory activity comprising the 112 amino acids shown in FIG. 29 beginning with alanine at position 1 and ending with serine at position 112. Preferably, this protein is a purified protein having 112 amino acids beginning with alanine at position 1 and ending with serine at position 112 as shown in FIG. 29. The protein may also comprise the 205 amino acids shown in FIG. 29 beginning with serine at position −93 and ending with serine at position 112. Thus, this 205 amino acid sequence contains partial precursor sequence of the protein having tumor growth inhibitory activity with the complete sequence of the mature protein.

This invention further provides a nucleic acid molecule encoding the protein having tumor growth inhibitory activity comprising the 112 amino acids shown in FIG. 29 beginning with alanine at position 1 and ending with serine at position 112. The nucleic acid molecule may encode the entire protein shown in FIG. 29 beginning with serine at position −93 and ending with serine at position 112. Alternatively, the nucleic acid molecule may encode only the 112 amino acids found in the functional protein shown in FIG. 29 beginning with alanine at position 1 and ending with serine at position 112. These nucleic acid molecules may be cDNA, genomic DNA, or mRNA.

This invention also provides a plasmid which comprises the nucleic acid molecules of this invention as well as a host vector system comprising the plasmid in a suitable host cell. As one embodiment of this invention, a pUC8 plasmid containing a 1.7 kb EcoRI insert was deposited with the American Type Culture Collection (ATCC), 10801 University Blvd., Manassas, Va., 20110-2209, U.S.A., pursuant to the Budapest Treaty on Dec. 20, 1990 and was accorded ATCC Designation No. 40939. This host vector system comprises any plasmid and vector known in the art which are suitable for producing the proteins of this invention. The suitable host cell may be a bacteria cell or a eucaryotic cell.

This invention further provides a method for producing a protein comprising growing the host vector system of this invention so as to produce the protein in the host and recovering the protein so produced.

Pharmaceutical compositions which comprise effective amounts of one of the extracts, TGI-1, TGI, TGI-2, the protein having tumor growth inhibitory activity, the polypeptide recoverable from conditioned media of A431 cells, or CM-I, and a suitable pharmaceutical carrier are provided, as are methods for inhibiting the growth of human tumor cells by contacting the cells with such compositions. The compositions may also be used to treat burns or in wound healing.

The invention also concerns methods for detecting the presence of tumors which comprise quantitatively determining the amount of TGI-1, TGI or TGI-2, the protein having tumor growth inhibitory activity, the polypeptide recoverable from conditioned media of A431 cells, or CM-I present in a sample from a subject and comparing the amount so determined with the amount present in a sample from a normal subject, the presence of a significantly different amount indicating the presence of a tumor. Further, the invention concerns methods for detecting the presence of tumors which comprise separately quantitatively determining the amount of TGI-1, TGI, TGI-2, the protein having tumor growth inhibitory activity, CM-1 or the polypeptide recoverable from conditioned media of A431 cells, and the amount of transforming growth factor alpha (TGF-alpha) present in a sample from a subject, determining the ratio of the amount of TGI-1, TGI, TGI-2, the protein having tumor growth inhibitory activity, CM-I or the polypeptide recoverable from conditioned media of A431 cells, or of a heterogeneous mixture thereof, present in the sample to the amount of TGF-alpha present, determining the comparable ratio for a sample from a normal subject and comparing the ratio for the subject with the ratio for the normal subject, a significant variation in these ratios indicating the presence of a tumor.

Finally, the invention concerns a method for typing tumors which comprises determining from a sample of a subject with a tumor the presence of one or more of TGI-1, TGI, TGI-2, the protein having tumor growth inhibitory activity, CM-I, or the polypeptide recoverable from condition media of A431 cells in the sample, the presence or absence of a specific combination thereof, or the presence of specific amounts or relative amounts thereof, being indicative of a specific tumor type.

Biologically active fractions 90–100 were pooled and dialyzed against 0.1 M acetic acid. The protein concentration of the pooled fractions was determined by absorbance at $OD_{280}$ The recovered protein was 1.4 mg (see Table 7). The quantity of inhibitory units applied was $1.56 \times 10^6$ in 30.9 mg and the amount recovered was $1.5 \times 10^6$ in 1.4 mg.

Figure 14A:
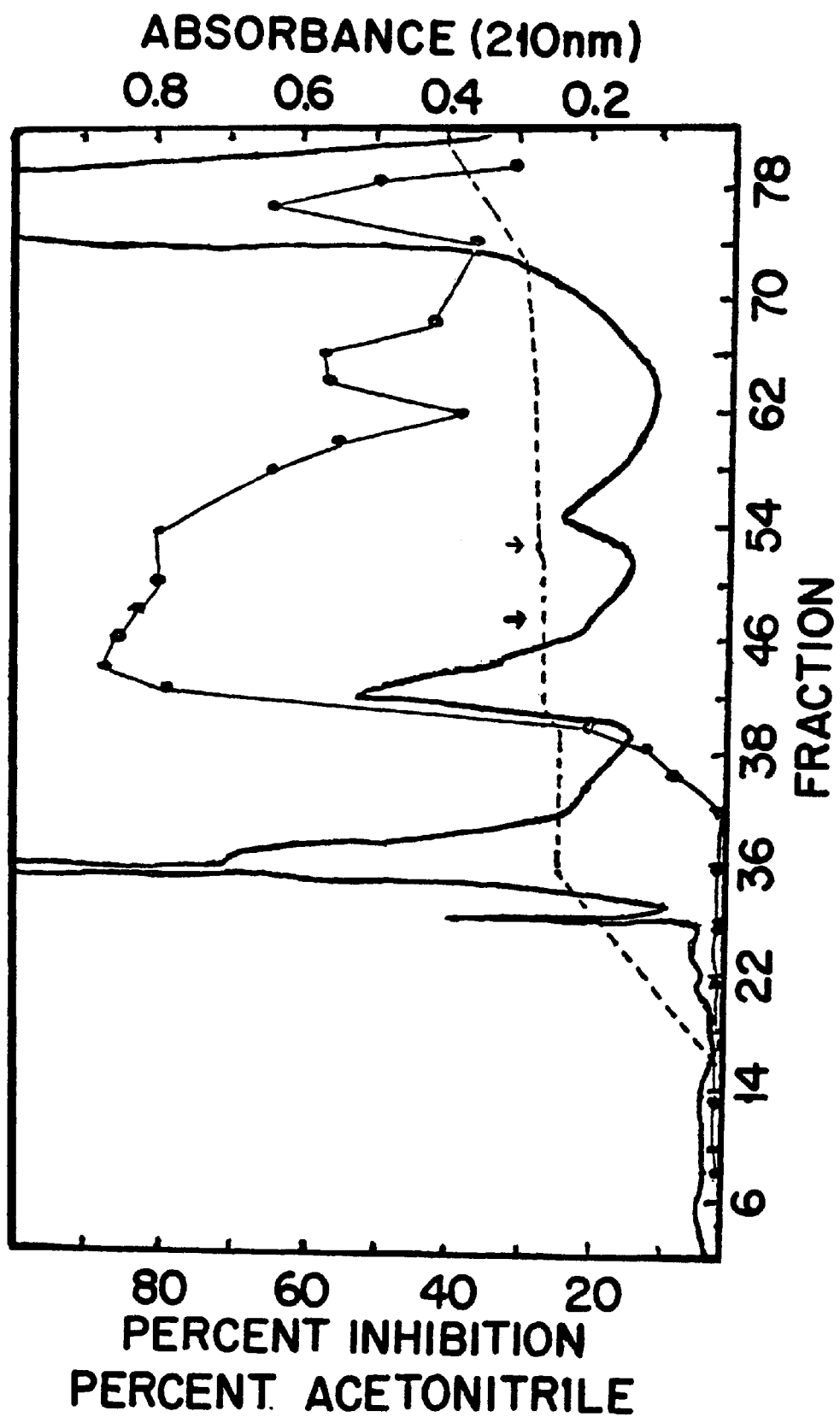

FIG. 14A shows reverse phase high pressure liquid chromatography (HPLC) (μBondpak® C18). One mg of lyophilized TGI derived from the stromal component of umbilical cord tissue (dissected) and obtained from the pooled biologically active fractions resulting from phenyl-Sepharose chromatography, was diluted in 2.0 ml of 0.05% trifluoroacetic acid (TFA) containing 10% acetonitrile. The amount of protein used for RPHPLC at this step represents 50% of the total biologically active proteins obtained following chromatography using phenyl-Sepharose. The protein solution was sonicated for two minutes (Branson B-220 Sonicator) and particulate matter removed by centrifugation (Beckman Model TJ6) at 3,000 rpm for 5 minutes prior to injection into a (μBONDAPAK® C18) column (0.39×30 cm). The protein was eluted at a flow rate of 1.0 ml per minute using a stepwise gradient. The concentration of acetonitrile was initially increased to 25% in fifteen minutes and elution was continued at 25% for 10 minutes; the concentration was then increased to 27% in two minutes and elution was continued at 27% for ten minutes; the concentration increased to 28% in 2 minutes continued at 28% for 10 minutes, and finally the concentration was increased to 100% in 10 minutes. The fractions were collected into siliconized glass tubes. The solvent gradient is illustrated by short dashes. Absorbance of protein was monitored at 210 nm (———). Each fraction volume contained 1.0 ml. The equipment used for RPHPLC was exactly as described in FIG. 12. Five microliter aliquots from every other tube were removed to assess tumor growth inhibitory activity against CCL 64 and A549 as previously described. Activity against the CCL 64 cell line is indicated by closed circles. Fractions 47–51 were pooled separately for electrophoresis by SDS-PAGE (marked by arrows). 350,000 inhibitory units were applied in this chromatographic procedure and the recovered units in the pooled fractions were: 150,000 in fractions 39–58; 14,850 in fractions 59–71 (Total 164,850). The growth inhibitory activity eluted at 27% and 28–30% acetonitrile.

Figure 14B:
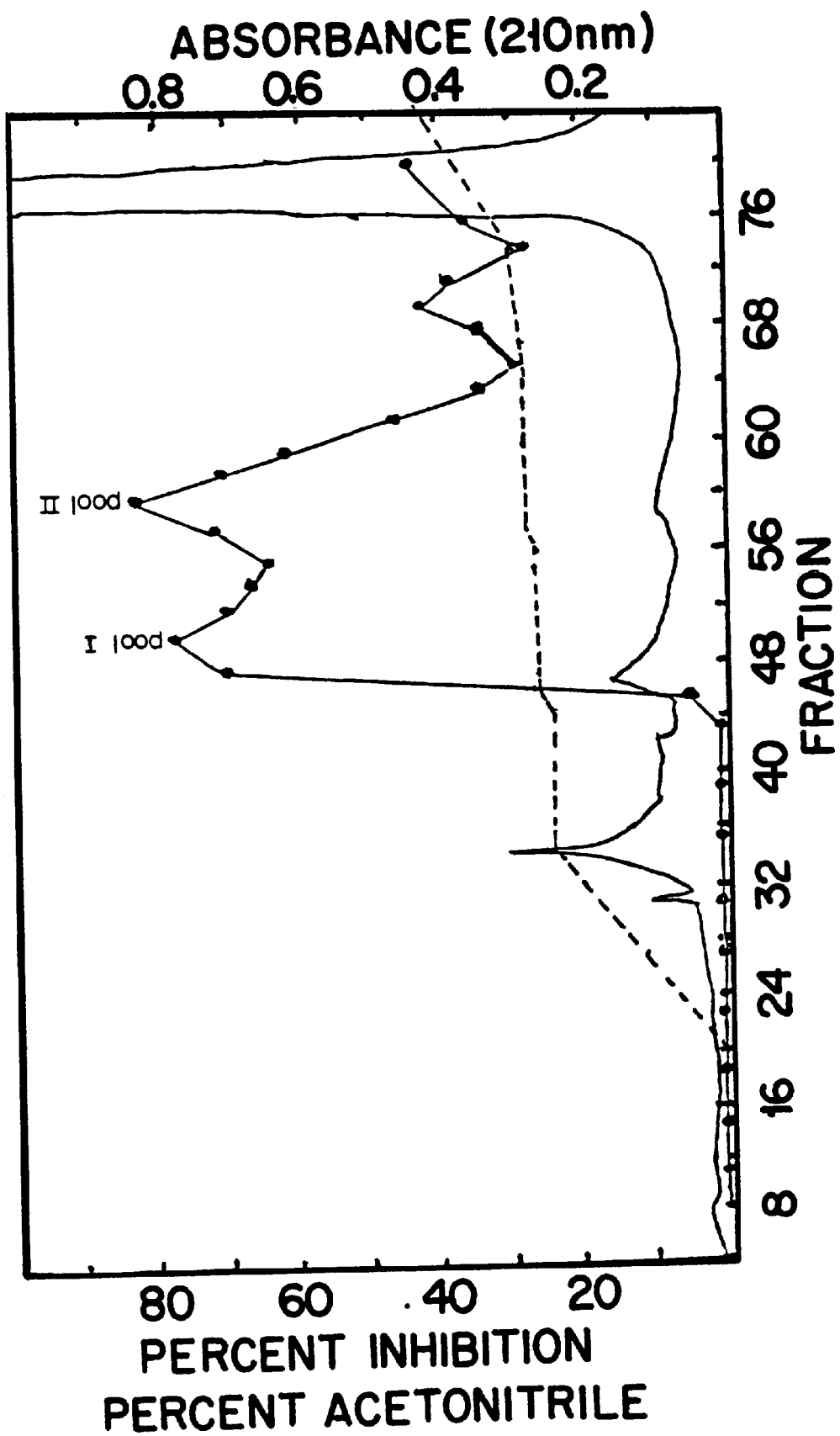

FIG. 14B shows the reverse phase high pressure liquid chromatography (HPLC) (μBONDAPAK® C18). Three hundred and forty-five micrograms of TGI derived from the stromal component of dissected human umbilical cord tissue and obtained from pooled biologically active fractions resulting from phenyl-Sepharose chromatography were diluted in 2.0 ml of 0.05% trifluoracetic acid (TFA) and 10% acetonitrile. The protein was prepared and chromatographed exactly as described in FIG. 14A. Ten microliters from each 1.0 ml sample were used to test for inhibitory activity. This sample represented 30% of the total biologically active pooled fractions derived from phenyl-Sepharose chromatography. The number of inhibitory units applied to the column was 312,500. The recovered units were 62,500 in fractions 46–50, 50,000 units in fraction 51–55, and 90,000 units in fractions 56–72 (Total 202,500 units recovered).

Figure 15:
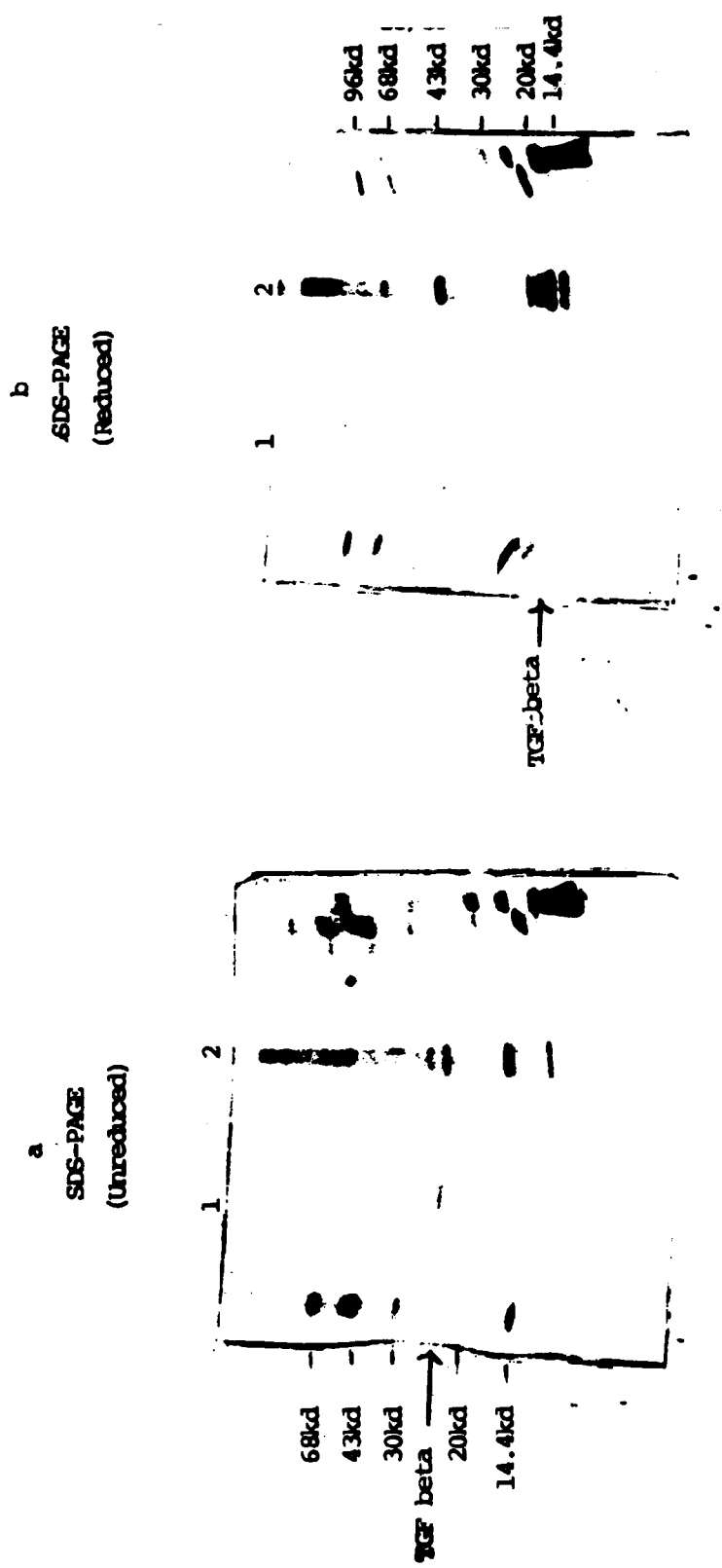

FIG. 15 shows Sodium Dodecyl Sulfate Polyacrylamide Slab Gel Electrophoresis (SDS-PAGE). The lyophilized pool of biologically active protein, as marked by arrows, in FIG. 14A from chromatography by μBONDAPAK® C18 from two identical chromatographic procedures were pooled and prepared for gel electrophoresis. Samples were diluted in 100 microliter sample buffer containing 0.1 M Tris-HCl, pH 6.8 (Sigma), 15% glycerol (Kodak), and 2% sodium dodecyl sulfate (SDS). The samples were boiled for two minutes to remove protein which may have adhered to the glass (siliconized) and 50 microliters transferred to 50 microliters of sample buffer containing 10% β-mercaptoethanol (BioRad®) for reduction of disulfide bonds. These samples were boiled for 2 minutes and both the unreduced and reduced samples were applied to two separate 1.5 mm wide slab gels (marked as lane 2) and electrophoresed through a 10–20% acrylamide gradient in a vertical electrophoresis cell (BioRad, Model 155) under constant current at 30 milliamps (mA) per gel for 4.5 hours (Hoeffer power supply PS 1200 DC). Molecular weight standards (Pharmacia) both reduced by 5% β-mercaptoethanol and non-reduced are marked with their corresponding molecular weights. They are as follows, phosphorylase A, 96 kDa; bovine serum albumin, 68 kDa; ovalbumin, 43 kDa; carbonic anhydrase, 30 kDa: soybean trypsin inhibitor, 21 kDa: and lysozyme 14.4 kDa. Fifty nanograms (50 ng) of a purified platelet derived TGF-β supplied by Dr. Bruce Magun was diluted in sample buffer and electrophoresed under non-reducing conditions (a) and reducing conditions (b) shown in lane 1. The gels were stained with 0.125% coomassie Blue R-250 (BioRad) in 5.7% acetic acid 47% methanol for ten minutes (to fix the protein in the gel), and destained overnight in the same solution without Coomassie Blue. The gels were restained by a silver technique as described by Merril (BioRad silver staining kit #161-0443) Lane 1 (TGF-β) contains approximately 1,000–1,500 (50 ng) units of growth inhibitory activity, and lane 2 contains approximately 8,000–20,000 units of growth inhibitory activity.

Figure 16:
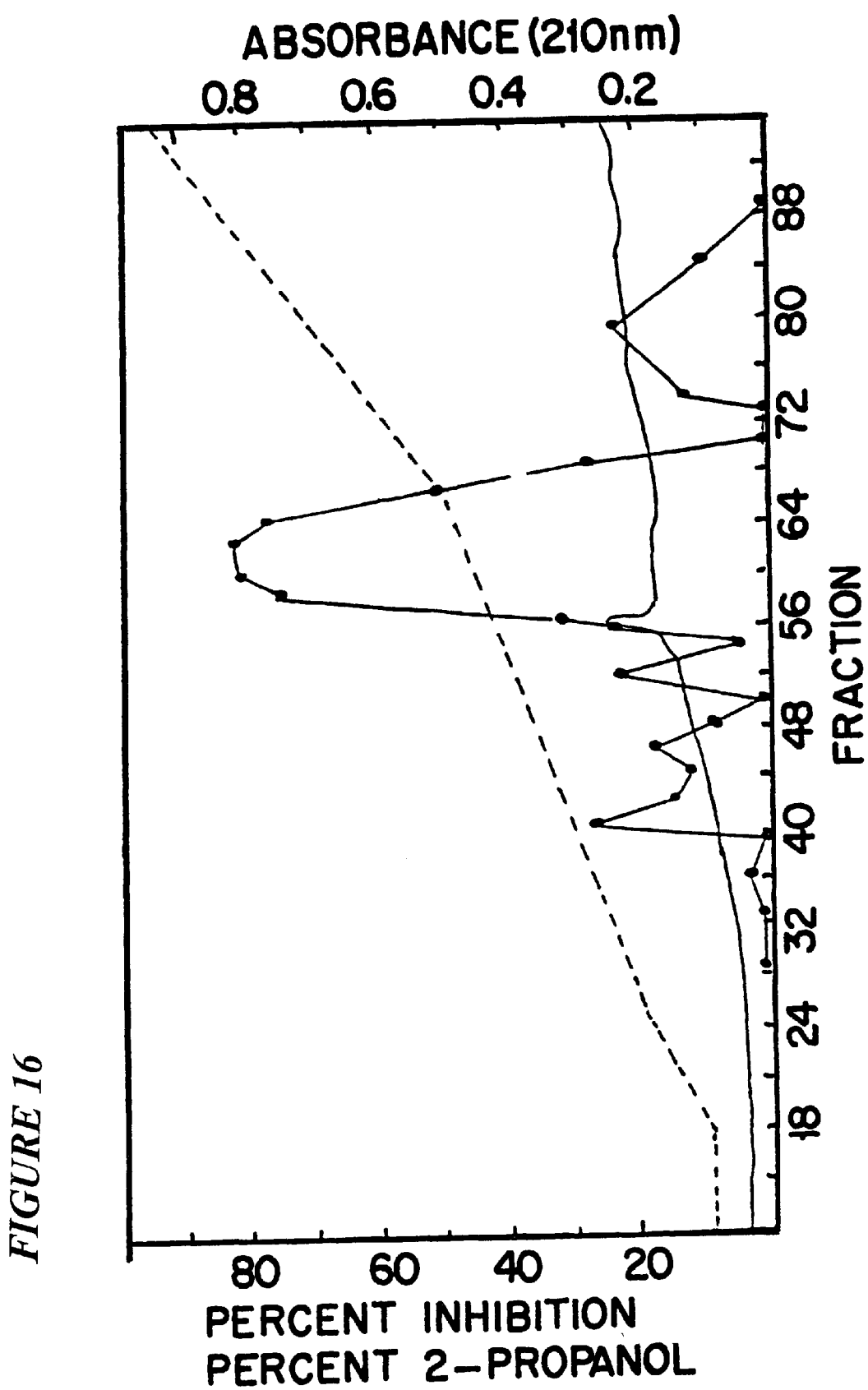
Figure 17:
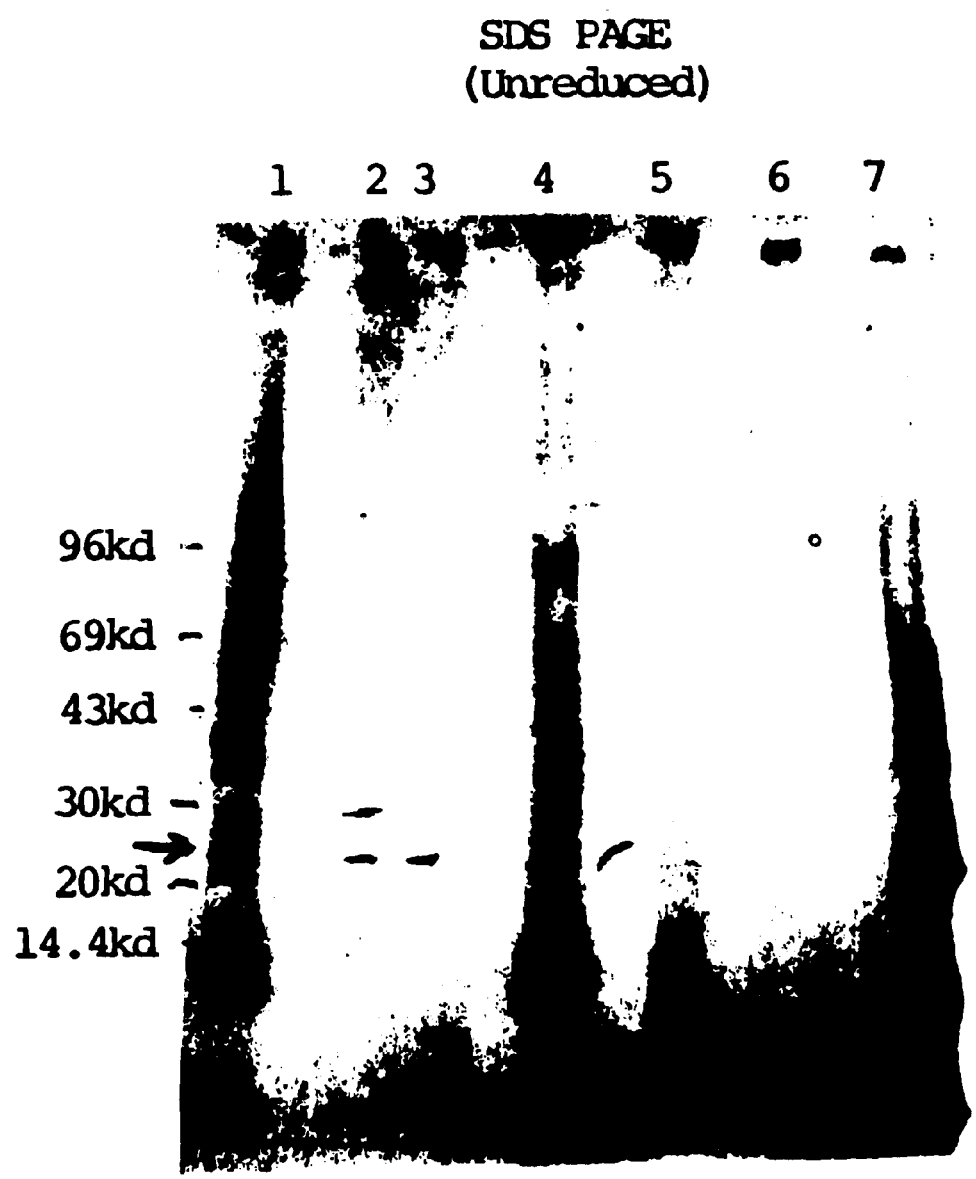

FIG. 16 shows reverse phase high pressure liquid chromatography (HPLC) (μBONDAPAK® CN) of active fractions from the previous HPLC procedure (14B) which were combined from two separate chromatographic runs. The lyophilized material from individual tubes (siliconized glass 13×100 mm tubes) was suspended in 4.0 ml of 0.1% trifluoracetic acid (TFA) containing 10% propanol, sonicated for two minutes and injected onto a μBONDAPAK® CN column (0.39×30 cm) at 1.0 ml/minute. Elution of the protein was achieved by increasing the concentration of 2-propanol containing 0.05% TFA from 10% to 20% in 10 minutes, the concentration was then increased from 20 to 50% in 50 minutes (0.6% per minute), and finally the concentration was increased to 100% in twenty minutes. The solvent gradient is shown as short dashes. Absorbance of the eluted protein was monitored at 210 nm (———————). The equipment used for RPHPLC was exactly as described in FIG. 12. Each fraction volume was 1.0 ml and an aliquot of two hundred microliters was then removed from every other tube to assess biological activity (closed circles). The inhibitory activity eluted from the column between approximately 40–45% 2-propanol. Twelve thousand units (12,000) of activity were applied to this column. The following fractions were lyophilized, iodinated and electrophoresed by SDS-PAGE (FIG. 17). The total number of units contained in these fractions were: Fraction #56 (0 units), #58 (488 units), #59–65 (11,750 units), and #66–68 (185 units).

FIG. 17 shows SDS polyacrylamide slab gel electrophoresis and autoradiography. Lyophilized samples from specific active and inactive fractions from chromatography on a μBONDAPAK® CN column illustrated in FIG. 16 were iodinated as described in the text. Samples were dissolved in both non-reducing and reducing sample buffer as described for FIG. 15 and electrophoresed using a 5–20% acrylamide gradient to resolve protein bands and remove free-radioactive iodine. The gels were stained and destained until the radioactive label disappeared from the destain solution. The gels were dried using a gel dryer (Hoeffer) and subjected to autoradiography using type XAR film (Kodak) for 1 week. Non-radioactive standards were also electrophoresed and are marked at the left of the gel. The number of calculated inhibitory units applied to this gel were: from FIG. 16, fraction #58 (189 units), lane 1; #59–65 (2,068 units), lane 2; #66–68 (46 units), lane 3; #56 (0 units), lane 4; active fraction of undissected human umbilical cord following chromatography on a μBONDAPAK® CN column as described in FIG. 18 chromatogram, (408 units), lane 5; inactive fractions from same stromal/vascular preparation, lane 6; platelet-derived TGF-β purified by Bruce Magun (256 units, approximately 0.4 ng), lane 7.

Figure 18:
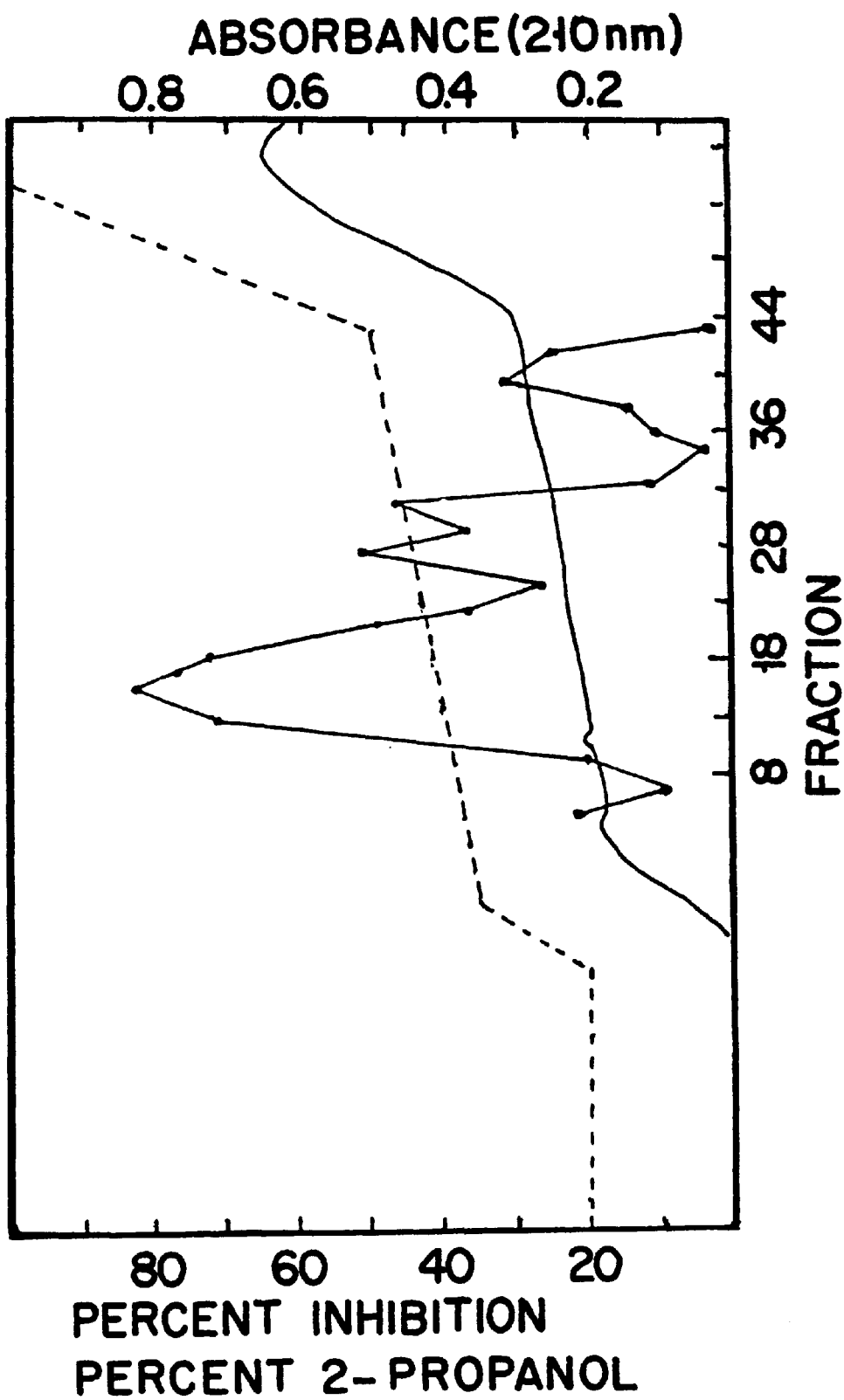

FIG. 18 shows reverse phase high pressure liquid chromatography (HPLC) (μBONDAPAK® CN). Active fractions from a previous HPLC procedure of undissected umbilical cord (similar to FIGS. 14A & 14B), which eluted at 27% acetonitrile (Pool I) from a μBONDAPAK® C18 column were pooled, lyophilized to 1.0 ml volume in a siliconized glass tube (16×100 mm) and diluted to a final concentration of 0.1% trifluoracetic acid (TFA) and 20% 2-propanol. The sample was sonicated for 2 minutes and injected onto a μBONDAPAK® CN column (0.39×30 cm) at 1 ml per minute. Elution of the protein was achieved by increasing the concentration of 2-propanol containing 0.1% TFA from 20% to 35% in 5 minutes followed by 35% to 50% in 50 minutes (0.375% per minute), and 50% to 100% in 5 minutes. The solvent gradient is shown as short dashes. An aliquot of 10 microliters was removed from each 1.0 ml sample to test for biological activity (closed circles). The equipment used for RPHPLC is as described in FIG. 14. The active fractions eluted between 39 to 43% with the peak of activity eluting at 40–41%. The number of calculated inhibitory units applied to the column was 37,000. Protein concentrations could not be determined. Absorbance at 210 nm is shown by the solid line.

Figure 19:
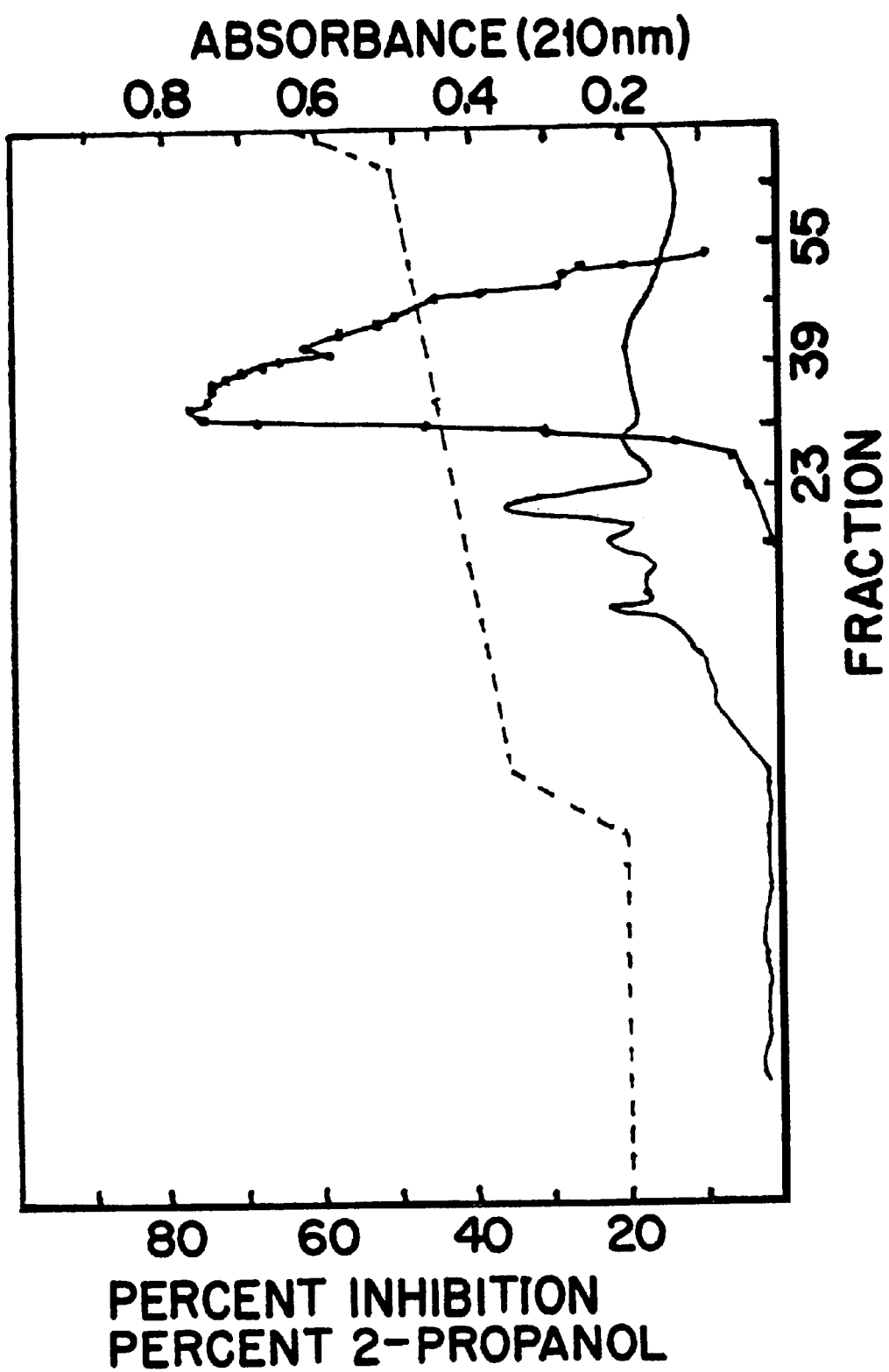

FIG. 19 shows Reverse Phase High Pressure Liquid Chromatography (HPLC) (μBONDAPAK® CN). Active fractions from a previous HPLC procedure (the same chromatographic run as FIG. 18 was derived) which eluted at 28–30% acetonitrile (Pool II) from a C18 resin pooled and applied to a μBONDAPAK® CN column as described in FIG. 18. Gradient elution and equipment are as described for FIG. 18. Aliquots of 100 microliters were removed from every tube to test biological activity (closed circles). Biological activity eluted from 44% to 46% with the peak of activity at 44%. The number of growth inhibitory units applied to the column was 21,000. Protein concentration could not be determined.

Figure 20:
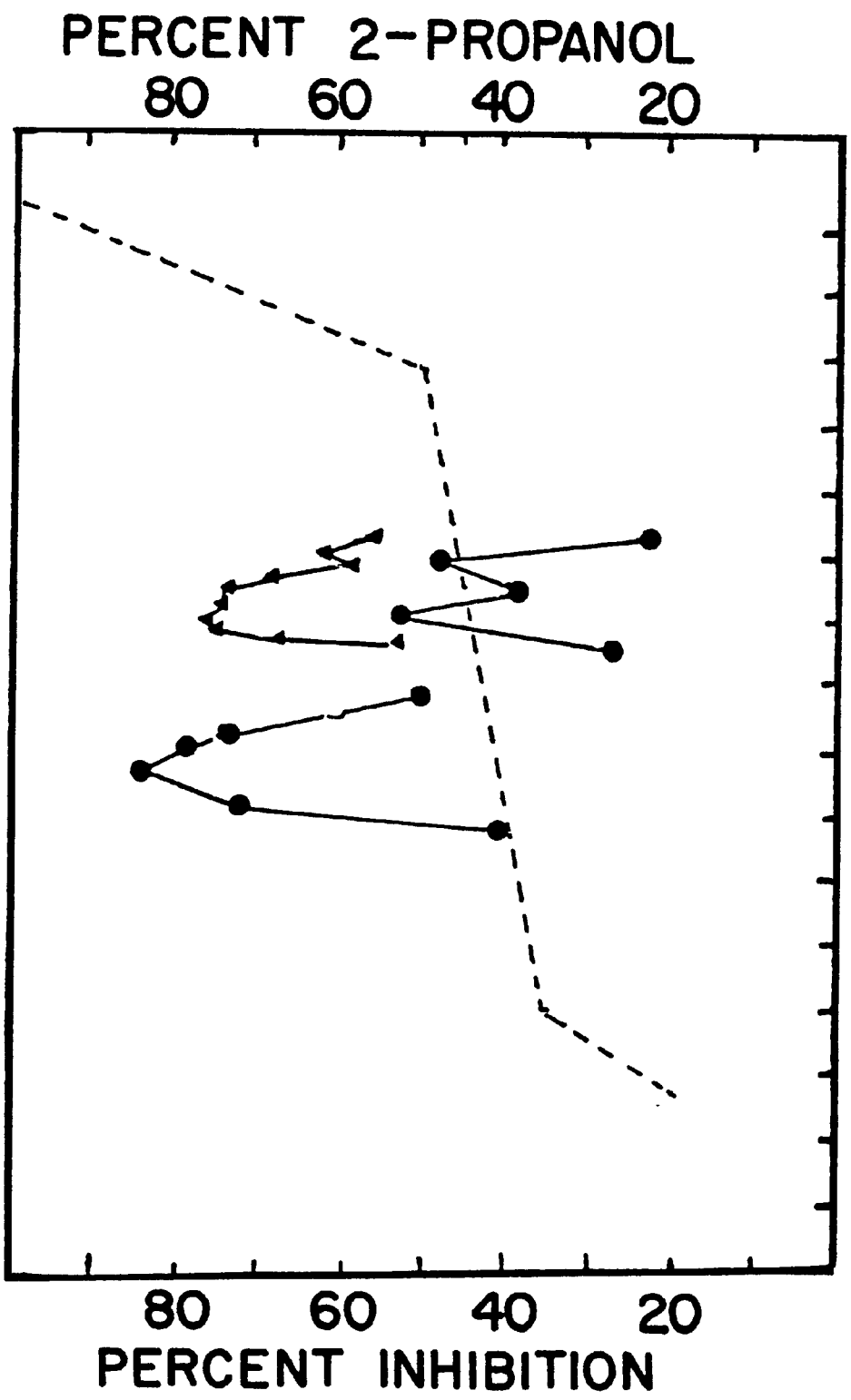

FIG. 20 shows the Reverse Phase High Liquid Chromatography (HPLC) (μBONDAPAK® CN). The elution profiles reflecting biological activity (peaks only) from FIG. 18 (Pool I) and FIG. 19 (Pool II) have been traced onto a separate chromatogram for comparison. Pool I eluted at 40–41% and Pool II at 44%.

Figure 21:
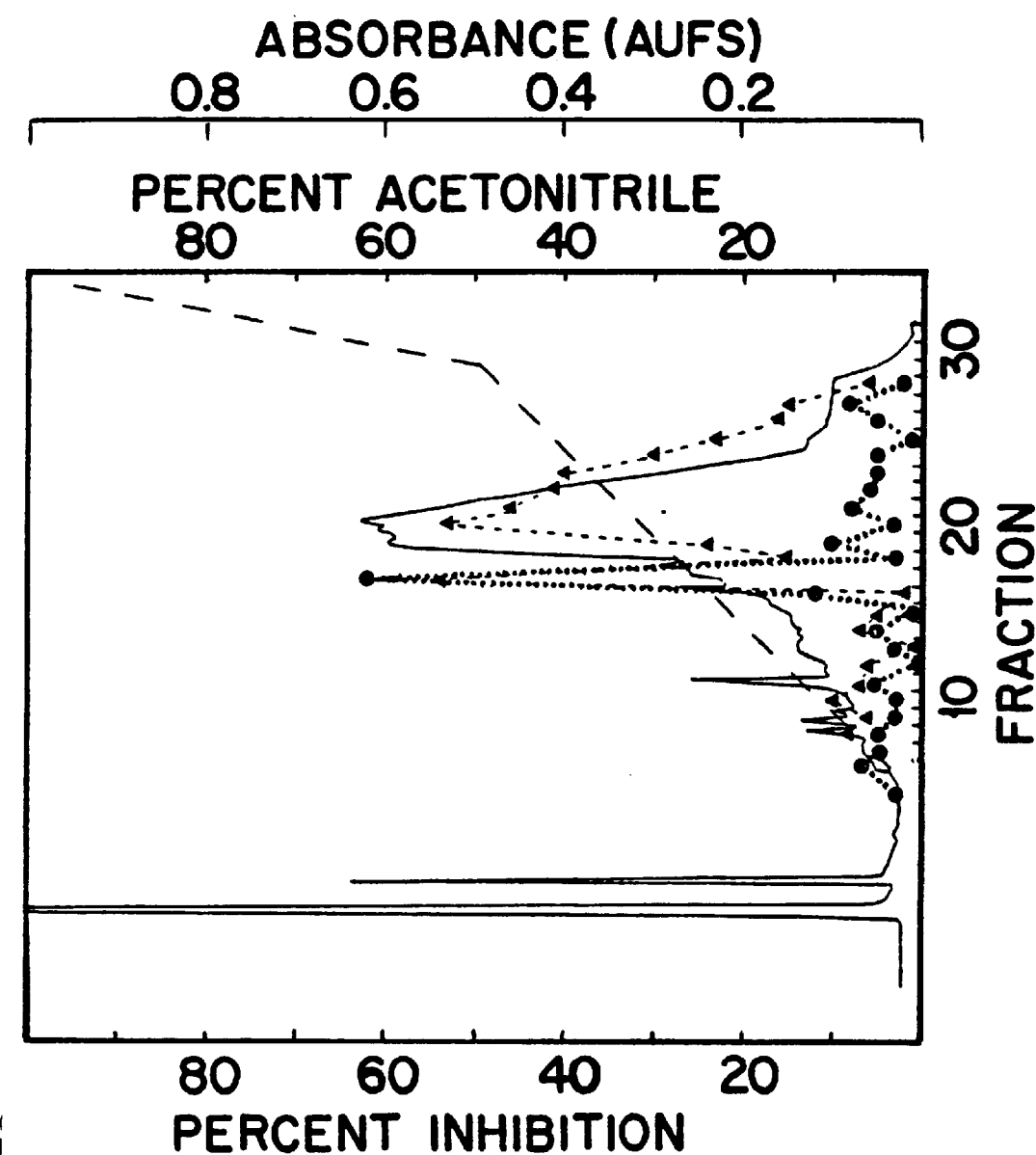

FIG. 21 shows the Reverse Phase HPLC of A431 Conditioned Media. Lyophilized conditioned media from $4 \times 10^8$ A431 cells (110 ml) was processed, as described in the text, for the effect of DTT on tumor growth inhibitory activity derived from tumor cell conditioned media. Lyophilized conditioned media from A431 cells was resuspended in 5 ml 4 mM HCl and centrifuged to remove insoluble material (RC5B-Sorvall® SA600 rotor) for 15 minutes at 3,5000 RPM at 4° C. The supernatant was transferred to 1.5 ml microfuge tubes and centrifuged in an Eppendorf® microfuge for 15 min at 4° C. Protein concentration was determined by absorbance at 280 nm. An aliquot of 0.2 ml containing 680 micrograms protein was added to 1.8 ml 0.1 M ammonium bicarbonate. The samples were incubated at room temperature for 2 hours, lyophilized, and resuspended in 2 ml of 0.05% trifluoroacetic acid. The material (2.0 ml) was injected onto a reverse phase semipreparative μBONDAPAK® C18 column at 1.0 ml/min and 2.0 ml fractions were collected at the start of the linear acetonitrile from 0–50% in 50 min. An aliquot of 1.0 ml gradient from each fraction was assayed for tumor growth inhibitory activity against mink cell line (CCL 64) (—●—●—●—) and human tumor cell line (A549) (−−▲−−▲−−) as previously described. Absorbance at 206 nm is indicated by the solid line.

Figure 22:
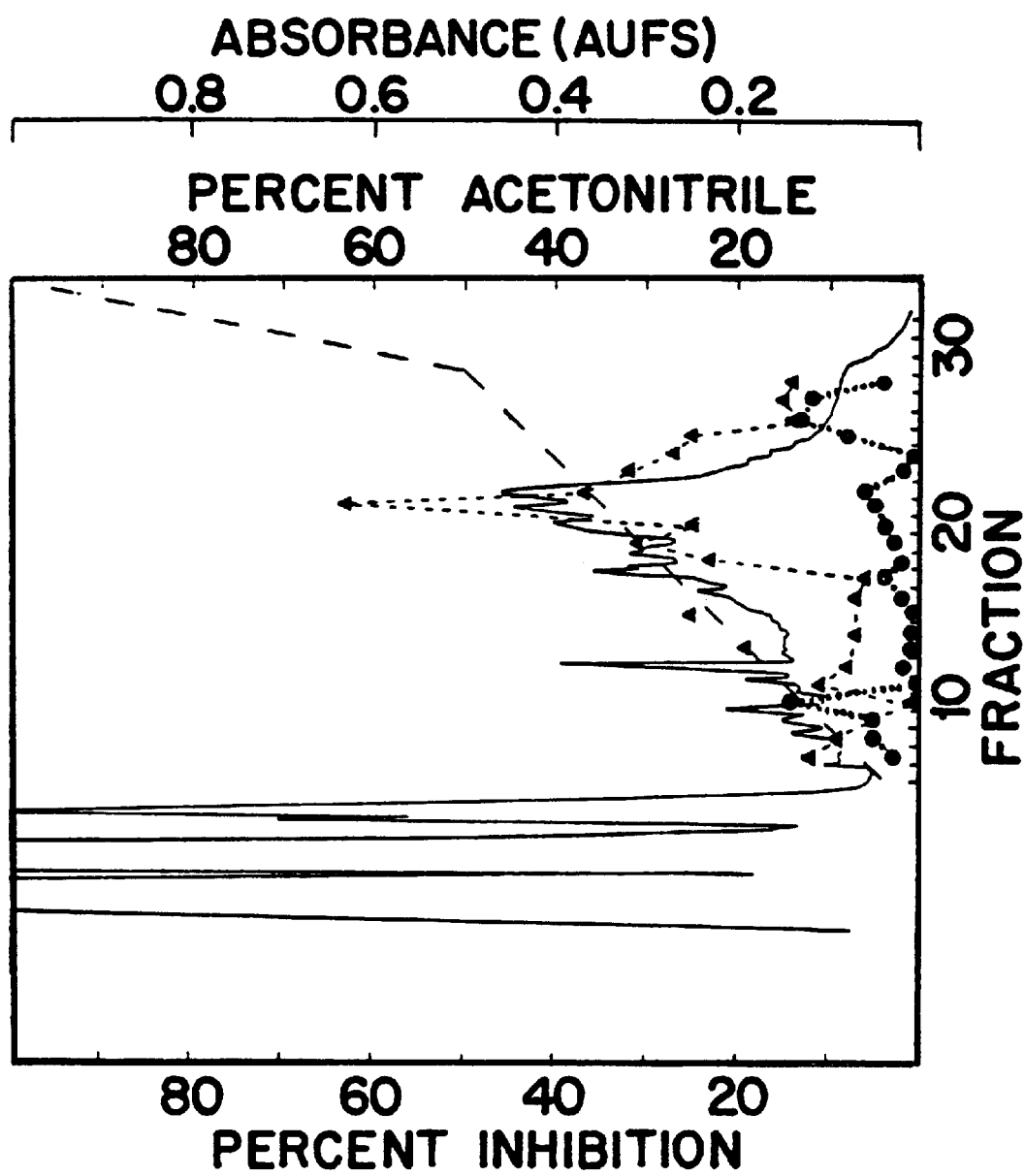

FIG. 22 shows the. Reverse-phase HPLC of A431 Conditioned Media Treated with DTT. Lyophilized conditioned media from $4 \times 10^-$ A431 cells (110 ml) was processed, as previously described, for the effect of DTT on tumor growth inhibitory activity in tumor cell conditioned media. Lyophilized conditioned media from A431 cells was resuspended in 5 ml 4 mM HCl and centrifuged to remove insoluble material (RC5B-Sorvall® SA 600 rotor) for 15 minutes at 3,500 RPM at 4° C. The supernatant was transferred to 1.5 ml microfuge tubes and centrifuged in an Eppendorf® microfuge for 15 min. at 4° C. Protein concentration was determined by absorbance at 280 nm. An aliquot of 0.2 ml containing 680 micrograms protein was added to 1.8 ml 0.1 M ammonium bicarbonate containing a final concentration of 65 mM DTT. The samples were incubated at room temperature for 2 h., 20 lyophilized, and resuspended in 2 ml of 0.05% trifluoroacetic acid. The material (1.0 ml) was injected onto a reverse phase semipreparative μBONDAPAK® C18 column, and 2.0 ml fractions were collected at the start of a linear gradient and assayed for growth inhibitory activity against mink lung cell line (CCL 64) (−−●−−●−−) and human tumor cell line (A549) (−−▲−−▲−−) as previously described. Absorbance at 206 nm is indicated by the solid line.

Figure 23:
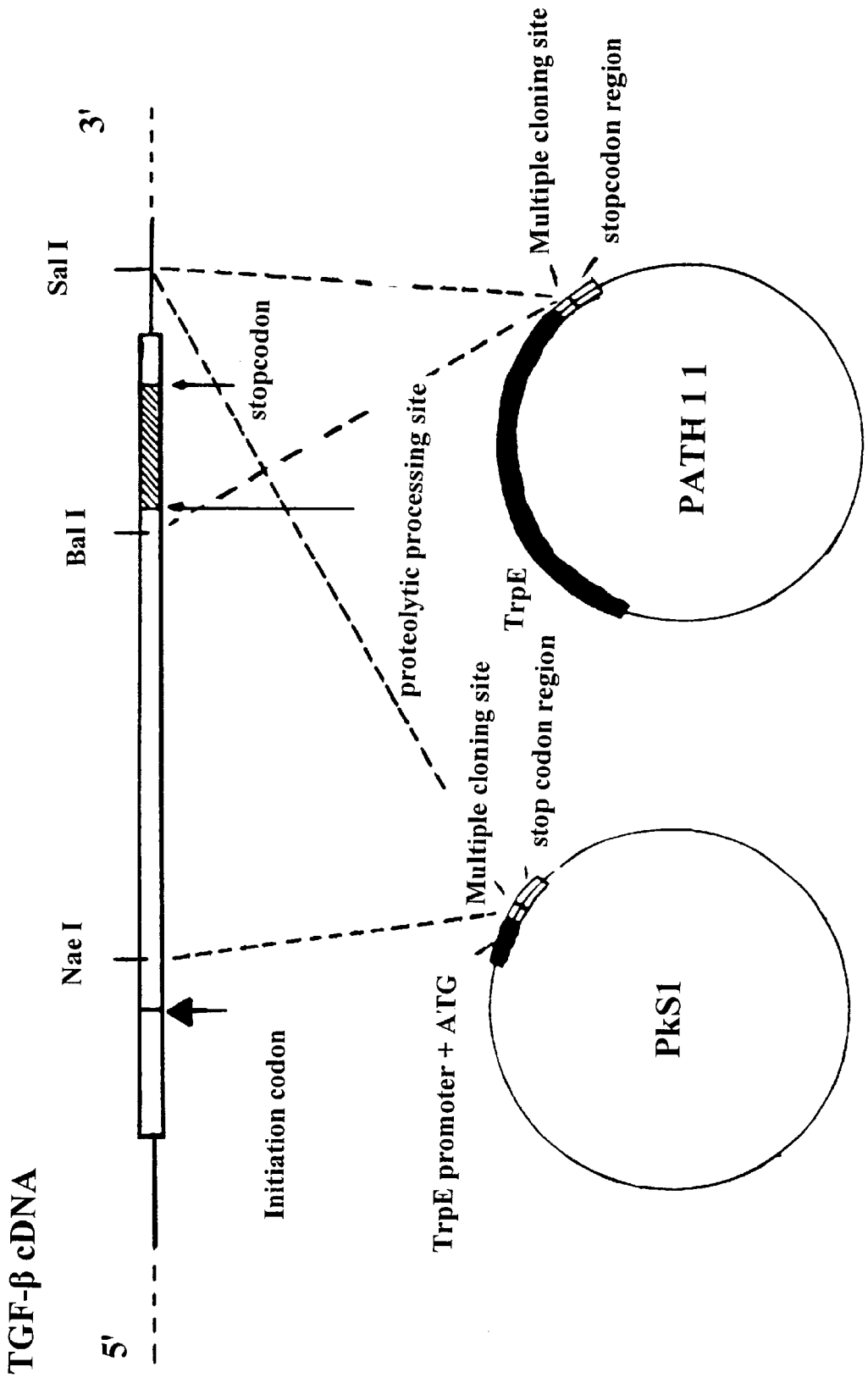

FIG. 23 in a schematic representation of trpE::TGF-β1 plasmid constructs using pATH 11 and pKS-1 expression vectors for the production of TGF-β1 polypeptide in bacteria.

Figure 24:
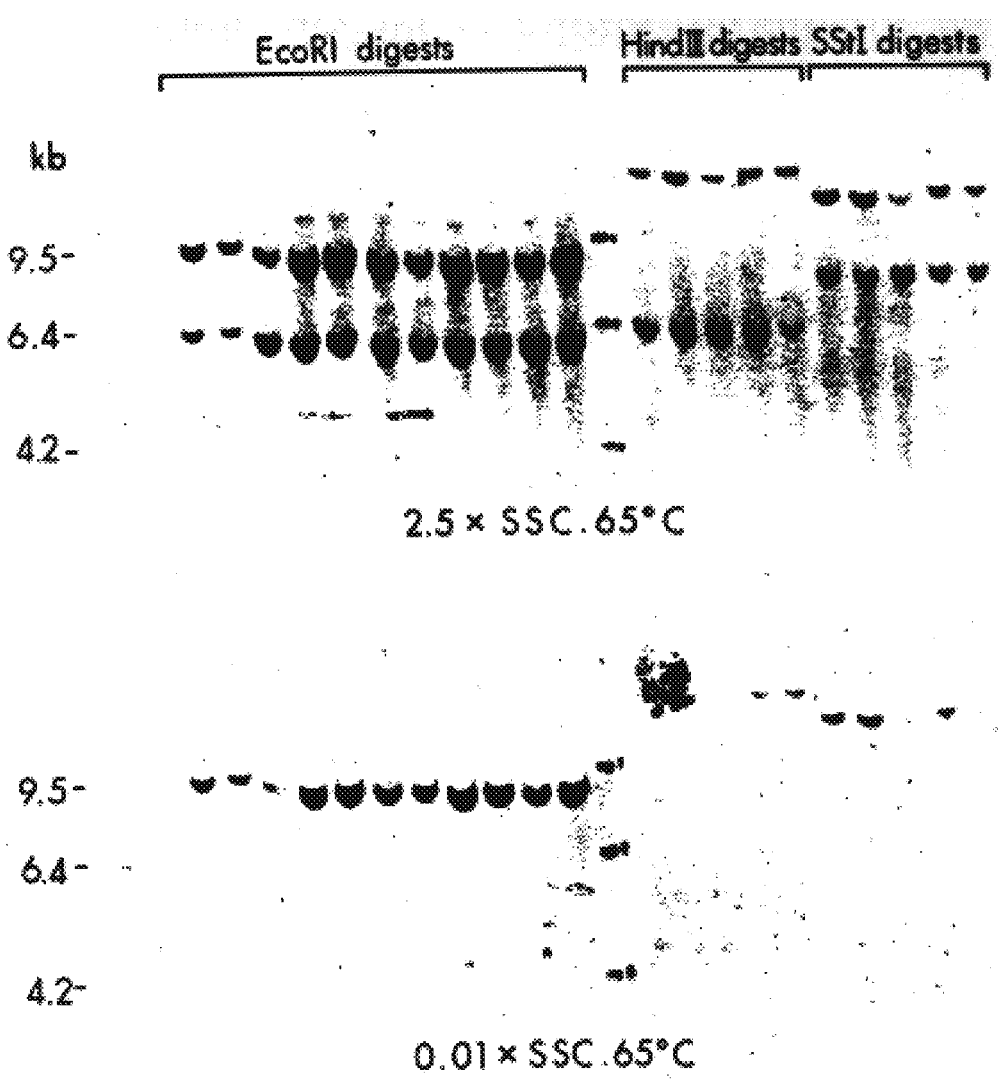

FIG. 24 shows a Southern blot analysis of human tumor DNAs hybridized with a Pvu II-Pvu II TGF-β1 cDNA probe. SCC. is standard saline-citrate buffer, which consists of: 0.15M sodium chloride and 0.15M sodium citrate. (pH 7.0).

Figure 25:
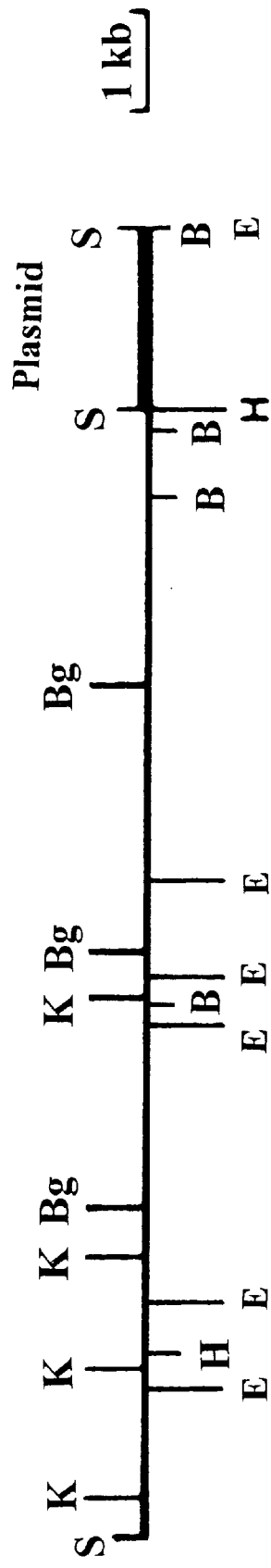

FIG. 25 shows a restriction map of the phage subclone that hybridized to the TGF-β1 cDNA probe at high stringency wash. The clone corresponds to TGF-β1 genomic locus. The Sal I-Sal I fragment of the phage clone was subcloned into pUC. Abbreviations for restriction enzyme sites are: S-Sal I; K-KpnI; E-Eco RI; H-Hind III; B-Bam HI; Bg-Bgl II.

Figure 26:
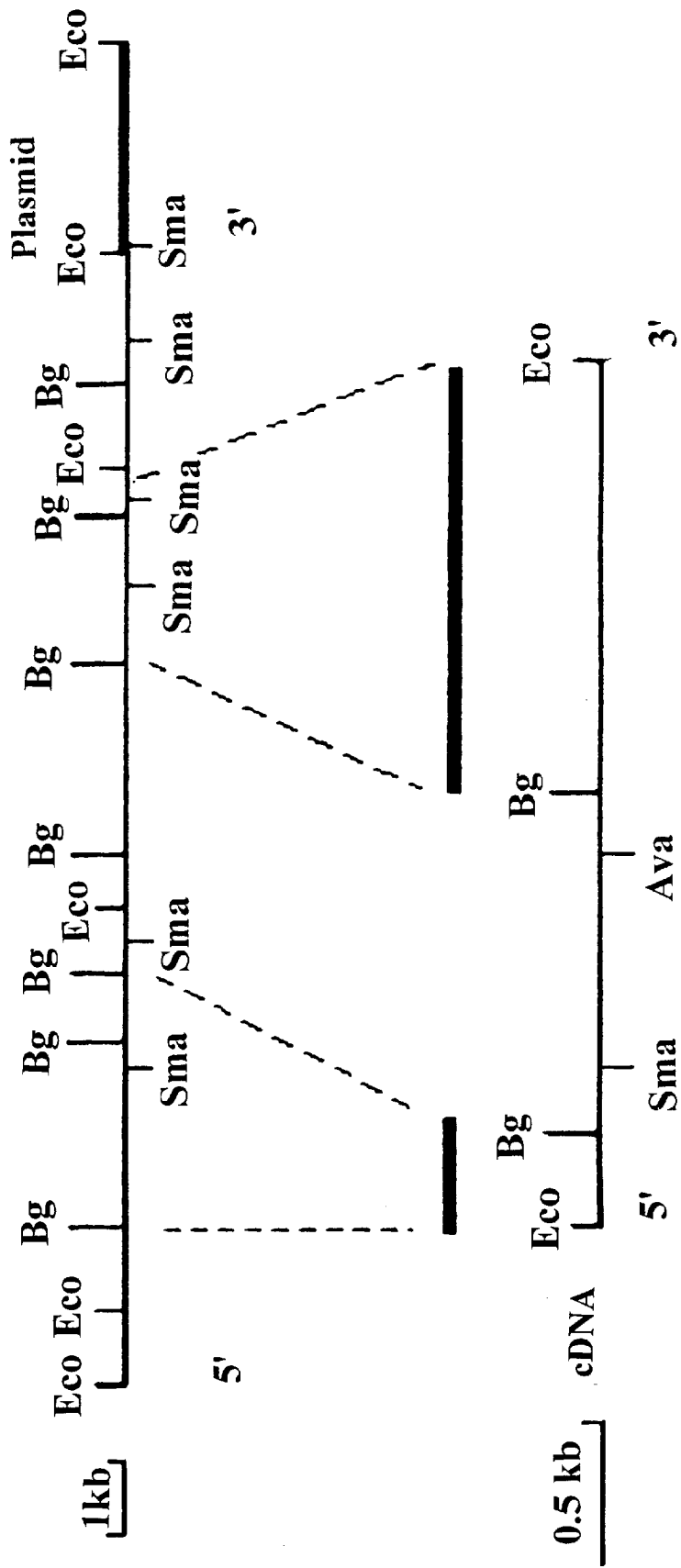

FIG. 26 shows a restriction map of the phage subclone that hybridized to the TGF-β1 cDNA probe only under conditions of low stringency.

FIG. 27 shows a comparison of the nucleotide sequence and the predicted amino acid sequence of TGF-β1 and the related gene encoding the protein with tumor inhibitory activity. Identical amino acids are boxed. (A) corresponds to the gene encoding the protein having tumor growth inhibitory activity.

Figure 28:
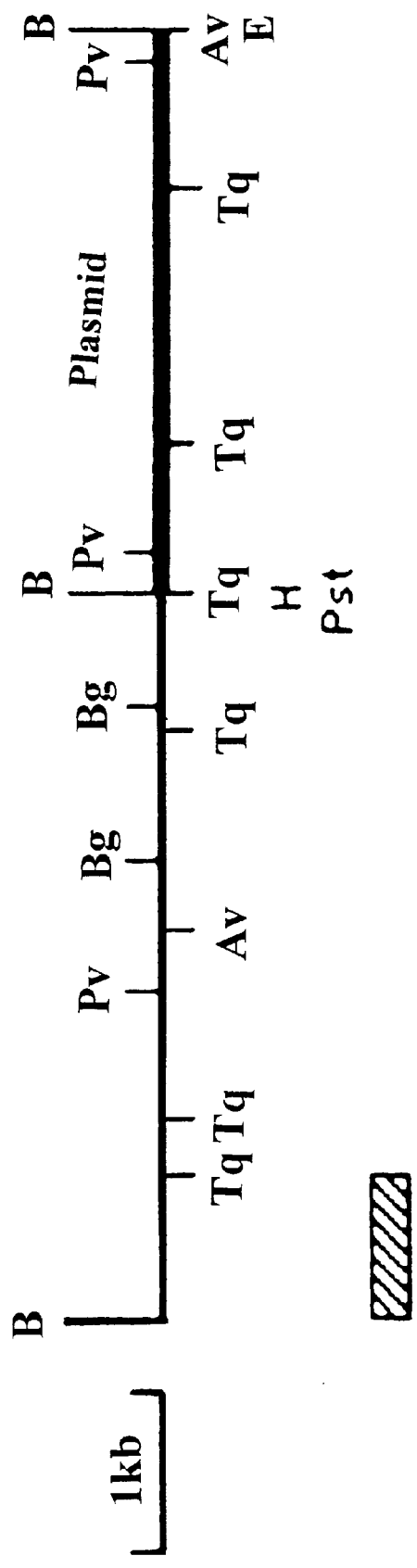

FIG. 28 shows a restriction map of the Bam HI fragment of the related gene encoding the protein having tumor growth inhibitory activity subcloned into pUC. The position of the repeat free fragment (BamHI-TaqI) is indicated with a bar.

FIGS. 29A–29B shows a partial nucleotide sequence of the 1.7 kb CDNA encoding the protein having tumor growth inhibitory activity and its corresponding amino acid sequence.

Figure 30:
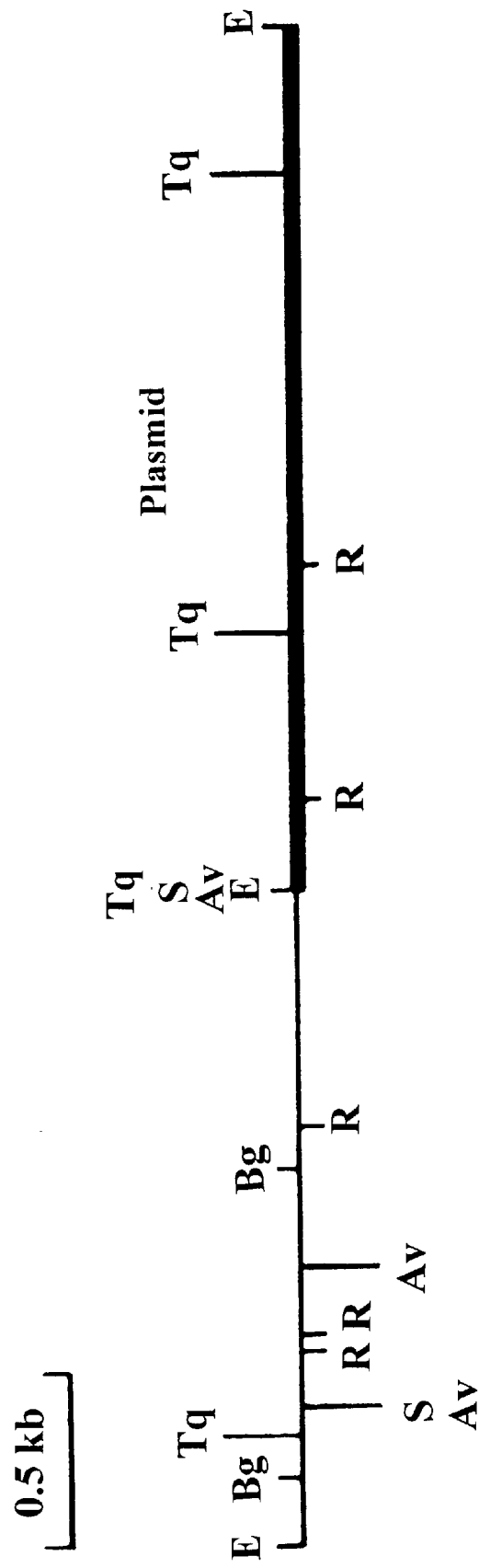

FIG. 30 shows the restriction map of the 1.7 kb Eco RI subclone of the TGF-β1 related gene encoding the protein having tumor growth inhibitory activity.

FIG. 31 shows a nucleotide and predicted amino acid sequence comparison of the gene encoding the protein having tumor growth inhibitory activity with TGF-β1 and TGF-β2. (A) corresponds to the gene encoding the protein having tumor growth inhibitory activity.

Figure 32:
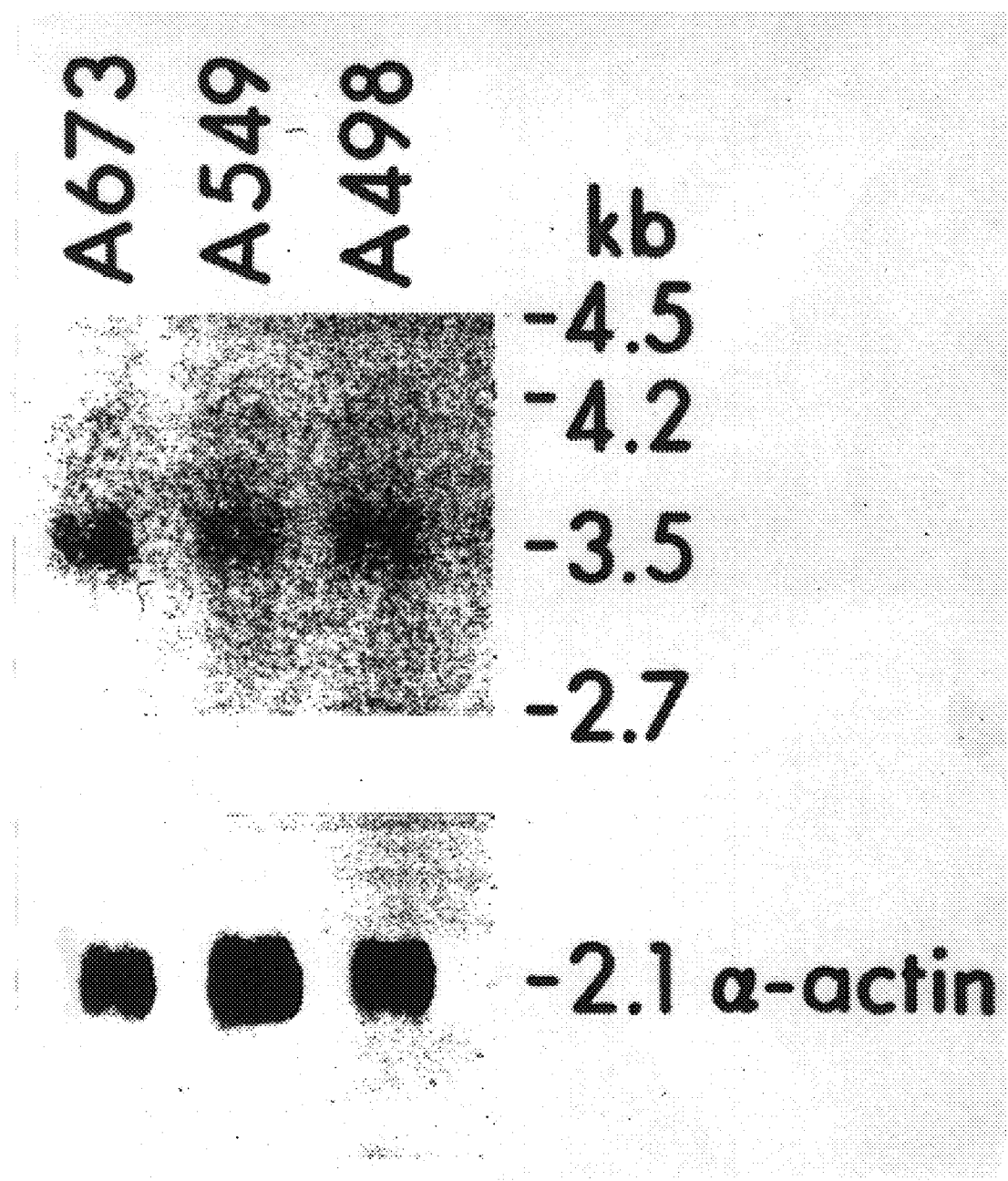

FIG. 32 shows a Northern blot analysis of A673, A549, and A498 cell lines using an Eco RI-Bgl II 1.7 kb cDNA fragment of the gene encoding the protein having tumor growth inhibitory activity as a probe.

Figure 33:
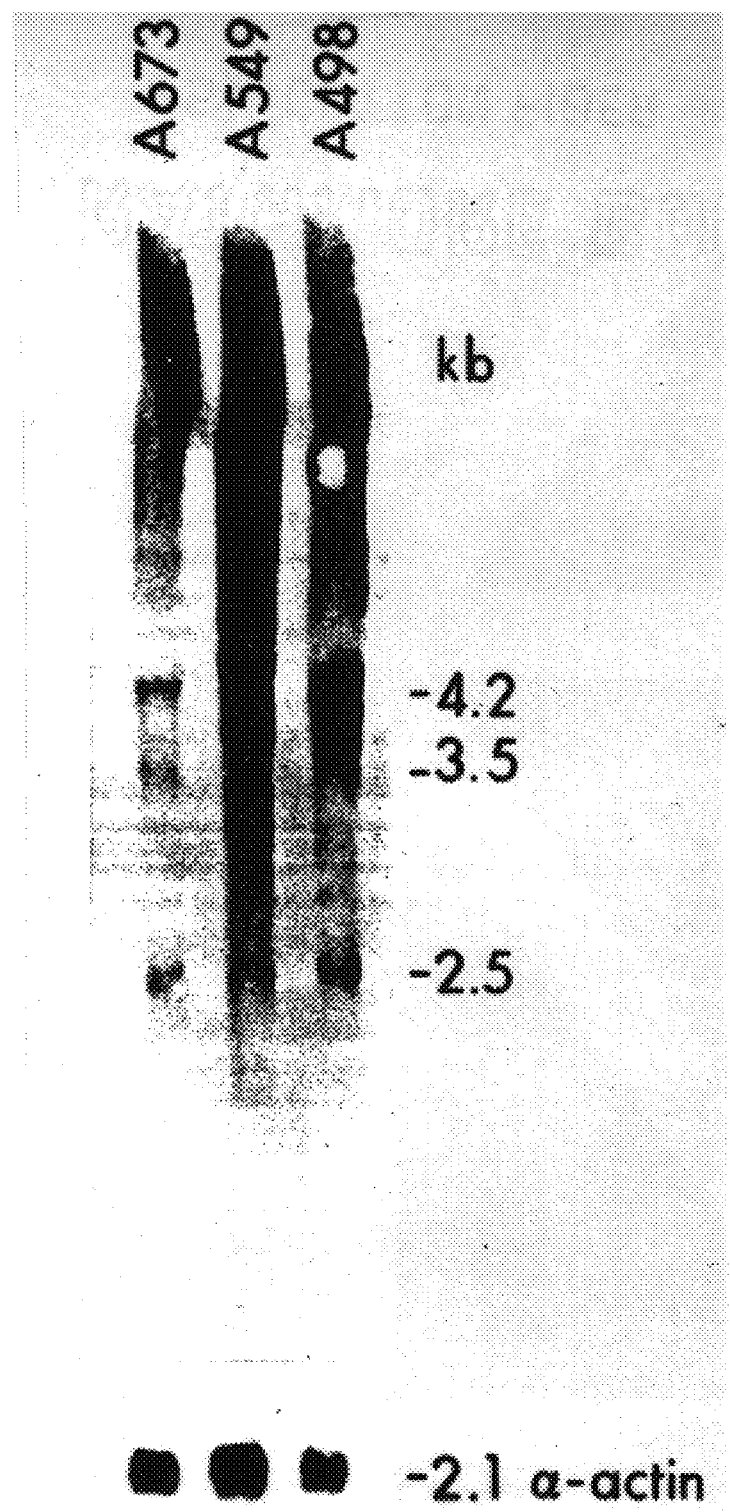

FIG. 33 shows a Northern blot analysis of A673, A549, and A498 cell lines using a Pvu II-Taq I probe from genomic sequences of the gene related to TGF-β1 and encoding the protein having tumor inhibitory activity.

Figure 34:
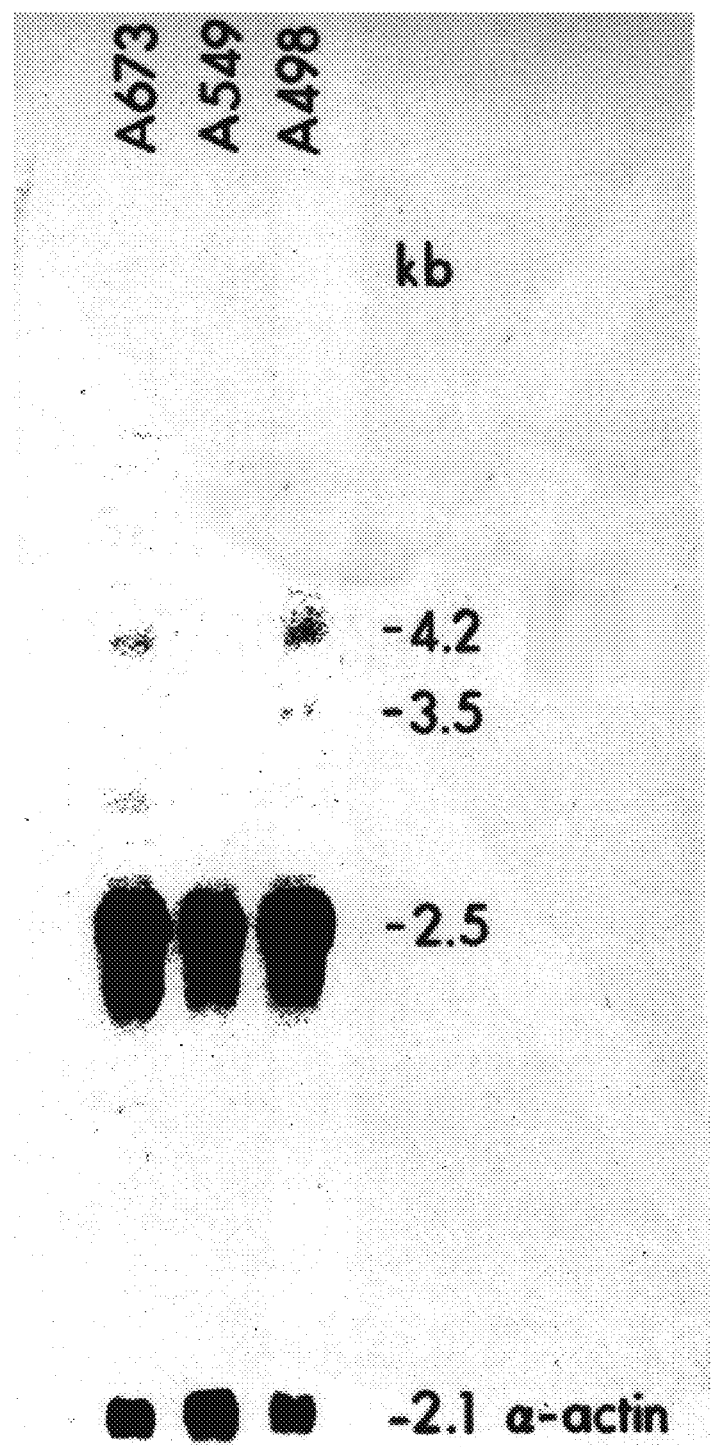

FIG. 34 shows a Northern blot analysis of A673, A549, and A498 cell lines using a Pst I-Bal I TGF-β1 probe.

Figure 35:
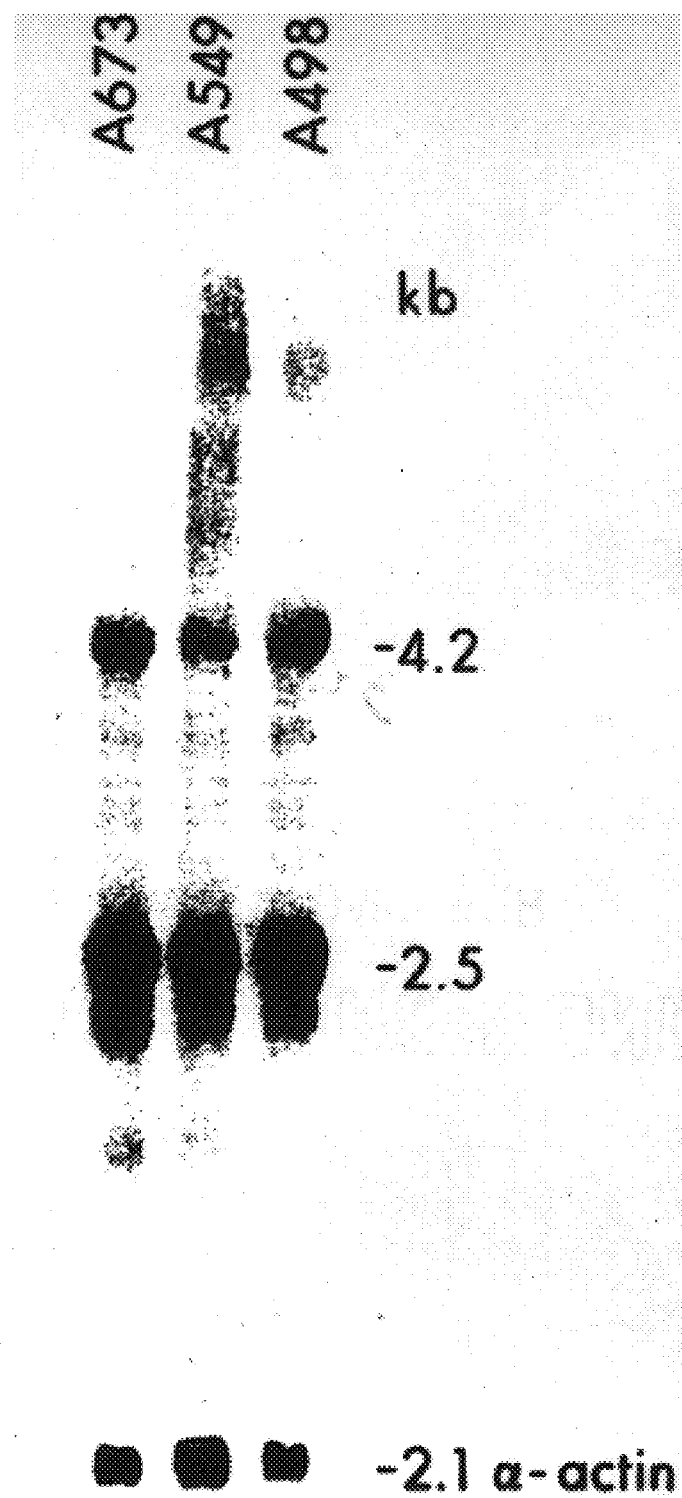

FIG. 35 shows a Northern blot analysis of A673, A549 and A498 cell lines using TGF-β1 cDNA containing the complete coding sequence of TGF-β1 precursor as a probe.

Figure 36:
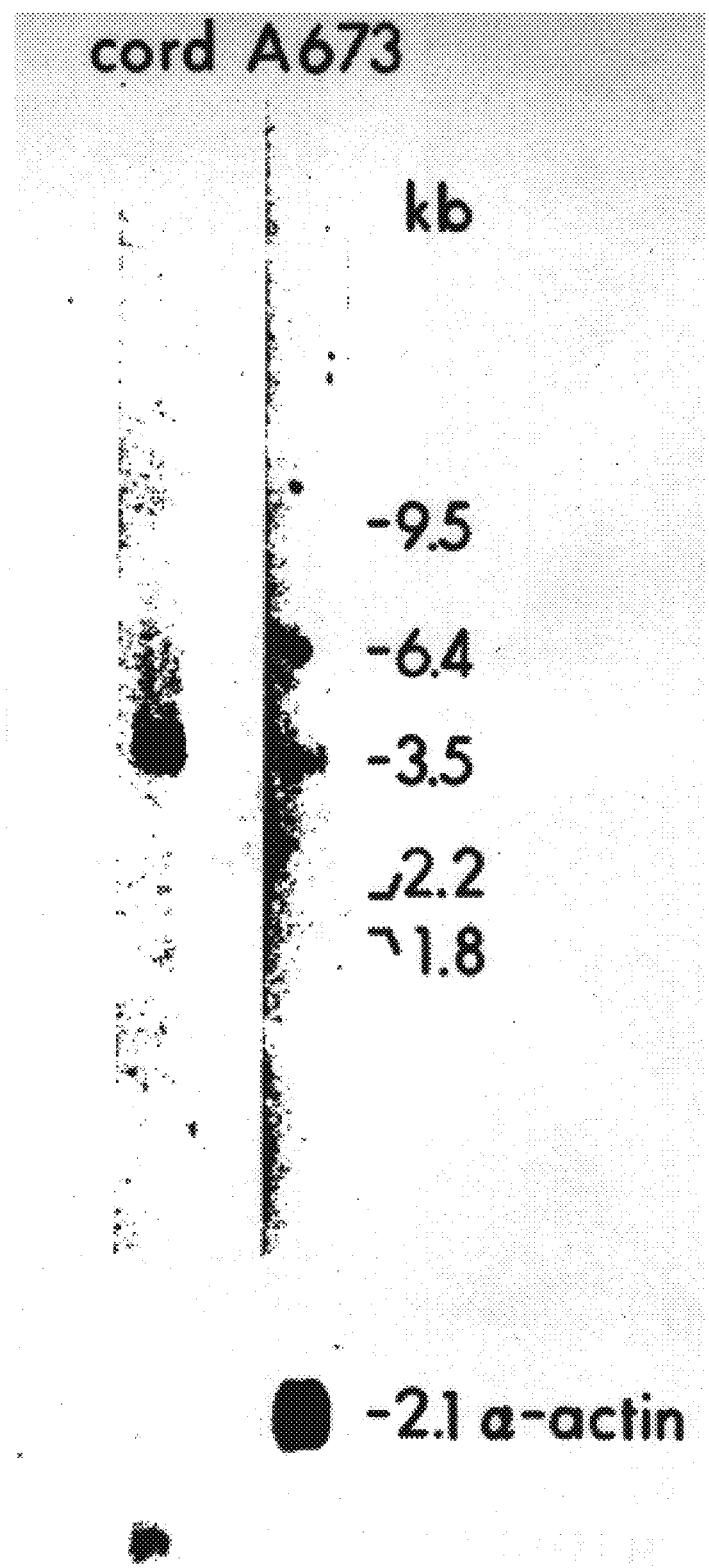

FIG. 36 shows a Northern blot analysis of mRNA from umbilical cord and A673 cell line using an Eco RI-Bgl II cDNA fragment of the gene encoding the protein having tumor growth inhibitory activity as a probe.

Figure 37:
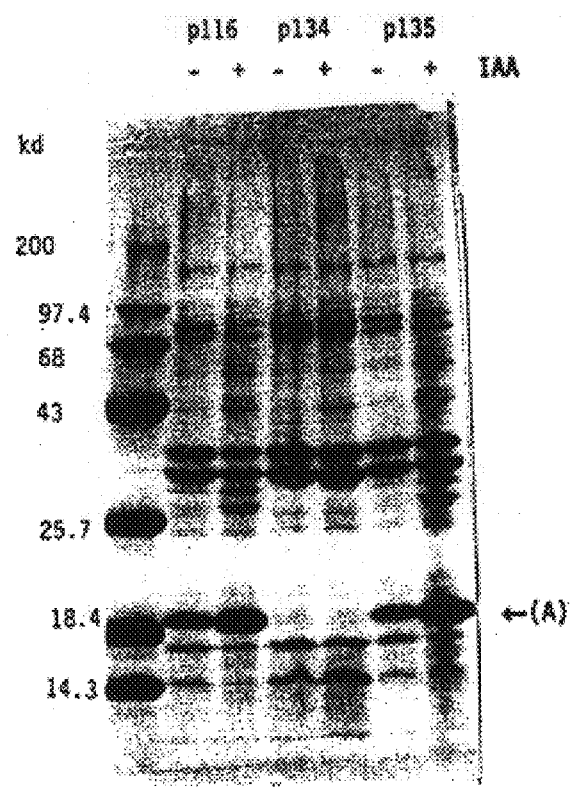

FIG. 37 shows the production of trpE::protein having tumor growth inhibitory activity fusion protein of three lysates by SDS polyacrylamide gel electrophoresis. (A) corresponds to the gene encoding the protein having tumor growth inhibitory activity.

Figure 38:
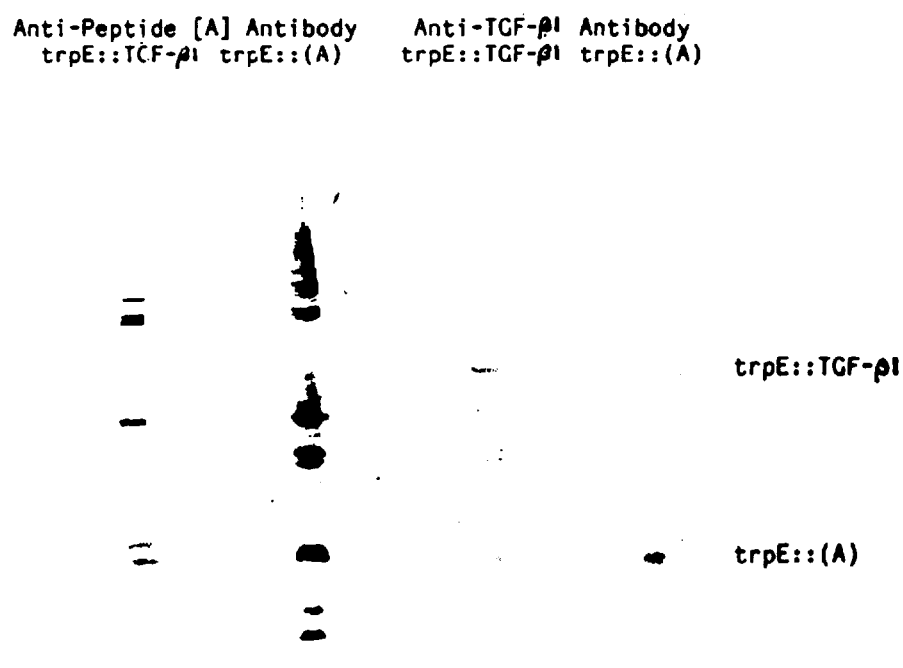

FIG. 38 shows a Western blot analysis of an antibody recognizing a fusion protein of the protein having tumor growth inhibitory activity. (A) represents the polypeptide sequences corresponding to the last 150 amino acids of the protein having tumor growth inhibitory activity.

FIG. 39 shows whole cell bacterial lysates containing trpE::TGF-β1 fusion proteins (lanes 1 and 4), trpE::(A) fusion proteins (lanes 2 and 5), and the TGF-β1 protein (purchased from R & D Systems) (lanes 3 and 6) were separated on a 12.5% SDS-polyacrylamide gel. The proteins were electrophoretically transferred to a nitro-cellulose filter (1 μm pore size) and incubated with 100 ug of affinity purified anti-peptide antibody either in the absence (lanes 1, 2 and 3) or presence of a 300 fold molar excess of the antigenic peptide (lanes 4, 5, and 6). The antibodies were detected using alkaline phosphatase conjugated to goat anti-rabbit antibody (Promega) according to the manufacturers instructions.

Detailed Description of the Invention

An acidified, ethanol extract derived from human tissue has been produced. This extract comprises a plurality of proteins. Each of the proteins has an apparent molecular weight less than about 30,000 daltons, specifically about 26,000 daltons, is a dimer composed of two polypeptides each which has an apparent molecular weight of about 13,000 daltons and each dimer is joined to the other by disulfide bonds under nonreducing conditions. The extract has the property of inhibiting the growth of human tumor cells and of an established mink lung cell line (CCL 64) while stimulating the growth of normal human foreskin fibroblasts. The inhibitory activity of the extract against human tumor cell growth is not destroyed upon increasing the temperature of the acidified, ethanol extract to about 100° C. for about 3 minutes or upon adding acetic acid until the extract is up to about 1.0 molar in acetic acid. The inhibitory activity of the acidified, ethanol extract is enhanced when it is prepared at about 4° C. rather than at about 23° C. In a preferred embodiment the human tissue is human umbilical cord, although other tissues, e.g. human placenta, may be used.

An acidified, ethanol extract derived from human umbilical cord which has been treated to remove substantially all blood and all extracellular soluble components has also been produced which comprises at least two acidic proteins. Each of the proteins has an apparent molecular weight less than about 30,000 daltons, and specifically about 26,000 daltons, is a dimer of two polypeptides each of which has an apparent molecular weight of about 13,000 daltons and is joined by disulfide bonds under nonreducing conditions. The extract has the property of inhibiting the growth of human tumor cells and of an established mink lung cell line (CCL 64) while stimulating the growth of normal human foreskin fibroblasts. The inhibitory activity against human tumor cell growth is not destroyed upon increasing the temperature of the acidified, ethanol extract to about 100° C. for about 3 minutes or upon adding acetic acid until the acidified, ethanol extract is up to about 1.0 molar in acetic acid.

Various components of the acidified, ethanol extract may be prepared using techniques known to those skilled in the art, e.g., high performance liquid chromatography and cation exchange chromatography. Thus, a protein designated tissue-derived growth inhibitor-1 (TGI-1) has the property of inhibiting the growth of human tumor cells and of an established mink lung cell line (CCL 64) but not the growth of normal human foreskin fibroblasts. TGI-1 has an apparent molecular weight of about 26,000 daltons and is a dimer composed of two polypeptides each of which has an apparent molecular weight of about 13,000 daltons and each is joined to the other by disulfide bonds under nonreducing conditions. TGI-1 is recoverable, as a defined activity on hydrophobic interaction chromatography on phenyl-Sepharose after ether ethanol precipitation at about 1.5M ammonium acetate and 31% ethylene glycol and on high performance liquid chromatography of the acidified, ethanol extract with a separating gradient of acetonitrile on a C18 column containing 0.05% trifluroacetic acid at about 26–34% and preferably 27% acetonitrile and is recoverable as a defined activity on high performance liquid chromatography of the acidified, ethanol extract with a separating gradient on a CN column of 2-propanol containing 0.05% trifluroacetic acid at about 40–41% 2-propanol.

Another composition of matter designated tissue-derived growth inhibitor (TGI) which comprises at least two polypeptides having the property of inhibiting the growth of human tumor cells and of an established mink lung cell line (CCL 64) but not the growth of normal human foreskin fibroblasts is described. TGI has an apparent molecular weight in the range from about 20,000–30,000 daltons and preferably about 26,000 daltons. TGI is resolved as a single peak of defined activity from a cation exchange resin, e.g., CM-TRISACRYL® resin when eluted by a linear NaCl gradient at about 0.6–0.7 M NaCl, is recoverable as a defined activity on high performance liquid chromatography of an acidified, ethanol extract with a linear gradient of acetonitrile containing 0.05% trifluroacetic acid at about 28–34% acetonitrile, and is recoverable as a defined activity on high performance liquid chromatography of an acidified, ethanol extract from human umbilical cord with a separating gradient of phenyl-Sepharose.

Another composition of matter designated tissue-derived growth inhibitor-2 (TGI-2) which is a protein which has the property of inhibiting the growth of human tumor cells and of an established mink lung cell line (CCL 64) but not the growth of normal human foreskin fibroblasts. TGI-2 has an apparent molecular weight of about 26,000 daltons and is a dimer composed of two polypeptides each of which has an apparent molecular weight of about 13,000 daltons and each is joined to the other by disulfide bonds under nonreducing conditions. TGI-2 is recoverable, as a defined activity on high performance liquid chromatography of an acidified, ethanol extract with a separating gradient of acetonitrile on a C18 column containing 0.05% trifluroacetic acid at about 35–39% acetonitrile and as a defined activity on hydrophobic interaction chromatography on phenyl-Sepharose after ether ethanol precipitation of about 1.5M ammonium acetate and 31% ethylene glycol and on high performance liquid chromatography of the acidified, ethanol extract with a separating gradient of 2-propanol on a CN column containing 0.05% trifluoracetic acid at about 43–45% and preferably 44% 2-propanol.

Additionally, a polypeptide designated CM-I, having the property of inhibiting the growth of human tumor cells, but not the growth of an established mink lung cell line (CCL 64) and being recoverable by cation exchange chromatography of the acidified, ethanol extract is provided.

Finally, a polypeptide recoverable from conditioned media of A431 cells having an apparent molecular weight of less than about 30,000 daltons and having the property of substantially inhibiting the growth of a human cell line (A549) but not of an established mink lung cell line (CCL 64) is provided.

This invention also provides a protein having an apparent molecular weight of about 26,000 daltons. The protein is a dimer composed of two polypeptides having an apparent molecular weight of about 13,000 daltons and being joined by disulfide bonds. The protein demonstrates tumor growth inhibitory activity of human tumor cell line (A549) and of an established mink lung cell line (CCL 64). It is acid soluble in 1.0 M acetic acid; and 0.1% trifluoracetic acid and is stable in heat to about 100° C.; and is stable in up to 39% acetonitrile nitrile and 45% 2-propanol. The protein may be designated TGI-1 or TGI-2.

This invention also provides a protein having tumor growth inhibitory activity comprising the 112 amino acids shown in FIG. 29 beginning with alanine at position 1 and ending with serine at position 112. Preferably, this protein may be a purified protein having 112 amino acids beginning with alanine at position 1 and ending with serine at position 112 as shown in FIG. 29. This 112 amino acid protein is the mature form of the protein having tumor growth inhibitory activity. The protein may also comprise the 205 amino acids shown in FIG. 29 beginning with serine at position −93 and ending with serine at position 112. Thus, this 205 amino acid sequence contains partial precursor sequence of the protein having tumor growth inhibitory activity and the complete sequence of the mature protein.

This invention further provides a nucleic acid molecule encoding the protein having tumor growth inhibitory activity comprising the 112 amino acids shown in FIG. 29 beginning with alanine at position 1 and ending with serine at position 112. The nucleic acid molecule may encode the entire protein shown in FIG. 29 beginning with serine at position −93 and ending with serine at position 112. Alternatively, the nucleic acid molecule may encode only the 112 amino acids found in the functional protein shown in FIG. 29 beginning with alanine at position 1 and ending with serine at position 112. These nucleic acid molecules may be cDNA, genomic DNA, or mRNA.

It would be obvious to one skilled in the art that certain amino acids as well as the nucleic acids encoding these amino acids may be varied without changing the function of the protein. This invention encompasses all variations of the amino acid and nucleotide sequence which produce a functional protein.

This invention also provides a plasmid which comprises the nucleic acid molecules of this invention as well as a host vector system comprising the plasmid in a suitable host cell. This host vector system comprises any plasmid and vector known in the art which are suitable for producing the proteins of this invention. The suitable host cell may be a bacteria cell or a eucaryotic cell.

This invention further provides a method for producing a protein comprising growing the host vector system of this invention so as to produce the protein having tumor growth inhibitory activity in the host and recovering the protein so produced.

This invention still further provides a polypeptide derived from the protein having tumor growth inhibitory activity comprising the 112 amino acids shown in FIG. 29 begining with alanine at position 1 and ending with serine a position 112. The polypeptide comprises the 20 amino acids shown in FIG. 29 beginning with. arginine at position 9 and ending with Leucine at position 28. The invention also provides an antibody which specifically binds to an epitope contained with the polypeptide. The antibody may be monoclonal or polyclonal.

This invention also provides an antibody which specifically binds to an epitope contained with the protein having tumor growth inhibitory activity comprising the 112 amino acids shown in FIG. 29 beginning with alanine at position 1 and ending with serine a position 112. The antibody may be monoclonal or a polyclonal.

The invention also provides a method for diagnosing a tumor which comprises contacting a sample from a human subject with an antibody of the invention under suitable conditions so as to form a complex between the antibody and an epitope contained with the protein and detecting the complex so formed, thereby diagnosing a tumor. By suitable conditions applicants contemplate any conditions which would be conducive to the formation of a complex which are known in the art.

This invention provides a pharmaceutical composition comprising the antibodies of this invention and a pharmaceutically acceptable carrier. A pharmaceutically acceptable carrier includes all carriers known in the art. Merely by way of example, the carrier may be saline. This invention further provides a method of treating a tumor which comprises administering to the subject an effective tumor treating amount of the pharmaceutical composition. This invention also provides a method of treating a proliferative type disorder which comprises administering to the subject an effective proliferative type disorder treating amount of the pharmaceutical composition. The composition may be used to treat various types of proliferative type disorders. Examples of proliferative type disorders of which the composition may be effective include arteriosclerosis, inflammation, and psoriasis.

TGI-1, TGI, TGI-2, the protein having tumor growth inhibitory activity, CM-I, or the polypeptide recoverable from conditioned media of A431 cells or various combinations thereof, may be used in pharmaceutical compositions which comprise an effective amount of TGI-1, TGI, TGI-2, the protein having tumor growth inhibitory activity, CM-I, or the polypeptide recoverable from conditioned media of A431 cells or a biologically active fragment thereof together with a suitable pharmaceutical carrier. Effective amounts may vary among the various tumor growth inhibitors depending on the indication to be treated, the patient or the stage of tumor development, by methods well known to those skilled in the art. Similarly, suitable carriers such as saline or other aqueous solutions, gels, creams and the like are well known to those skilled in the art.

TGI-1, TGI, TGI-2, the protein having tumor growth inhibitory activity, CM-I, or the polypeptide recoverable from conditioned media of A431 cells may be used to inhibit the growth of human tumor cells, e.g., carcinoma, melanoma or leukemia cells, by contacting the cells with an effective growth inhibiting amount of TCI-1, TGI, TGI-2, the protein havving tumor growth inhibitory activity, CM-T, or the polypeptide recoverable from conditioned media of A431 cells. TCI-1, TGI, TGI-2, the protein having tumor growth inhibitory activity, CM-I, or the polypeptide recoverable from conditioned media of A431 cells may also be used to treat burns or to facilitate the healing of wounds by contacting the burn or wound with a pharmaceutical composition which includes an effective amount of TGI-1, TGI, TGI-2, the protein having tumor growth inhibitory activity, CM-I, or the polypeptide recoverable from conditioned media of A431 cells and a suitable tical carrier.

This invention also provides a method of treating a proliferative type disorder in a subject which comprises administering to the subject. An effective amount of the various proteins of this invention including an effective amount of the protein having tumor growth inhibitory activity comprising the 112 amino acids shown in FIG. 29 beginning with alanine at position 1 and ending with serine at position 112 in a suitable pharmaceutical carrier effective to treat the proliferative type disorder. Various proliferative type disorders may be treated using the proteins of the invention. Examples of proliferative type disorders include arteriosclerosis, inflammation, and psoriasis. The various proteins of this invention may further be used as an immune modulator.

A method is disclosed for preparing the acidified, ethanol extract from human tissue, the acidified, ethanol extract comprising a plurality of proteins, each of which has a molecular weight less than about 30,000 daltons and preferably about 26,000 daltons and each of which has the property of inhibiting the growth of human tumor cells and of an established mink lung cell line (CCL 64) while stimulating the growth of normal human foreskin fibroblasts, the method comprising under suitable conditions treating the tissue e.g., by treating the tissue to solubilize the proteins and removing the solubilized proteins derived from the tissue, recovering the solubilized proteins, separately recovering from the solubilized tissue, proteins having an apparent molecular weight of less than about 30,000 daltons, assaying the separately recovered proteins to identify those which either inhibit the growth of human tumor cells or inhibit the growth of an established mink lung cell line (CCL 64) or enhance the growth of normal human foreskin fibroblasts, and recovering an acidified, ethanol extract containing the proteins so identified.

In a present embodiment, treating the tissue comprises suspending the tissue in a suitable acidic extraction buffer containing ethanol of about 4° C. and homogenizing the tissue for a suitable period of time to form homogenized tissue, stirring the homogenized tissue for a suitable period at about 4° C. to produce solubilized proteins.

In a present embodiment the separate recovery of polypeptides from the solubilized proteins comprises molecular sieve chromatography of the proteins.

In a present embodiment, assaying the proteins comprises separately contacting the human tumor cells, an established mink lung cell line (CCL 64) or normal human foreskin fibroblasts under suitable conditions for a suitable period with the polypeptides so as to identify polypeptides which inhibit the growth of human tumor cells, inhibit the growth of the established mink lung cell line (CCL 64) or which enhances the growth of normal human foreskin fibroblasts.

A method is also disclosed for preparing an acidified, ethanol extract from human umbilical cord, the acidified, ethanol extract comprising tissue-derived growth inhibitor (TGI) comprised of at least two proteins which have an apparent molecular weights of about 20,000–30,000 daltons and preferably about 26,000 and which has the property of inhibiting the growth of human tumor cells and of an established mink lung cell line (CCL 64) while stimulating the growth of normal human foreskin fibroblasts. The method comprises under suitable conditions, removing veins and arteries from the umbilical cord tissue and washing the tissue to remove all traces of blood, treating the tissue to produce solubilized proteins and removing the soluble containing proteins derived from the cells. Then separately recovering from the solubilized proteins TGI having an apparent molecular weight of about 26,000 daltons and assaying the separately recovered TGI to identify the activity which inhibits the growth of human tumor cells, inhibits the growth of an established mink lung cell line (CCL 64) and enhances the growth of normal human foreskin fibroblasts. Finally, recovering the acidified, ethanol extract containing the TGI so identified.

In a present embodiment, treating the tissue comprises suspending the tissue in a suitable buffer at about 4° C. and homogenizing the tissue for a suitable period of time to produce soluble proteins.

In a present embodiment, treating the tissue comprises suspending the homogenized, washed tissue in acidified ethanol for a suitable period of time to extract acid soluble proteins.

In a present embodiment, assaying the TGI comprises separately contacting the human tumor cells, e.g, human lung carcinoma line (A549), or an established mink lung cell line (CCL 64), or normal human foreskin fibroblasts (HuF), under suitable conditions for a suitable period of time with the TGI so as to identify the activity which inhibit the growth of the human tumor cells or inhibit the growth of the established mink lung cell line (CCL 64) or which stimulates the growth of normal human foreskin fibroblasts.

A method is disclosed for preparing an acidified, ethanol extract from human umbilical cord, the acidified, ethanol extract comprising tissue-derived growth inhibitor 1 (TGI-1) and tissue-derived growth inhibitor 2 (TGI-2) which have a molecular weight of about 26,000 daltons and which have the property of inhibiting the growth of human tumor cells and of an established mink lung cell line (CCL 64) while stimulating the growth of normal human foreskin fibroblasts. The method comprises under suitable conditions, removing the blood constituent by washing, treating the tissue to produce solubilized proteins and removing contaminating proteins derived from the tissue; recovering the solubilized proteins; separately recovering from the solubilized proteins TGI-1 and TGI-2 having a molecular weight of about 26,000 daltons. Then assaying the separately recovered TGI to identify the activity which inhibits the growth of human tumor cells, inhibits the growth of an established mink lung cell line (CCL 64) and enhances the growth of normal human foreskin fibroblasts. Finally, recovering the acidified, ethanol extract containing the TGI so identified.

In a present embodiment, treating the tissue comprises suspending the tissue in a suitable acidic extraction buffer and homogenizing the tissue at about 4° C. for a suitable period of time to form homogenized tissue.

In a present embodiment, recovering the acid solubilized proteins comprises suspending washed tissue in a suitable acidic extraction buffer containing ethanol at about 4° C. for a suitable period of time.

In a present embodiment the assaying the TGI-1 and TGI-2 comprises separately contacting the human tumor cells, an established mink lung cell line (CCL 64) or normal human foreskin fibroblasts under suitable conditions for a suitable period with the polypeptides so as to identify the TGI-1 and TGI-2 which inhibit the growth of the established mink lung cell line (CCL 64) or which enhance the growth of normal human foreskin fibroblasts.

In a present embodiment the separate recovery of polypeptides from the solubilized proteins comprises hydrophobic interaction chromatography using phenyl-Sepharose.

A method for preparing a composition of matter designated tissue-derived growth inhibitor-1 (TGI-1) which comprises first preparing the acidified, ethanol extract and then recovering TGI-1 from the acidified, ethanol extract as a defined activity by high performance liquid chromatography,. e.g., purification of the acidified, ethanol extract by hydrophobic interaction chromatography in a phenyl-Sepharose column followed by reverse phase HPLC with either i) a separation gradient of acetonitrile on a C18 column containing 0.05% trifluoracetic acid at about 26–34% acetonitrile and preferably 27% acetonitrile or ii) a separation gradient of 2-propanol containing 0.05% trifluroacetic acid at about 40–41% 2-propanol.

A method for preparing a composition of matter designated tissue-derived growth inhibitor (TGI) which comprises first preparing an acidified, ethanol extract and then recovering TGI from the acidified, ethanol extract as a defined activity on high performance liquid chromatography, e.g. reverse phase HPLC of the acidified, ethanol extract with a linear gradient of acetonitrile containing 0.05% trifluoracetic acid at about 28–34% acetonitrile, or as a single peak of activity from a cation exchange resin, e.g., CM-TRISACRYL® resin when eluted with a linear NaCl gradient at about 0.6–0.7 M NaCl.

A method for preparing a composition of matter designated tissue-derived growth inhibitor-2 (TGI-2) which comprises first preparing the acidified, ethanol extract and then recovering TGI-1 from the acidified, ethanol extract as a defined activity by high performance liquid chromatography, e.g., purification of the acidified, ethanol extract by hydrophobic interaction chromatography in a phenyl-Sepharose column followed by reverse phase HPLC with either i) a separation gradient of acetonitrile on a C18 column containing 0.05% trifluoracetic acid at about 28–30% acetonitrile or ii) a separation gradient of 2-propanol containing 0.05% trifluoracetic acid at about 43–45% and preferably about 44% 2-propanol.

A method of preparing a polypeptide designated CM-I, which comprises first preparing the acidified, ethanol extract and then recovering the CM-1 from the acidified, ethanol extract by ion exchange chromatography, e.g. cation exchange chromatography.

A method for detecting the presence of a tumor is disclosed. The method comprises quantitatively determining the amount of TGI-1, TGI, TGI-2, the protein having tumor growth inhibitory activity, CM-I, or the polypeptide recoverable from conditioned media of A431 cells present in a sample, e.g., blood, amniotic fluid, peritoneal fluid, ascites fluid, cerebrospinal fluid or urine, from a subject and comparing the amount so determined with the amount present in a sample from a normal subject, the presence of a significantly different amount, e.g. a significantly higher amount, indicating the presence of a tumor.

Another method for detecting the presence of a tumor is disclosed. The method comprises separately quantitatively determining both the amount of TGI-1, TGI, TGI-2, the protein having tumor growth inhibitory activity, CM-I, or the polypeptide recoverable from condition media of A431 cells and of transforming growth factor alpha (TGF-alpha) present in a sample from a subject, determining the ratio of the amount of TGI-1, TGI, TGI-2, the protein having tumor growth inhibitory activity, CM-I, or the polypeptide recoverable from conditioned media of A431 cells present in the sample to the amount of TGF-alpha present in the sample from a subject, determining the ratio of the amount of TGI-1, TGI, TGI-2, the protein having tumor growth inhibitory activity, CM-I, or the polypeptide recoverable from conditioned media of A431 cells present in the sample, determining the comparable ratio for a sample from a normal subject and comparing the ratio for the sample from the subject to the ratio for the sample from the normal subject, a significant variation in the ratio indicating the presence of a tumor.

A method for typing tumors is disclosed which comprises determining for a sample from a subject with a tumor the presence of one or more TGI-1, TGI, TGI-2, the protein having tumor growth inhibitory activity, CM-I, or the polypeptide recoverable from conditioned media of A431 cells, the presence or absence of a specific combination thereof, e.g., TGI and CM-I or TGI-1 and TGI-2 being indicative of a specific tumor type, e.g., a melanoma or a carcinoma.

A method for typing tumors is disclosed which comprises quantitatively determining for a sample from a subject with a tumor the amount of each of TGI-1, TGI, TGI-2, the protein having tumor growth inhibitory activity, CM-I, or the polypeptide recoverable from conditioned media of A431 cells present in the sample, the presence of specific amounts or relative amounts thereof, e.g, a significant increase in the amount of TGI or a significant variation in a ratio such as the ratio of TGI-1 to CM-I.

EXPERIMENTAL DETAILS

Four sets of experiments are discussed below. Each series of experiments comprises a means of isolating proteins exhibiting tumor growth inhibitory activity. In the first series of experiments six discrete proteins are purified that demonstrated tumor growth inhibitory activity. These proteins were designated TGI, TGI-1, TGI-2 and CM I–IV. The second and third series of experiments are improvements of the purification process resulting in more purified proteins demonstrating tumor growth inhibitory activity. In the fourth series of experiments TGF-β1 was cloned and used to isolate a related gene encoding a protein having tumor growth inhibitory activity. Although it has not yet been determined which of TGI-1 or TGI-2 corresponds to the protein having tumor growth inhibitory activity, one skilled in the art would understand that such a correspondence exists although the exact nature of this correspondence remains to be clarified.

First Series of Experiments

Materials and Methods

Isolation of Tissue-Derived Tumor Growth Inhibitors (TGIs) From Tissue Extracts

Human umbilical cord or placenta tissues were extracted using a modification of the acid/ethanol extraction procedure described by Davoren et al (Biochem. Biophys. Acta. 63:150 (1962) and Roberts et al, Proc. Natl. Acad. Sci. USA. 77:3494 (1980).

The buffer for extraction consisted of 375 ml of 95% (v/v) ethanol (punctilious, 190 proof, U.S. Industrial Chemicals, #UN1170), 7.5 ml of concentrated HCl, 33 mg of phenylmethylsulfonyl fluoride (PMSF) (Sigma P-7627) and 1 ml of Aprotinin (Sigma A6012 with 19.8 Trypsin inhibitor units per ml in 0.9% NaCl and 0.9% benzyl alcohol) mixed with 192 ml of distilled water at 4° C. Four hundred to six hundred grams of frozen human umbilical cords or placentas (Advanced Biotechnologies) (stored at −80° C.) were thawed at 4° C. for six hours. The thawed tissue was placed in a 4° C. chilled Cuisinart food processor (Model DLC-7-PRO) and suspended in 200 ml of 4° C. extraction buffer. The suspended tissue was homogenized by the food processor. After the first minute of homogenization, the suspension became creamy white. Another 200 ml of 4° C. extraction buffer was added to this white suspension. The suspension changed to a dark coffee brown color. The tissue suspension was homogenized for a total of 10 min. at 4° C. Extraction buffer was added to this homogenized tissue mixture to a final volume of 6 ml per gram of tissue homogenate.

The homogenized tissue suspension was transferred to a large 4 liter beaker with a 3 inch stir bar and stirred at half of the maximum stirring capacity of a Lab-line Multimagnestir multi-mixer, Model #1278. After over-night extraction with stirring at 4° C., the homogenate was transferred to 1 liter centrifuge bottles (Sorvall) and centrifuged at 3500 rpm (RCF=350) for 30 minutes at 4° C. in a Sorvall RC-3B centrifuge equipped with a Sorval H-6000A rotor. The supernatant was transferred to a large 4 liter beaker and adjusted to pH 5.0 with the slow addition of concentrated ammonium hydroxide. With increasing pH, the color of the supernatant changed from brown to an orange solution. The solution was precipitated following the addition of 2.0 M ammonium acetate, pH 5.2, added at an amount of 1% of the total volume. This precipitate was removed following centrifugation at 4500 rpm (RCF=5900) for 4 hours in a Sorvall RC-3B at 4° C. The supernatant was transferred to large 6 liter flasks to which four volumes of anhydrous ether (−20° C.) (Baker 9244-3) and two volumes of 95% ethanol (4° C.) were added. The mixture was allowed to stand undisturbed at −22° C. for 48 hours to allow the resulting precipitate to settle.

At the end of the 48 hr precipitation, the etherized material was brought to ambient temperature in a fumehood. Warming of the acidified, ethanol extract to ambient temperature enhances the aggregation of the precipitate. The clear organic phase of ether and ethanol was removed by a water aspirator and the precipitate was left in the fume hood for several hours to allow the residual organic phase to evaporate. The "dried" precipitate was dissolved in 1.0 M acetic acid and dialyzed extensively against 1.0 M acetic acid (Baker #9507-5) using dialysis membranes with a molecular cutoff of 3500 (Spectropor 3, Spectrum Medical Industries, Los Angeles, Calif.). The dialyzed acidified ethanol extract was lyophilized in 250 ml Corning conical centrifuge tubes (Corning 25350) and stored as crude acidified, ethanol extract.

An alternative procedure for precipitating TGIs from the acidified, ethanol extract replaces the addition of four volumes of ether and two of ethanol with the addition of only the two volumes of ethanol at 4° C. The advantage of eliminating ether from the acidified, ethanol extract precipitation step was the elimination of a step requiring the use of a highly flammable solvent which makes the procedure and any scale-up of the processing of large amounts of materials difficult.

Gel Filtration Chromatography

Lyophilized crude acidified, ethanol extract was resuspended in 1.0 M acetic acid (10–30 mg/ml) and clarified by centrifugation at 3500 rpm for 30 min at 4° C. in a Sorval RC-3B centrifuge equipped with a Sorvall H-6000A rotor before sample application to the column. Sample volumes of one hundred to 150 ml were chromatographed on Bio-Gel® P10, 100–200 mesh (Bio-Rad; 150–1040) in 1.0 M acetic acid at either 23° or 4° C.

The column (14×100 cm) (Amicon; #86012) contained 13.8 liters of equilibrated and degassed Bio-Gel® P10 in 1.0 M acetic acid at. either 23° C. or 4° C. The void volume was determined by the addition of 50 ml of blue dextran (Sigma #D5751) at 2 mg/ml in 1.0 M acetic acid. After calibration, the column was "conditioned" with 100 ml of bovine serum albumin (Sigma #A-4503) at 100 mg/ml in 1.0 M acetic acid followed by extensive washing with 1.0 M acetic acid.

Following sample application, 1 liter fractions were collected using a SuperRac® (LKB 2211) equipped with a type C collection rack, at a flow rate of 7 ml/min into 2 liter plastic tissue culture roller bottles (Falcon; 3207). Fractions were monitored by a Uvicord® S (LKB 2138) at 280 nm set at an absorbance range of 2.0 AUFS and recorded by a single channel chart recorder (LKB 2210). One ml aliquots were removed from each fraction, lyophilized and assayed for tumor growth inhibitory activity as described. The remainder of each fraction was lyophilized in 2 liter lyophilization jars (Virtis® #6503-2050) using a Virtis freeze-model 24.

High Performance Liquid Chromatography (HPLC)

Individual fractions containing TGT activity from the Bio-Gel® P-10 column were lyophilized and resuspended in 1 to 10 ml of 0.05% trifluoracetic acid (TFA) (Pierce #28901) depending upon the amount of protein in each fraction. Water used for HPLC was generated using a Milli-Q water purification system. Starting buffer in all HPLC chromatography runs consisted of Milli-Q water containing 0.05% TFA. Prior to injection, the sample was centrifuged in a Beckman tabletop centrifuge (Beckman TJ-6) at 3000 rpm for 20 min to remove insoluble material. The supernatant was injected into either a Waters uBondapak® analytical $C_{18}$ column (0.39×30 cm) (Waters PN27324) or semipreparative column (0.78×30 cm) (Waters PN84176) as specified in individual experiments. A waters automated gradient controller (Waters Model 510) was utilized for column elution monitored by a variable wavelength u.v. detectors (waters Lambda-Max, Model 481) set at 206 nm. The solvent used for elution was either acetonitrile (Baker 9017-3) or 2-propanol (Fisher, A452) containing 0.05% TFA. Fractions were collected by a SuperRac® (LKB 2211) equipped with a type B collection rack into siliconized (Pierce, Aquasil #42799) 13×100 mm or 16×100 mm test tubes. Aliquots from each collected, fraction were assayed for tumor growth inhibitory activity as described below.

Ion Exchange Chromatography

Both the lyophilized material from the acidified, ethanol and ether extractions and various lyophilized fractions derived from the Bio-Gel® P-10 gel filtration chromatography were separately subjected to ion exchange chromatography. CM, SP, and DEAE-TRISACRYL® (LKB) ion exchange resins were used in these procedures. The samples for chromatography were diluted to a final concentration of approximately 20 mg/ml in 1.0 M acetic acid. The samples were dialyzed at 4° C. until both the pH and conductivity were equal to the starting (equilibration) buffer. All ion exchange chromatographic procedures were performed at 4° C.

a. Chromatography Using CM- and SP-TRISACRYL® Ion Exchange Results

The resins, as aqueous suspensions, were suspended in an equal volume of 0.1 M ammonium acetate, pH 4.0, containing 1.0 M NaCl. The resin was allowed to equilibrate for at least 3 hours and was degassed at 4° C. Twenty ml of resin was packed into a 1.6×20 cm column (Pharmacia; #19-0362-01) and washed with 2 column volumes of 1.0 ammonium acetate, pH 4.0, followed by 0.01 M ammonium acetate, pH 4.0. The column was washed until the effluent exactly matched the conductivity of the equilibrating buffer (i.e., 0.01M ammonium acetate, Fisher A637), pH 4.0. The sample was applied to the resin (1 gm/20 ml resin) at a flow rate of 1 ml/min, the column was washed with equilibration buffer until the optical density leveled (e.g., approaching zero optical density) and 200 ml of an ascending molarity linear gradient (Pharmacia gradient mixer GM-1, #19-0495-01) was applied through a column flow adaptor of concentrations 0.01 to 1.0 M ammonium acetate, pH 4.0. In certain experiments, a second gradient was applied to the same column. This second gradient ranged from 1.0 M ammonium acetate, pH 4.0, to 50% acetonitrile in 1.0 M ammonium acetate, pH 4.0. Two ml fractions were collected in polystyrene tubes, 13×100 mm, (Columbia Diagnostics; B2564) in a SuperRac® Fraction collector (LKB 2211), equipped with an A type collection rack. All column chromatography was performed with the aid of a Uvicord S with a 280 nm filter (LKB 2138) and a single channel recorder (LKB 2210). Fractions were aliquoted based upon optical density ranging from 100 ul to 1 ml, and assayed for tumor growth inhibitory activity.

b. Chromatography using DEAE-TRISACRYL

The chromatographic resin preparation and procedure was performed exactly as described for CM- and SP-TRISACRYL® chromatography, except the equilibration buffer used was 0.1 M ammonium acetate, pH 6.0, the gradient elution ranged from 0.1 M to 1.0 M ammonium acetate, pH 6.0, and the sample was equilibrated in the above mentioned equilibration buffer.

Monolayer Assay for Tumor Growth Inhibitory Activity

Test cells were sub-cultured on 96-well tissue culture plates (Nunc 167008) in 50 ul of Dulbecco's modified Eagle's medium (Whittaker M.A. Bioproducts 12-6143) containing 10% fetal bovine serum (Whittaker M.A. Bioproducts 14-501B), 2% L-glutamine (Whittaker M.A. Bioproducts 17-605-A), 1% penicillin and 1% streptomycin. Human lung carcinoma cells, A549, and normal human fibroblasts (HuF) required a seeding density of $5 \times 10^3$ cells per well. Mink cells (ATCC: CCL 64) required a seeding density of $4.5 \times 10^3$ cells per well.

Aliquots from column fractions to be assayed for tumor growth inhibitory activity were transferred to sterile 12×75 mm tubes (Falcon 2058) containing 50 of microliters 1 mg/ml solution of bovine serum albumin (BSA; Sigma A-6003) in 1 M acetic acid and lyophilized. Immediately prior to the assay, the lyophilized sample was resuspended in 400 $\mu$l, for each cell type tested. One hundred microliters aliquots of the resuspended sample were added to wells containing test cells. Each sample was assayed in triplicate. The cells were incubated for 72 hours at 37° in a humidified 5% $CO_2$/95% air atmosphere. At the end of the incubation period, each well was pulsed with 100 microliters of complete medium containing 1 $\mu$Ci/ml 5-[$^{125}$I]Iodo-2'deoxyuridine ($^{125}$IUdR) (New England Nuclear; NEX-072) for 24 hours. The monolayers were washed once with wash buffer A (Dulbecco's phosphate buffered saline, with 10 mM $MgCl_2$, containing 1 mg/ml BSA, pH 6.8), fixed for 10 minutes in methanol (Fisher A452), and air dried for 15 minutes. The $^{125}$IUdR incorporated by the cells was solubilized with 200 microliters of 1.0 N NaOH and the plates incubated for 20 minutes at 60° C. Solubilized $^{125}$IUdR was collected using the Titertek Supernatant Collection System® (Skatron Inc., 7072). The amount of cell growth is approximated by the extent of $^{125}$IUdR incorporated into the DNA of cells in the log phase of growth. Before the assay was harvested each well was observed using a Zeiss® inverted microscope to visually note the amount of cell growth. Inhibition or stimulation of growth was expressed as a ratio of $^{125}$IUdR incorporated by test cells (e.g. human tumor cells) containing the test aliquots relative to $^{125}$IUDR incorporated by the untreated control cells. The inhibition or stimulation observed by microscopic examination of treated cells corresponded well with decreased or increased incorporation of $^{125}$IUdR, respectively.

Characterization of TGI Activities a. Heat Treatment

One ml aliquots from fractions 2, 4, and 6 obtained from gel filtration chromatography on Bio-Gel® P-10, were lyophilized in 12×75 mm polystyrene tubes (Falcon 2034) and resuspended in 1 ml of 1.0 M acetic acid. The samples were heated for 3 minutes in a boiling water bath, lyophilized, and assayed for tumor growth inhibitory activity as described above.

SDS-Polyacrylamide Slab Gel Electrophoresis

Aliquots from samples from each chromatographic procedure were lyophilized for electrophoresis. Samples were diluted in 80 microliters of sample buffer containing 0.1 M Tris-HCl (Sigma; T-1503), pH 6.8, 15% glycerol (Kodak;

114-9939), 2% sodium dodecyl sulfate (SDS) Bio-Rad; 116-0302), and 5% 2-mercaptoethanol (Bio-Rad; 161-0710), and electrophoresis on a 5–20% acrylamide linear gradient essentially as described (Laemmli, U. K. (1970) Nature 227, 680–685). The samples were boiled for 2 minutes prior to application to a 1.5 mm wide slab gel in a Bio-Rad Model 155 Vertical Electrophoresis Cell (BioRad® 165-1420) under constant current at 30 mA per gel for 4 hours (Hoeffer power supply; PS 1200 DC) at 9° C. Constant temperature was maintained by a water bath circulator (Haake, A81). Gels were stained with 0.5% Coomassie Blue R250 (Bio-Rad #16-0400) in 5.7% acetic acid and 47% methanol overnight and destained in the same solution without stain. Specific gels demonstrating low concentrations of proteins were restained by a silver technique as described by Merril (Merril, C. R., Goldman, D., Sedman, S. and Ebert, M. H. (1981) 211:1437–1438), (Bio-Rad silver staining kit; #161-0443).

Results

Comparison of Tumor Growth Inhibitory Activities from Gel Filtration Chromatography on Bio-Gel P10 at Room Temperature and at 4° C.

The growth inhibitory activity derived from acidified, ethanol extracts of human umbilical cords eluted by gel filtration chromatography using Bio-Gel® P10 resin with apparent molecular weights ranging from 5,000–16,000 daltons. Occasionally, another peak of activity has been observed at molecular weights ranging from 3000–5000 daltons. The molecular weight calculations are based on the elution profiles of molecular weight standards (i.e., carbonic anhydrase—29,000; RNase—14,400; insulin—6,000) chromatographed on 1 liter of resin in a column of 4×100 cm. The elution profile derived from the column and from the large 14×100 cm column were superimposable. Acidified, ethanol extracts from human placenta identically chromatographed demonstrated elution profiles very similar to the umbilical cord extracts.

Fractions 1 to 3 from the umbilical cord acidified, ethanol extract are a very intense brown color; the color gradually disappears as the fractions progress. Fortunately, although (TGI) eluted in fractions 1, 2, and 3 containing the highest protein concentrations, the majority of activity extends past the observed protein peaks as is clearly demonstrated in FIGS. 1 and 2. Extracts from human placental material showed a greater overlap of TGI with the major protein peaks than was observed with material from human umbilical cords (data not shown). Aliquots of identical volumes from gel filtration chromatography electrophoresed by SDS-PAGE on a 5–20% polyacrylamide gradient also illustrated that by fraction 4, considerably less protein is found than in fractions 1 to 3. In fractions 5 an 6, major protein bands of 5,600 and 14,000 band are observed and by fraction 7 very little protein remains, although inhibitory activity extends into fraction 10 as shown in FIG. 2. The obvious advantage of the majority of activity eluting in regions of less protein is that it facilitates further purification of TGIS.

Figure 1:
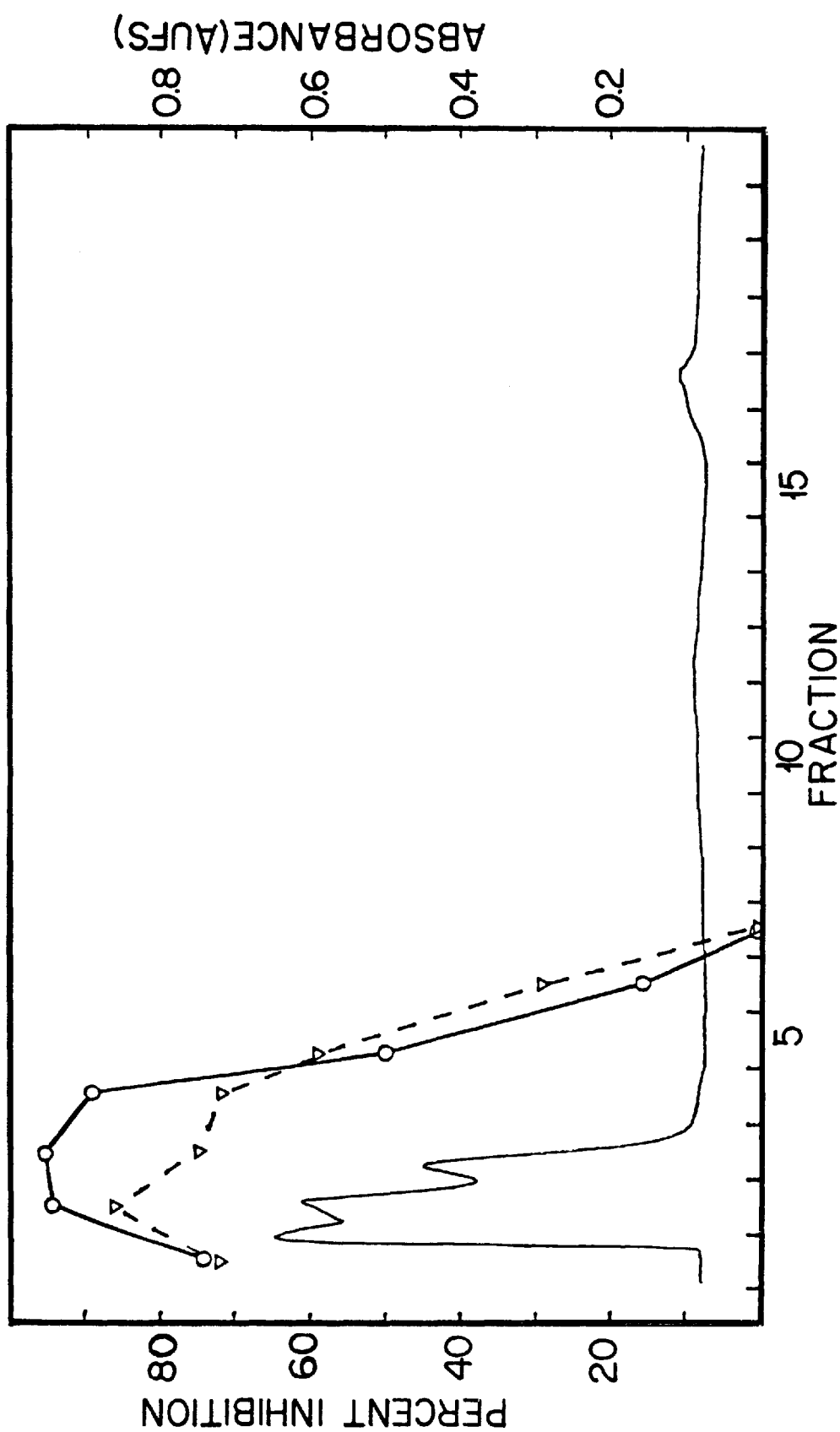
FIG. 1 shows gel filtration chromatography at 23° C. Elution pattern of gel filtration chromatography at 23° C. of crude acidified, ethanol extract from human umbilical cords. Two grams of acidified, ethanol extract in 150 ml of 1.0 M acetic acid was applied to a 14×100 cm column (Amicon; #86012) containing Bio-Gel® P10 and eluted at a flow rate of 7 ml/min. One liter fractions were collected on a Super-Rac® (LKB 2211) equipped with a type C collection rack (LKB). One ml aliquots of each fraction (1 liter/fraction) were transferred to 12×75 mm sterile snap top tubes (Falcon 2058). TGI activity was determined as described in Materials and Methods. Inhibition of A549 human lung carcinoma cells is shown by triangles and mink lung (CCL 64) cells by circles. Absorbance at 280 nm (———) was detected by a Uvicord S® (LKB 2138) with a full scale absorbance range of 1.0 AUFS and a single channel chart recorder (LKB 2210) with a chart speed of 1 mm/min.
Figure 2:
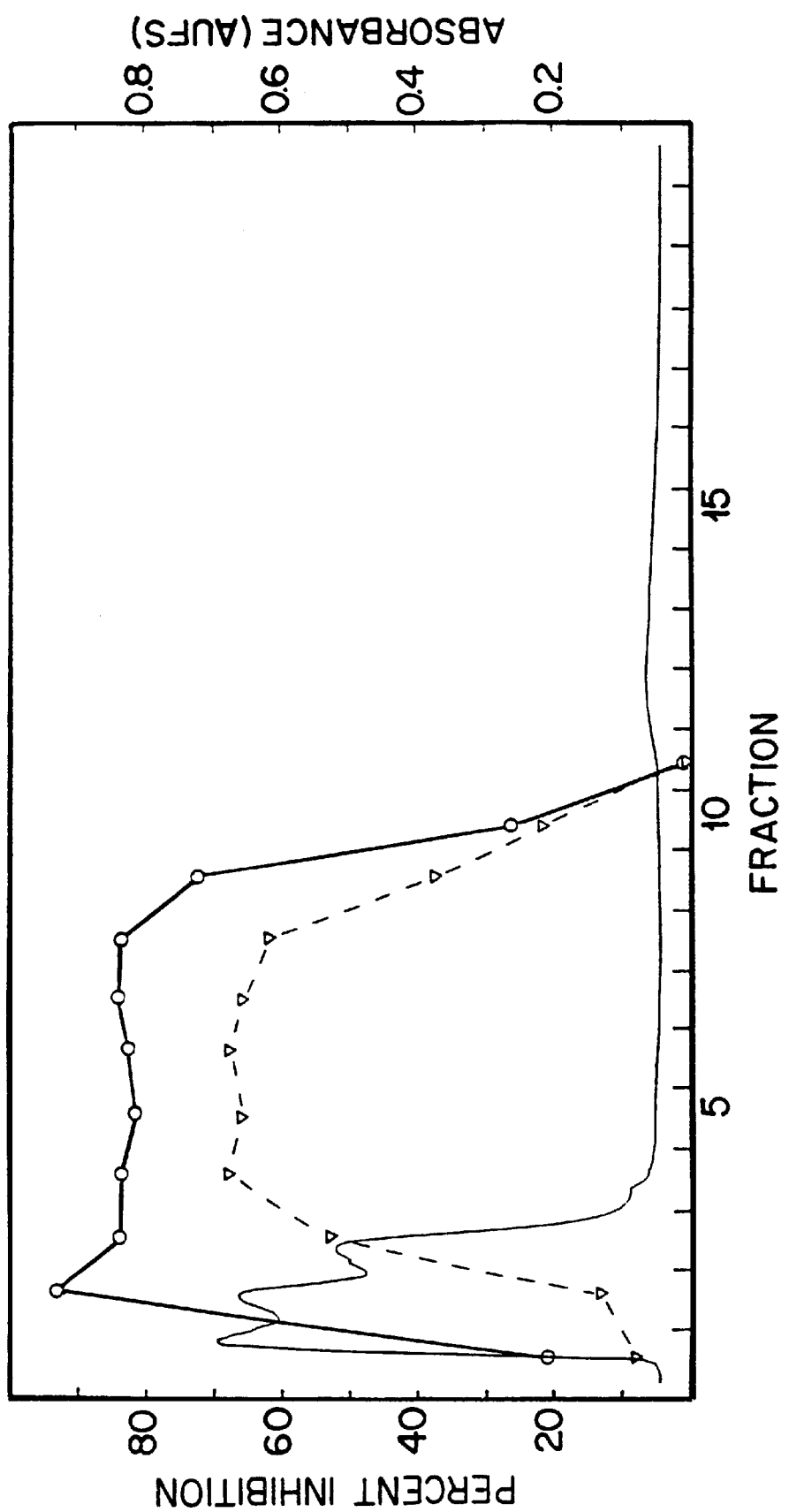
FIG. 2 shows gel filtration chromatography at 4° C. Elution pattern of gel filtration chromatography at 4° C. of crude acidified, ethanol extract from human umbilical cords. Two grams of acidified, ethanol extract in 150 ml of 1.0 M acetic acid was applied to a 14×100 cm column (Amicon; #86012) containing Bio-Gel® P10 and eluted at a flow rate of 7 ml/min. One liter fractions were collected on a Super-Rac® (LKB 2211) equipped with a type C collection rack (LKB). One ml aliquots of each fraction (1 liter/fraction) were transferred to 12×75 mm sterile snap top tubes (Falcon 1058). Tumor growth inhibitory activity was determined as described in Materials and Methods. Inhibition of A549 human lung carcinoma cells is shown by open triangles and mink lung (CCL 64) cells by open circles. Absorbance of 280 nm (———) was detected by a Uvicord S® (LKB 2138) with a full scale absorbance range of 1.0 AUFS and a single channel chart recorder (LKB 2210) with a chart speed of 1 mm/min.

A comparison of Bio-Gel® P-10 chromatograms performed at room temperature and 4° C., illustrated in FIGS. 1 and 2, respectively, clearly indicate that inhibitory activity is better preserved at 4° C. At 23° C., no activity is observed past fraction 6 (FIG. 1), while at 4° C., activity is extended for 4 more fractions to fraction 10. Most importantly, the net amount of activity recovered is at least two-fold higher when extracts are chromatographed at 4° C., since 80% or more tumor growth inhibitory activity is obtained in 7 fractions at 4° C. (FIG. 2) and in only 3 fractions at 23° C. This was not due to a concentration of the same quantity of activity eluting in 3 fractions (23° C.) rather then being spread over 7 fractions (4° C.), but apparently to actual increase in the yield of tumor growth inhibitory activity. One ml aliquots of fraction 5 from both columns separately and dilutions of these fractions to 1/5 to 1/125 were tested on both the human lung adenocarcinoma (A549) and mink lung cells (CCL 64) (Table 1). The tumor growth inhibitory activity of the undiluted fraction was 2-fold higher in the fraction 5 obtained from chromatography at 4° C. Moreover, a 25-fold dilution of fraction 5 from chromatography at 4° C. continued to yield maximum tumor growth inhibitory activity against the human tumor cell line. A fraction of equivalent dilution from chromatography at 23° C. showed no detectable activity. A similar observation was made with the mink cell line. This information was not based on activities observed in FIGS. 1 and 2 but from two separate columns which demonstrated equivalent TGI activities in their respective fifth fraction.

Comparison of the Effects of TGIs on Normal Human Fibroblasts (HuFs) and Transformed Human Lung Carcinoma Cells (A549)

Figure 3:
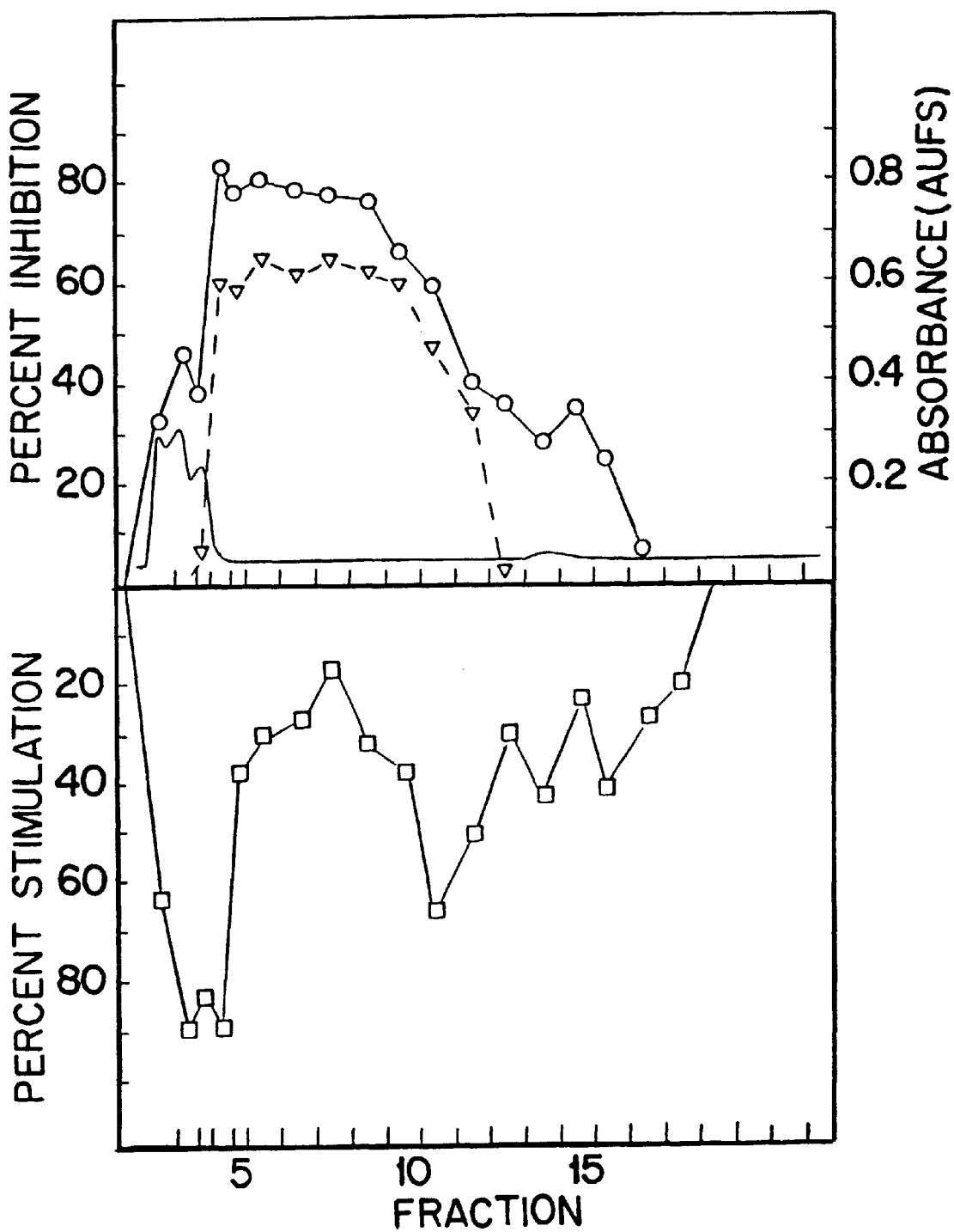
FIG. 3 shows cell growth inhibition and normal human cell stimulation by fractions from gel filtration chromatography at 4° C. Elution pattern of gel filtration chromatography at 4° C. of crude acidified, ethanol extract in 150 ml of 1.0 M acetic acid was applied to a 14×100 cm column (Amicon; #86012) containing Bio-Gels® P10 and eluted at a flow rate of 7 ml/min. One liter fractions were collected on a SuperRac® (LKB 2211) equipped with a type C collection rack (LKB). One ml aliquots of each fraction (1 liter/fraction) were transferred to 12×75 mm sterile snap top tubes (Falcon 2058). Tumor growth inhibitory activity was determined as described in Materials and Methods. Inhibition of A549 human lung carcinoma cells is shown by open triangles and mink lung (CCL 64) cells by open circles. Stimulation of normal human fibroblasts is shown by open squares. Absorbance of 280 nm (————) was detected by Uvicord S® (LKB 2138) with a full scale absorbance range of 1.0 AUFS and a single channel chart recorder (LKB 2210) with a chart speed of 1 mm/min.

Aliquots of fractions obtained from human umbilical cord acidified, ethanol extracts chromatographed on a Bio-Gel® P-10 resin, (4° C.), were tested for tumor growth inhibitory activity on human normal and transformed cells as described in Materials and Methods. As illustrated in FIG. 3, tumor growth inhibitory activity against human A549 cells (open triangles) ranged from fractions 3 to 12, while these same fractions induced as much as an 85% increase in growth stimulation of the normal human fibroblasts. Thus, the inhibitory activity is specific for human tumor cells. This observed inhibitory activity is not due to cytotoxicity, as demonstrated by light microscopic studies and indirectly by its stimulatory effect on normal human fibroblasts. The TGI's have previously been (tested on "normal" epithelial derived cells and similar results were observed.

TABLE 1

EFFECT OF TEMPERATURE ON THE RECOVERY OF TUMOR GROWTH INHIBITORY ACTIVITY FROM GEL FILTRATION CHROMATOGRAPHY

| TEMPERATURE OF COLUMN RUN | PERCENT INHIBITION OF THE TEST CELL | |
|---|---|---|
| TEST CELL LINE | 4° C. | 23° C. |
| A549 (Human Carcinoma) | | |
| Undiluted | 57 | 30 |
| 1/5 | 62 | 25 |
| 1/25 | 54 | 0 |
| 1/125 | 15 | 7 |
| Mink lung (CC1 64) | | |
| Undiluted | 91 | 43 |
| 1/5 | 90 | 13 |
| 1/25 | 70 | 9 |
| 1/125 | 31 | 2 |

One ml aliquots from gel filtration on fraction 5 (FIGS. 1 & 2) containing 120 micrograms were used to assay TGI activity.

High Performance Liquid Chromatography (HPLC)

Figure 4:
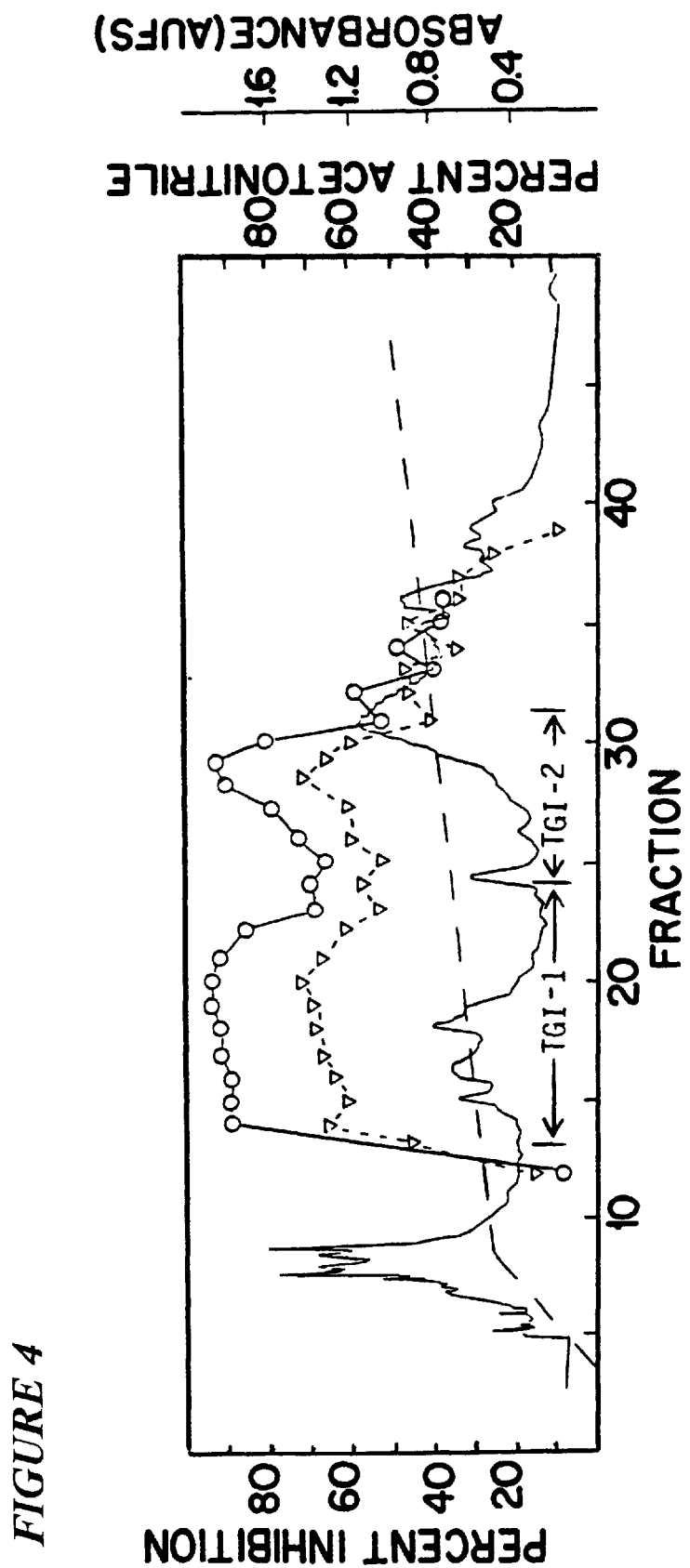
FIG. 4 shows reverse phase high performance liquid chromatography (HPLC) of an active fraction from gel filtration chromatography. Fraction 4 derived from gel filtration chromatography on Bio-Gel® P10 of human umbilical cord acidified, ethanol extract (65.8 mg protein) was lyophilized and resuspended in 10 ml of 0.05% trifluoroacetic acid (TFA). Fraction 4 was the first fraction following the major peaks of absorbance at 280 nm (FIG. 2). The sample was centrifuged on a Beckman table top centrifuge (Beckman TJ-6) at 3000 rpm for 20 minutes to remove insoluble material. Three separate injections of the supernatant were made through a Water's U6K injector equipped with a 2 ml sample loop. The sample was then loaded onto a μBOND-APAK® $C_{18}$ column (0.78×30 cm) (Waters #84176). The flow rate was 2 ml/min. and the effluent monitored at 206 nm (- - - - - - -) with a Waters u.v. detector (Waters Model 481) at a sensitivity of 2.0 AUPS. Elution was achieved with a linear 30 min gradient from 0–25% of increasing concentrations of acetonitrile containing 0.05% trifluoroacetic acid (TFA), followed by a linear 240 min gradient of 25–45% acetonitrile containing 0.05% TFA, followed by a linear 30 min gradient of 45–100% acetonitrile containing 0.05% TFA. A SuperRac® (LKB 2211) was used to collect 12 ml fractions. One ml aliquots of each fraction were transferred to 12×75 mm polystyrene tubes (Falcon 2058) containing 50 microliters of 1.0 M acetic acid and 50 micrograms of bovine serum albumin (Sigma A6003) and assayed for tumor growth inhibitory activity as described in Materials and Methods. Inhibition of A549 human lung carcinoma cells is shown by open triangles and of mink lung (CCL 64) by open circles. The solvent gradient is shown by large dashes (- - - - - - -).

TGIs from acid ethanol extracts of human umbilical cords partially purified by gel filtration on a Bio-Gel® P-10 column followed by further purification using reverse phase HPLC (μBONDAPAK® $C_{18}$ resin) inhibited the growth of both A549 human carcinoma and an established mink lung cell line, CCL 64, but did not inhibit the growth of normal human fibroblasts. FIG. 4 illustrates an elution profile of the tumor growth inhibitory activity obtained by HPLC using a linear acetonitrile gradient of lyophilized fraction 4 (19.8 mg/3 ml 0.05% trifluroacetic acid) derived from the Bio-Gel® P-10 chromatographic step.

Evidence of two distinct peaks of growth inhibitory activities against both the A549 human carcinoma and the mink cells were observed. The fractions eluting between 28–34% (fractions 13–22) acetonitrile and 35–39% (fractions 25–31) acetonitrile were pooled separately and rechromatographed on a $C_{18}$ μBONDAPAK® column using a linear gradient of 2-propanol.

Figure 5:
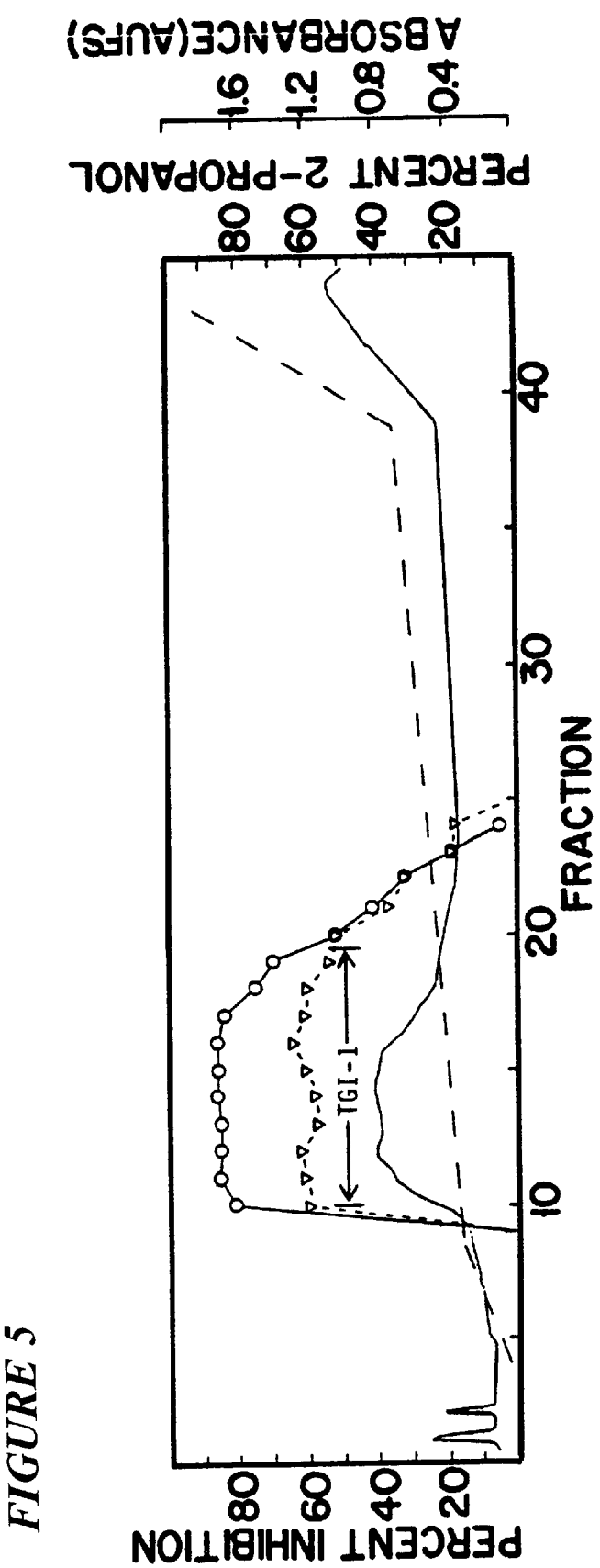
FIG. 5 shows HPLC rechromatography of pooled TGI activity from HPLC (TGI-1). Pooled fractions of tumor growth inhibitory activity (1.5 mg) eluting between 28–34% acetonitrile (fractions 13–22) by HPLC chromatography (FIG. 4) were lyophilized and resuspended in 2 ml of 0.05% trifluoroacetic acid (TFA). The sample was centrifuged on a Beckman table top centrifuge (Beckman TJ-6) at 3000 rpm for 20 minutes to remove insoluble material. Two separate injections of the supernatant were made through a Water's U6K injector equipped with a 2 ml sample loop. The sample was loaded onto a μBONDAPAK® $C_{18}$ column (0.39×30 cm) (waters #27324). The flow rate was 1 ml/min. and the effluent monitored at 206 nm (————) with a Waters u.v. detector (Waters Model 481) at a sensitivity of 2.0 AUFS. Elution was achieved with a linear 20 min gradient from 0–15% of increasing concentrations of 2-propanol containing 0.05% TFA, followed by a linear 120 min gradient of 15–35% 2-propanol containing 0.05% TFA. A SuperRac® (LKB 2211) was used to collect 4 ml fractions. One ml aliquots of each fraction were transferred to 12×75 mm polystyrene tubes (Falcon 2058) containing 50 microliters of 1.0 M acetic acid and 50 micrograms of bovine serum albumin (Sigma A-6003) and assayed for tumor growth inhibitory activity as described in Materials and Methods. Inhibition of A549 human lung carcinoma cells is shown by open triangles and of mink lung (CCL 64) cells by open circles. The solvent gradient is shown by large dashes (— — — —).
Figure 6:
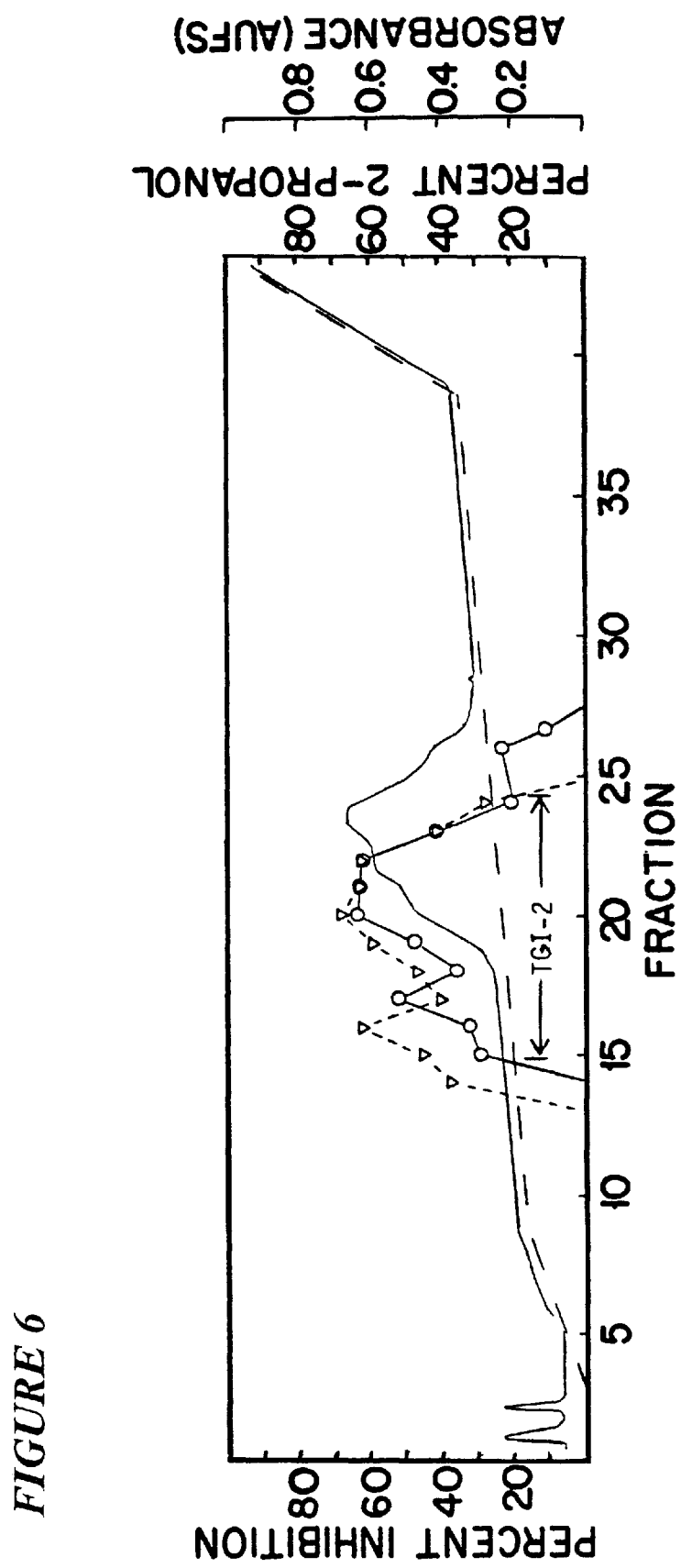
FIG. 6 shows reverse phase HPLC rechromatography of pooled activity from HPLC (TGI-2). Pooled fractions of tumor growth inhibitory activity (0.8 mg) eluting between 35–39% acetonitrile (fractions 25–31) by HPLC chromatography (FIG. 4) were lyophilized and resuspended in 2 ml of 0.05% trifluoroacetic acid (TFA). The sample was centrifuged on a Beckman tabletop centrifuge (Beckman TJ-6) at 3000 rpm for 30 min to remove insoluble material. Two separate injections of the supernatant were made through a Water's U6K injector equipped with a 2 ml sample loop. The sample was loaded onto a μBONDAPAK ® $C_{18}$ column (0.39×30 cm) (Waters 27324). The flow rate was 1 ml/min and the effluent monitored at 206 nm (————) with a Waters u.v. detector (Waters Model 481) at a sensitivity of 1.0 AUFS. Elution was achieved with a linear 20 min gradient from 0–15% of increasing concentrations of 2-propanol containing 0.05% TFA, followed by a linear 120 min gradient of 15–35% 2-propanol containing 0.05% TFA. A SuperRac® (LKB 2211) was used to collect 4 ml fractions. One ml aliquots of each fraction were transferred to 12×75 mm polystyrene tubes (Falcon 2058) containing 50 microliters of 1.0 M acetic acid and 50 micrograms of bovine serum albumin (Sigma A-6003) and assayed for tumor growth inhibitory activity as described in Materials and Methods. Inhibition of A549 human lung carcinoma cells is shown by open triangles and of mink lung (CCL 64) cells by open circles. The solvent gradient is shown by large dashes (————).

The first peak of tumor growth inhibitory activity was designated TGI-1 and the second TGI-2. FIG. 5 demonstrates the elution profile and tumor growth inhibitory activity of TGI-1 (FIG. 4). The concentration of injected material was 1.5 mg/1.5 ml of 0.05% trifluroacetic acid (TFA). TGI-1 activity elutes between 17–23% using a linear gradient of 2-propanol (FIG. 5). Similarly, FIG. 6 indicates that TGI-2 (0.8 mg/1.8 ml 0.05% TFA) rechromatographed between 23–27% (fraction 17–23) using a linear gradient of 2-propanol. The tumor growth inhibitory activity presented in FIGS. 4 and 5 are consistently 20% higher against the mink cells than against the A549 human carcinoma cells.

Acid ethanol extracts of human placenta contained TGI activities which, following a gel filtration chromatographic step, also eluted between 26–34% acetonitrile of a $C_{18}$ column using a linear acetonitrile gradient containing 0.05% TFA.

Ion Exchange Chromatography

Figure 7:
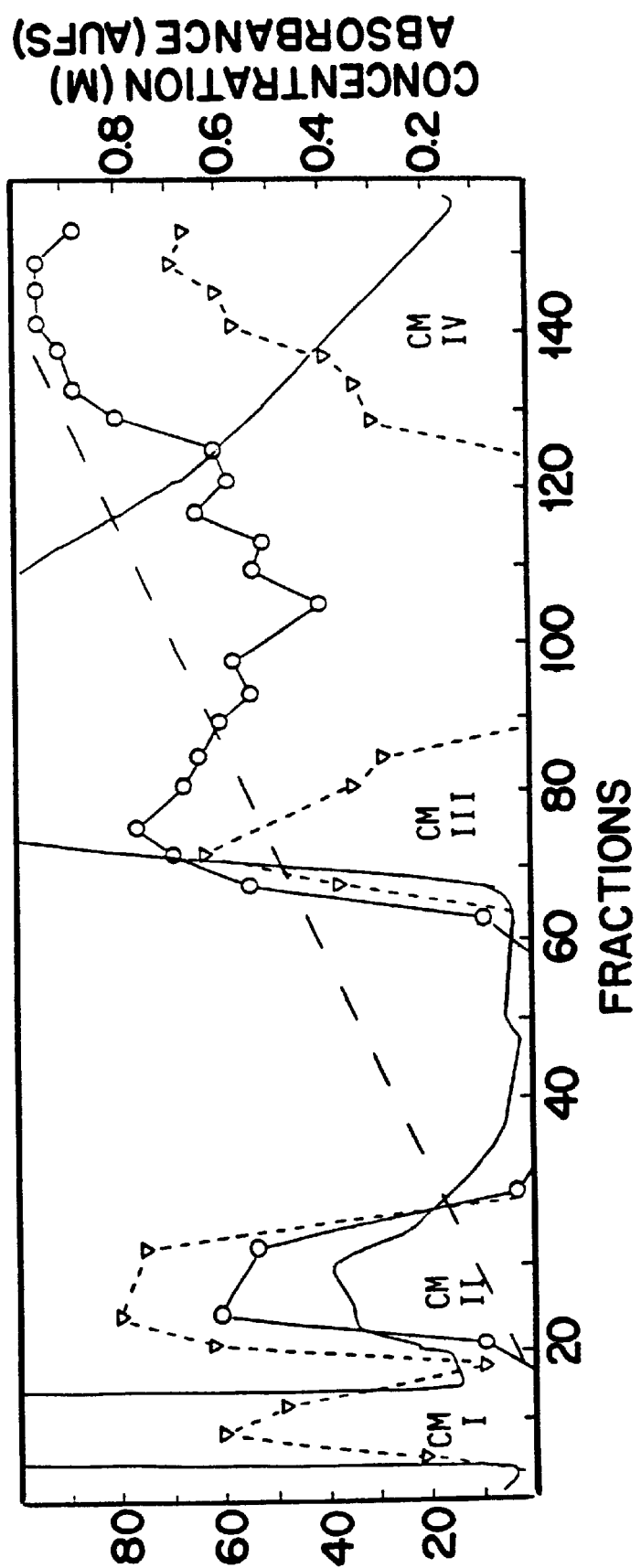
FIG. 7 shows cation exchange chromatography of human umbilical cord extracts. CM-TRISACRYL® was resuspended in an equal volume of 0.1 M ammonium acetate, pH 4.0, containing 1.0 M NaCl. The resin was allowed to equilibrate for 3 hours and degassed at 4° C. Twenty ml of resin was packed into a 1.6×40 cm column (Pharmacia; #19-0362-01) and washed with 2 column volumes of 1.0 M ammonium acetate pH 4.0, followed by 0.01 M ammonium acetate. The column was washed until the effluent matched the conductivity and the pH of the equilibrating buffer (0.01 M ammonium acetate pH 4.0). One gram of human umbilical cord acidified, ethanol extract was resuspended in 50 ml of 1.0 M acetic acid and dialyzed against the column equilibration buffer at 4° C. until the pH and the conductivity matched that of the equilibration buffer. The dialyzed acidified, ethanol extract was applied to the column at a flow rate of 1 ml/min at 4° C. and the column was washed with the equilibrating buffer until the absorbance (————), A280, as monitored by a Uvicord® S (LKB 2138) with a sensitivity of 1.0 AUFS, was at its lowest point. This was followed by 200 ml of an ascending molarity linear gradient from 0.01 to 1.0 M ammonium acetate, pH 4.0, which was applied using a gradient mixer (Pharmacia GM-1, #19-0495-01). At the end of the gradient, an additional 30 ml of 1.0 M ammonium acetate, pH 4.0, were passed through the column. Two ml fractions were collected in 12×100 mm polystyrene tubes (Columbia Diagnostics B-2564) in a SuperRac® fraction collector (LKB 2211). One ml aliquots from each fraction were transferred to 12×75 mm tubes (Falcon 2058) containing 50 microliters 1.0 M acetic acid and 50 micrograms bovine serum albumin (Sigma A6003), lyophilized, and assayed for tumor growth inhibitory activity as described in Materials and Methods. Inhibition of A549 human lung carcinoma cells is shown by open triangles and of mink lung (CCL 64) cells by open circles. The salt gradient is shown by large dashes (— — —).

One gram of a lyophilyzed acidified, ethanol extract of human umbilical cords was directly subjected to ion exchange chromatography on CM-TRISACRYL® in 0.01 M ammonium acetate, pH 4.0. A linear gradient was applied from 0.01 to 1.0 M ammonium acetate, pH 4.0. FIG. 7 demonstrates at least 4 separate tumor growth inhibitory activities designated CM-I, CM-II, CM-II, and CM-IV. CM-I was presently inhibited only the A549 human carcinoma cells at 60% inhibition (Table 2). CM peaks II and III have similar levels of growth inhibiting activity against both A549 human carcinoma (80 and 63%, respectively) and mink cells (61 and 76%, respectively). The last peak of activity (CM-IV) demonstrates a specificity in activity against mink (i.e. mink cells were more inhibited (95%) than were the A549 human carcinoma cells (69%)). CM-I was not retained and CM-II was slightly retarded by the negatively charged resin since they both were eluted before the gradient was started by 0.01 M ammonium acetate, pH 4.0.

Although all the proteins that have inhibitory activity are acidic proteins, since they are soluble at pH 4.0 and bind to a negatively charged resin, peaks CM-III and IV are probably slightly more basic since they bind more tightly to the CM-TRISACRYL® resin (eluting at greater than 0.5M ammonium acetate). This is substantiated by the fact that no TGI activity was retained by a

TABLE 2

TGI ACTIVITY FROM CATION EXCHANGE CHROMATOGRAPHY

| PEAK OF TGI ACTIVITY | PERCENT INHIBITION OF THE TEST CELL | |
|---|---|---|
| | A549 | Mink |
| CM I | 60 | 0 |
| CM II | 80 | 61 |
| CM III | 63 | 76 |
| CM IV | 69 | 95 |

Figure 10:
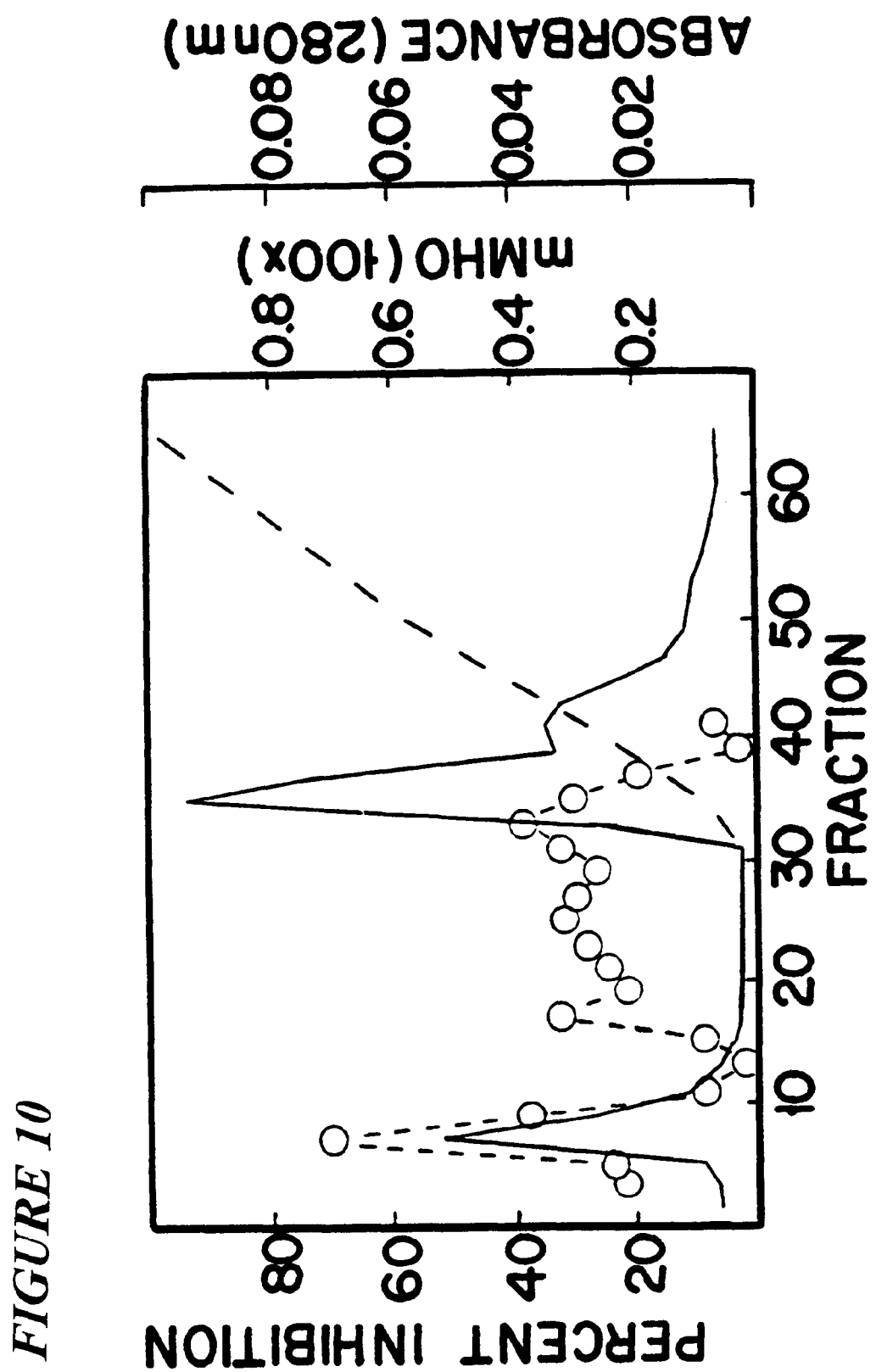
FIG. 10 shows the fractionation of TGI by anion exchange chromatography at 4° C. 1.65 mg of protein extract prepared as described in the Second Series of Experiments was dialyzed extensively against 20 mM Tris-HCl (pH 8.0) and clarified by centrifugation at 3,000×g for 15 minutes. DEAE-TRISACRYL® was prepared by suspending the resin first in 20 mM Tris-HCl (pH 8.0) containing 1.0 M NaCl for 3 hours and secondly in 0.5 M Tris-HCl (pH 8.0) for 1 hour. The sedimented resin was washed on a Buchner funnel with 1000 ml $H_2O$ and finally resuspended in 20 mM Tris-HCl (pH 8.0), degassed and poured into a 5 ml column (1×6.3 cm) and the resin equilibrated with 20 mM Tris, HCL (pH 8.0). The clarified sample was applied to the column and absorbance at 280 nm (————) inhibitory activity against mink lung cells (0—0), and the NaCl gradient (— — —) was determined as described in FIG. 9 and under Materials and Methods. The linear NaCl gradient in 20 mM Tris-HCl (pH 8.0) ranged from 0 to 1.0 M NaCl.

Protein concentrations for the fractions tested for TGI activity ranged from 15–300 μg. positively charged resin (i.e. DEAE-TRISACRYL®) (data not shown). The more acidic inhibitory factors appear to be more specific for the A549 human carcinoma cells in their respective activities. These 4 peaks of TGI activities (CM-I, CM-II, CM-III, and CM-IV) have been repeatedly observed (6 separate chromatographic procedures with CM-TRISACRYL®). To ensure that the tumor growth inhibitory activities observed in CM-III and CM-IV would not yield material that could be eluted earlier from the column, and also to provide support for the notion that each peak of activity is a separate entity, material from CM-III and CM-IV was pooled, lyophilized, and rechromatographed using CM-TRISACRYL® under the same conditions as the column from which it was derived. CM-III and CM-IV eluted (greater than 0.5 M ammonium acetate) in exactly the same position as did the original column fractions from which they were derived (FIG. 10). The higher tumor growth inhibitory inhibitory activity against mink cells was preserved and the difference between the inhibitory activity against the two cell lines remained exactly the same at 25–30% around the peak of activity.

Physical and Biological Characterization of Tissue Derived Tumor Cell Growth Inhibitory Activity (TGIs)

Fractions 2, 4 and 6 derived from gel filtration chromatography by. Bio-Gel® P-10 were either heat treated (Table 3). All fractions tested retained tumor growth inhibitory activity following either heat or acid treatment (see Table 4). Fractions 2, 4 and 6 were found to inhibit human cancer cell growth and stimulate normal human cell growth.

TABLE 3

EFFECT OF HEAT TREATMENT ON TGI ACTIVITY OF FRACTIONS FROM GEL FILTRATION CHROMATOGRAPHY

| | A549 | | MINK | |
|---|---|---|---|---|
| COLUMN FRACTION | CONTROL PERCENT INHIBITION | AFTER HEAT TREATMENT PERCENT INHIBITION | CONTROL PERCENT INHIBITION | AFTER HEAT TREATMENT PERCENT INHIBITION |
| 2 | 16 | 32 | 54 | 68 |
| 4 | 63 | 65 | 78 | 80 |
| 6 | 70 | 63 | 82 | 71 |

Protein concentrations for the fractions tested from TGI activity ranged from 15–300 μg.

TABLE 4

PHYSICAL AND BIOLOGICAL PROPERTIES OF TISSUE-DERIVED TUMOR CELL GROWTH INHIBITORY ACTIVITY (TGI)

| | Column Fraction | | |
|---|---|---|---|
| | Fraction 2 | Fraction 4 | Fraction 6 |
| Stable to 1.0 M acetic acid | + | + | + |
| Stable to boiling at 100° C. | + | + | + |
| Inhibits human cancer cells | + | + | + |
| Inhibits normal human cells | − | − | − |

Second Series of Experiments

Materials and Methods

Isolation of Tissue-Derived Tumor Growth Inhibitors (TGIS) from Tissue Extracts Depleted of Blood, Veins, and Arteries Veins and arteries were removed from human umbilical cord tissues and the remaining tissues were extensively washed to remove blood prior to acid/ethanol extraction as described under First Series of Experiments.

The buffer for washing and homogenizing the tissue (PBS-PA) consisted of 2 liters of water containing 16 gm NaCl, 2.5 gm $Na_2HPO_4.H_2O$, 0.4 gm $NaH_2PO_4.7H_2O$, 116 mg phenylmethylsulfonyl fluoride (PMSF) (Sigma P7627) and 3.3 ml Aprotinin (Sigma A6012 with 19.8 units Trypsin inhibitor per ml in 0.9% Nacl and 0.9% benzyl alcohol), adjusted to pH 7.4 with HCl and NaOH. The extraction buffer consisted of 375 ml, of 95% (v/v) ethanol (punctilious, 190 proof, U.S. Industrial Chemicals, #UN1170), 7.5 ml of concentrated HCl, 33 mg of phenylmethylsulfonyl fluoride (PMSF) (Sigma P-7627) and 1 ml of Aprotinin (Sigma A6012) mixed with 192 ml of distilled water at 4° C. Eight hundred to one thousand grams of frozen human umbilical cords (Advanced Biotechnologies®; stored at −80° C.) were thawed by immersion in PBS-PA for two hours at 4° C. Individual umbilical cords were removed and rinsed with PBS-PA. Veins and arteries were removed from the umbilical cords by dissection at 4° C. The dissected umbilical cord was washed with fresh PBS-PA to remove residual blood and vascular debris.

The tissue was placed in a 4° C. chilled Cuisinart food processor (Model DLC-7-PRO) and suspended in 200 ml of 4° C. PBS-PA. The suspended tissue was homogenized by the food processor. After the first minute of homogenization, an additional 200 ml of 4° C. PBS-PA was added. The tissue suspension was homogenized for a total of 10 min. at 4° C. The homogenate was transferred to 200 ml centrifuge bottles (Sorvall) and centrifuged at 9000 rpm (RCF=13,000) for 5 minutes at 4° C. in a Sorvall RC5B centrifuge equipped with a Sorvall GSA rotor. The supernatant fluid was removed and discarded and the pellet resuspended to the original homogenate volume with fresh PBS-PA.

The pellet was washed by repeated centrifugation and resuspension as described until the supernatant fluid was clear with no tint of red from contaminating blood or blood products. The resulting washed pellet was white. The washed pellet was resuspended in the buffer for extraction to a final volume of 6 ml per gram of original dissected tissue. The homogenate was transferred to a large 4 liter beaker with a 3 inch stir bar and stirred at half of the maximum stirring capacity of a LAB-line Multimagnestir® multimixer, Model #1278. After overnight extraction with stirring at 4° C., the homogenate was transferred to 1 liter centrifuge bottles (Sorvall) and centrifuged at 3500 rpm (RCF=3570) for 30 minutes at 4° C. in a Sorvall RC-3B centrifuge equipped with a Sorvall H-6000A rotor. The supernatant was transferred to a large 4 liter beaker and adjusted to pH 5.0 with the slow addition of concentrated ammonium hydroxide. With increasing pH, the supernatant remained clear with a slight yellowish tint. A 2.0 M solution of ammonium acetate, pH 5.2, was added in an amount 1% of the total volume. Any precipitate formed by this step was removed by centrifugation at 4500 rpm (RCF=5900) for 4 hours in a Sorvall® RC-3B at 4° C. The supernatant was transferred to large 6 liter flasks to which four volumes of anhydrous ether (−20° C) (Baker #9244-3) and two volumes of 95% ethanol (4° C.) were added. The mixture was allowed to stand undisturbed at −20° C. for 48 hours to allow the resulting precipitate to settle.

At the end of the 48 hr precipitation, the material was brought to ambient temperature in a fumehood. Warming of the acidified, ethanol extract to ambient temperature enhances the aggregation of the precipitate. The clear organic phase of ether and ethanol was removed by a water aspirator and the precipitate remained in the fume hood for several hours to allow the residual organic phase to evaporate. A gentle stream of dried nitrogen gas over the extract accelerated the evaporation of the remaining organic solvent present with the precipitate. The "dried" precipitate was dissolved in 1.0 M acetic acid and dialyzed extensively against 1.0 M acetic acid (Baker #9507-5) using dialysis membranes with a molecular weight cutoff of 3500 (Spectropor 3®, Spectrum Medical Industries, Los Angeles, Calif.). The dialyzed acidified extract was lyophilized in 250 ml Corning conical centrifuge tubes (Corning 25350) and stored as crude acidified, ethanol extract or dialyzed extensively against 20 mM $NH_4O_2C_2H_3$, pH 4.5.

Comparison of tumor growth inhibitory activity in the initial acid/ethanol extract from tissue prepared as described in the First Series of Experiments with tissue prepared as described above.

The improvement in the specific activity and total recovered activity seen when the tissue was prepared as described above is shown in Table 5. The table compares the yields of protein and tumor growth inhibitory activity from frozen umbilical cord when it was processed according to the procedures detailed in the First Series of Experiment (hereinafter "initial procedure") and when it was processed as describe above (hereinafter "modified procedure").

There are several obvious differences in the two procedures which are of importance for the subsequent purification of TGI. For example, based on the wet weight of the tissue, acidified ethanol extraction by the initial procedure resulted in the recovery of 0.33% as protein (3.3 g from 1000 g tissue) whereas only 0.015% as protein (0.05 g from 340 g tissue) was extracted when following the modified procedure. Because the yield of activity was 50% greater ($3.3 \times 10^6$ units) by the modified procedure than in the initial procedure ($2 \times 10^6$ units) from 66% less tissue (340 g vs 1000 g) the overall efficiency of extraction was improved. The initial procedure yielded 2000 units of tumor growth inhibitory activity per gram of umbilical cord (wet weight). The modified procedure yielded 9700 units of tumor growth inhibitory activity per gram of umbilical cord (wet weight).

The overall efficiency of extraction was improved 5-fold by the modified procedure. Furthermore, since less protein was extracted by acidified ethanol, the volumes of ether and ethanol

TABLE 5

Comparison of Tumor Growth Inhibitory Activity in the Initial Acid/Ethanol Extract from Tissue Prepared as Described in the Initial Procedure with that Prepared as Described in the Modified Procedure

| Tissue[1] (wet weight) | Procedure | Protein (extracted) | Total[2] Activity | Specific[2] Activity |
|---|---|---|---|---|
| 1000 g | initial | 3.0 g | $2 \times 10^6$ u | 0.67 u/µg protein |
| 340 g | modified | 50 mg | $3 \times 10^6$ u | 67 u/µg protein |

[1]Human umbilical cord
[2]A unit of activity is defined as that amount of material which results in 50% of the maximal inhibition seen with a given cell line, e.g., the A549 (as used for this table) cell line is maximally inhibited 60%, therefore a unit of activity is equivalent to 30% inhibition.

required to precipitate the extracted proteins are less. Finally, the amounts of protein and the numbers of different proteins extracted by the modified procedure are fewer and therefore the subsequent purification procedures to be employed will require less chromatographic materials, shorter processing times and fewer steps to obtain a pure product.

Figure 8:
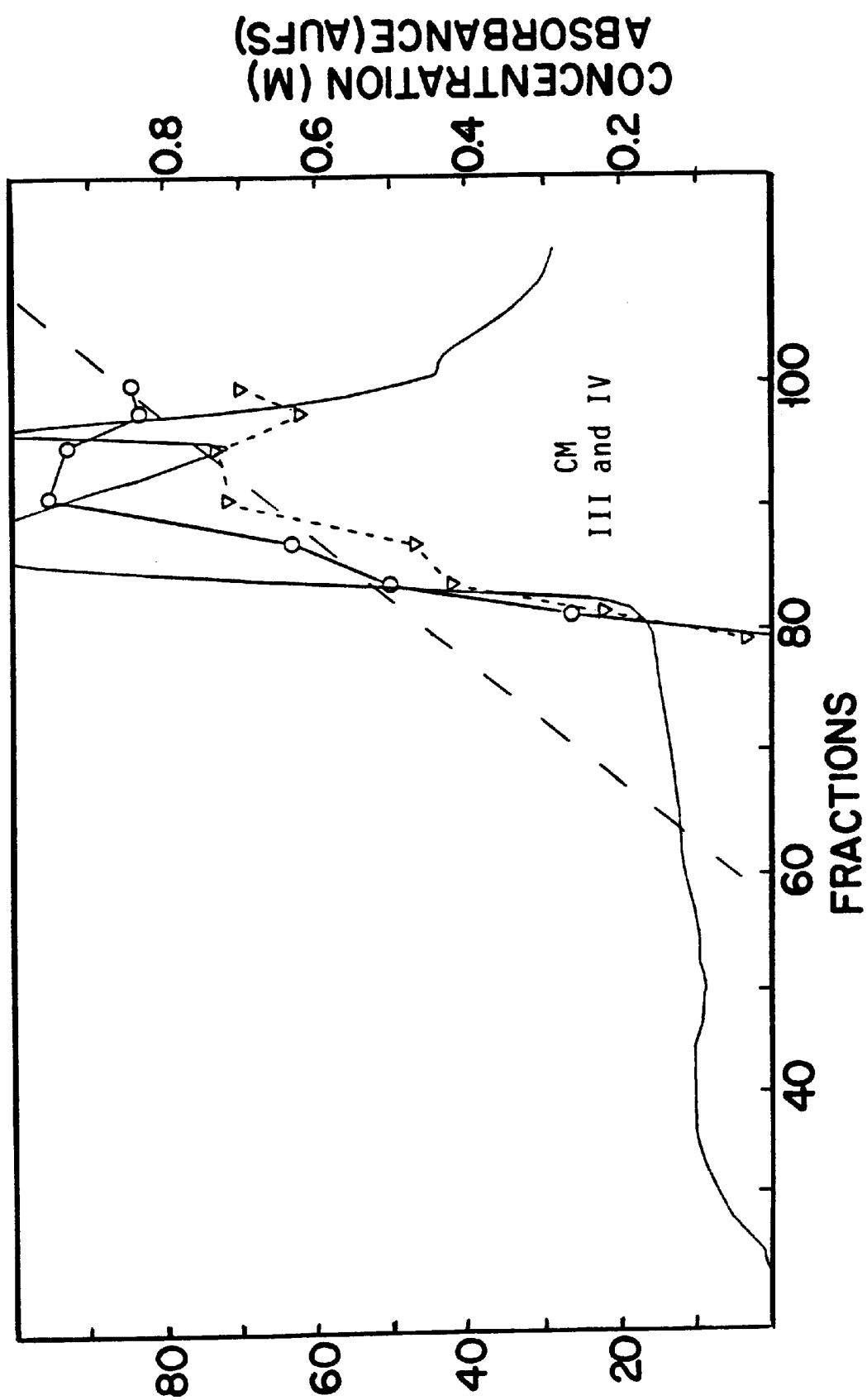
FIG. 8 shows rechromatography of a pooled fraction from cation exchange chromatography. CM-TRISACRYL® was prepared as described in FIG. 9. The material from fractions containing CM III and CM IV were pooled, lyophilized, resuspended in 50 ml of 0.1 M acetic acid and dialyzed against the column equilibration buffer at 4° C. until the pH and the conductivity matched that of the equilibration buffer. The sample was applied to the column at a flow rate of 1 ml/min at 4° C. and the column was washed with 120 ml of the equilibrating buffer. Absorbance (————) (280 nm) was monitored by a Uvicord S (LKB 2138) with a sensitivity of 1.0 AUFS. One hundred ml of an ascending molarity linear gradient from 0.01 to 1.0 M ammonium acetate, pH 4.0, was applied using a gradient mixer (Pharmacia; GM-1, #19-0495-01). At the end of the gradient, an additional 30 ml of 1.0 M ammonium acetate, pH 4.0, was passed through the column. Two ml fractions were collected in 12×100 mm polystyrene tubes (Columbia Diagnostics B2564) in a SuperRac® fraction collector (LKB 2211). One ml aliquots from each fraction were transferred to 12×75 mm tubes (Falcon 2058) containing 50 microliters 1.0 M acetic acid and 50 micrograms bovine serum albumin (Sigma A6003), lyophilized, and assayed for tumor growth inhibitory activity as described in Materials and Methods. Inhibition of A549 human lung carcinoma cells is shown by open triangles and mink lung (CCL 64) cells by open circles. The salt gradient is shown by large dashes (— — —).
Figure 9:
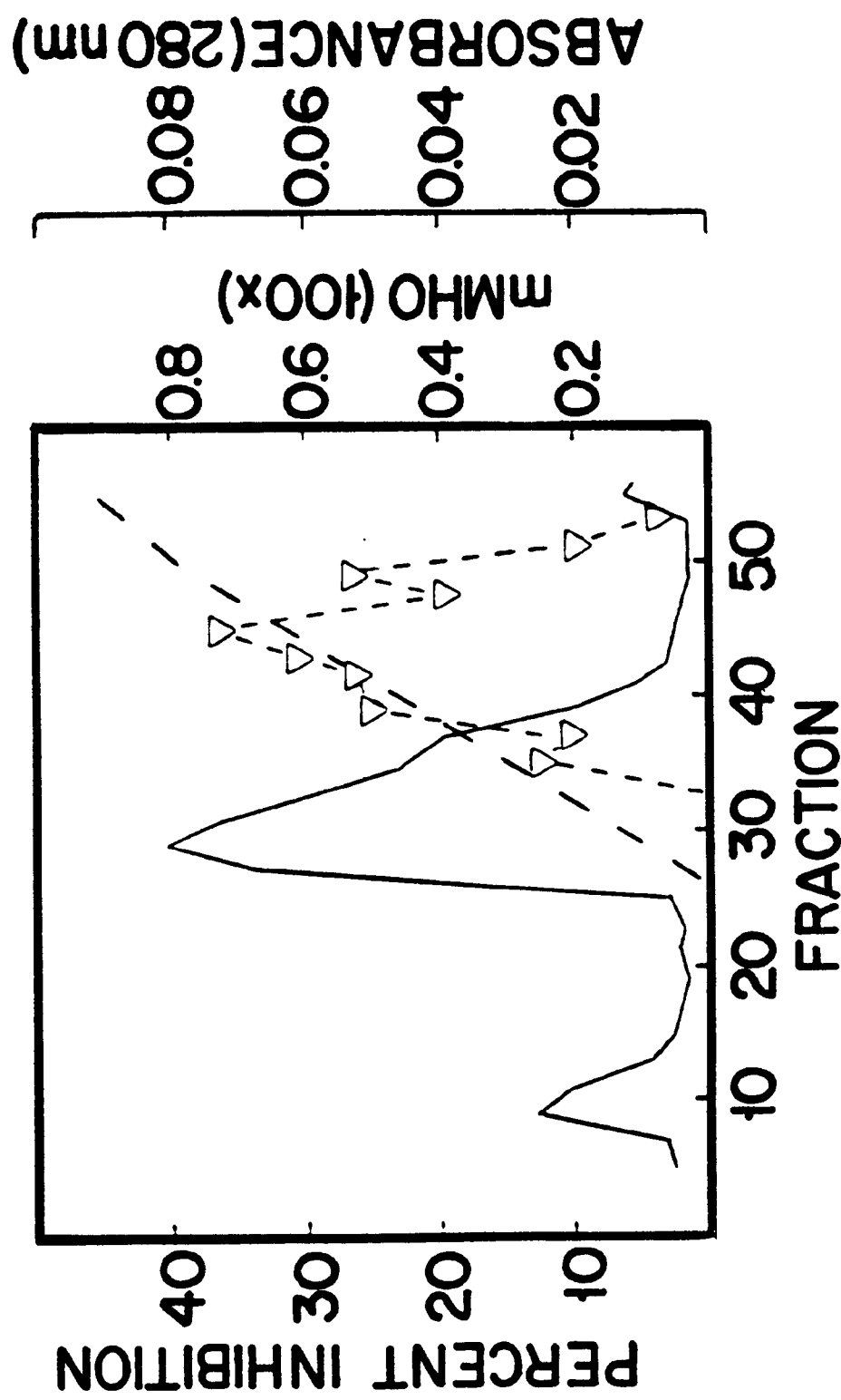
FIG. 9 shows the fractionation of TGI by cation exchange chromatography at 4° C. 1.65 mg of protein extract prepared as described in the Second Series of Experiments was dialyzed extensively against 20 mM ammonium acetate (pH 4.5) and applied to a 5 ml (1×6.3 cm) column of CM-TRISACRYL® previously equilibrated in 20 mM ammonium acetate (pH 4.5) and 1.65 ml fractions (12×100 mm polystyrene tubes) were collected. Following sample application, the column was washed with 20 mM ammonium acetate, pH 4.5, until the absorbance at 280 nm (-) returned to baseline values (less than 0.003) as determined with a Bausch and Lomb 1001 spectrophotometer using a 1 cm light path quartz cuvet. A linear salt gradient (0–1.0 M NaCl in 20 mM ammonium acetate, pH 4.5) was applied and the absorbance at 280 nm of the 1.65 ml fractions was determined as described above. 10 microliter aliquots of the indicated fractions were transferred to 12×75 mm tubes containing 50 ul 1.0 M acetic acid and 50 micrograms bovine serum albumin (Sigma A6003), lyophilized, and assayed for inhibitory activity (▽ - - - ▽) against A549 human lung carcinoma cells as described under Materials and Methods. The NaCl gradient (— — —) was determined by measuring the conductivity (YSI Model 32 Conductance Meter) of suitable samples diluted 100-fold in $H_2O$.

Fractionation of TGI extracted using the modified procedure on the cation exchange resin CM-TRISACRYL® was resolved as a single peak from the bulk of the applied protein when the bound material was eluted by a linear salt gradient from 0–1.0 M NaCl. FIG. 9 shows that following application of TGI to a CM-TRISACRYL® column no inhibitory activity was detectable from material not bound to the resin (i.e., fractions 1–24). The linear addition of increasing amounts of NaCl (- -) removed the majority of protein bound to the resin (fractions 25–38) prior to the removal of significant amounts of inhibitory activity (- - - - -) fractions 39–49). The NaCl concentration most effective in removing bound TGI was approximately 0.6 M (fraction 44). Comparison of FIG. 9 with FIG. 8 suggests that the inhibitory activity eluted in the experiment of FIG. 9 most closely corresponds to the elution of CM-III and CM-IV from the CM-TRISACRYL® resin as depicted in FIG. 7 since the salt concentrations (NaCl, FIG. 9; $NH_4O_2$—$C_2H_3$ FIG. 8) for elution are similar (0.6 M, FIG. 11; 0.6–0.7 M, FIG. 8). The above information also suggests that treatment of the tissue by the modified procedure allows the preferential isolation of a single peak of TGI, thus improving subsequent characterization of the factor.

Another property of the TGI extracted from the tissue by the modified procedure is its failure to bind to anion exchange resin. FIG. 10 shows that following adjustment of the pH to 8.0 as described in the figure legend and application of the extract (an identical amount to that used in FIG. 9) to the anion exchange resin DEAE-TRISACRYL® resulted in the majority of inhibitory activity associating with nonbinding material (fractions 1–30), whereas the bulk of the applied protein (as determined by absorbance at 280 nm, (--------) bound to the column resin. These results show that under the conditions of FIG. 10, contaminating proteins can be removed from TGI and, therefore, that it is a useful procedure for purification of TGI. In addition, these results show that at pH 8.0, TGI is a cation since it does not bind the anion exchange resin. Finally, the results of FIG. 10 show that TGI as extracted by the modified procedure is similar in ionic character to those polypeptides (TGI-1, TGI-2, CM-I, CM-II, CM-III and CM-IV) extracted by ion exchange resin in the initial procedure since none of these bound to the anion exchange resin.

Figure 11:
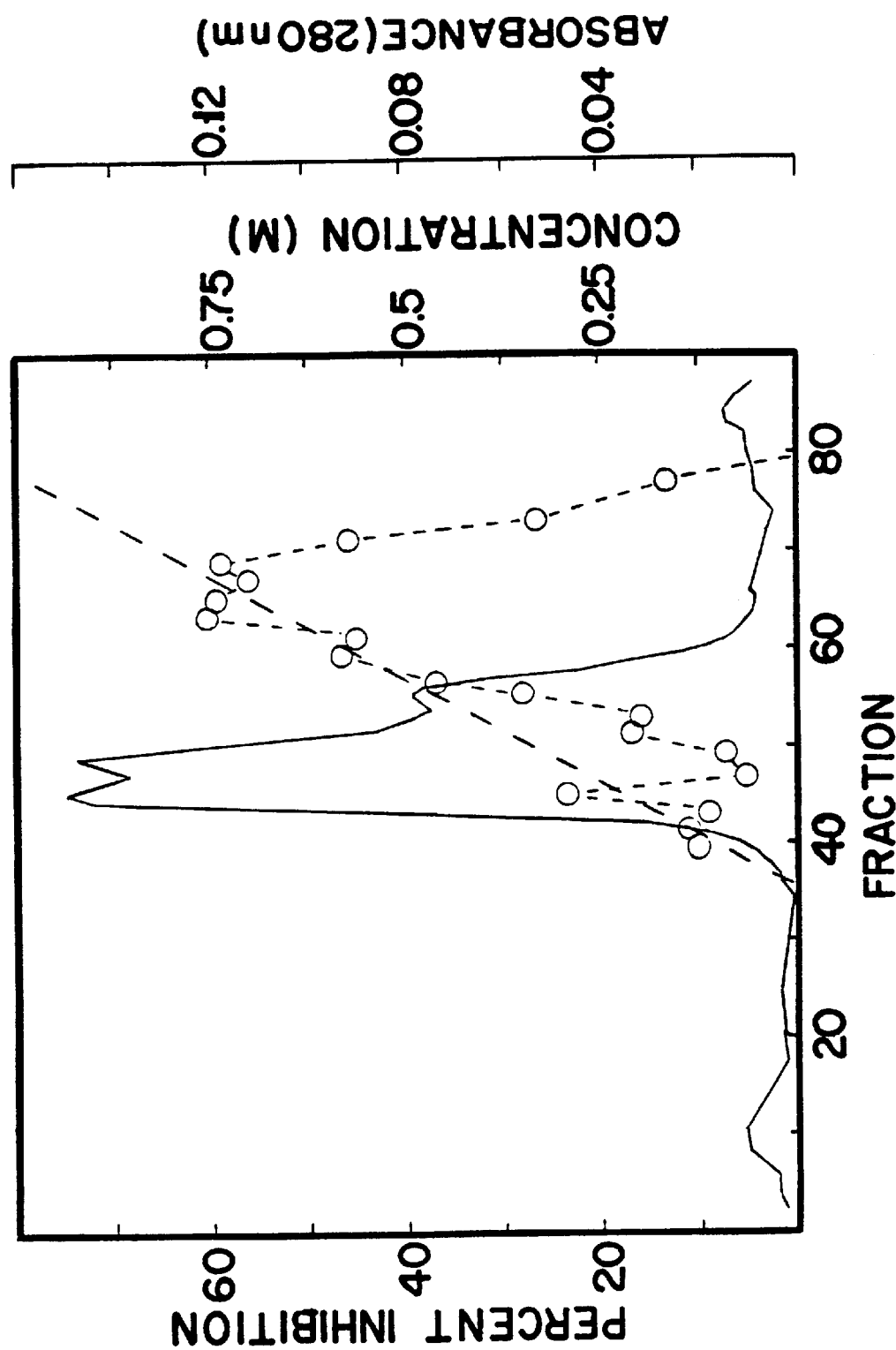
FIG. 11 shows the fractionation of TGI by cation exchange chromatography at 4° C. CM-TRISACRYL® was prepared as described in FIG. 7 with the exception that the final equilibration buffer was 20 mM ammonium acetate, pH 4.5. Protein extract (9.9 mg) prepared as above was dialyzed extensively against 20 mM ammonium acetate (pH 4.5) and applied to a 15 ml (1.5×8.5 cm) column of CM-TRISACRYL® in 20 mM ammonium acetate (pH 4.5). Absorbance at 280 nM (-) and inhibitory activity (-o- -o- -) against A549 human lung carcinoma cells were determined as described in FIG. 7. The volume of the linear 0–1.0 M NaCl gradient was 150 ml. Volume of each fraction was 3.7 ml.

Large amounts of sample can be reproducibly fractionated by CM-TRISACRYL®, thus furnishing more TGI for subsequent purification procedures. In FIG. 11, 9.9 mg of tissue extract were applied to a CM-TRISACRYL® column (15 ml) under the same chromatographic conditions as shown in FIG. 10 for a smaller sample size (2.65 mg protein) on a smaller CM-TRISACRYL® column (5 ml). Resolution of tumor growth inhibitory activity from the majority of proteinaceous material by a linear gradient of NaCl was essentially the same in both experiments.

Figure 12:
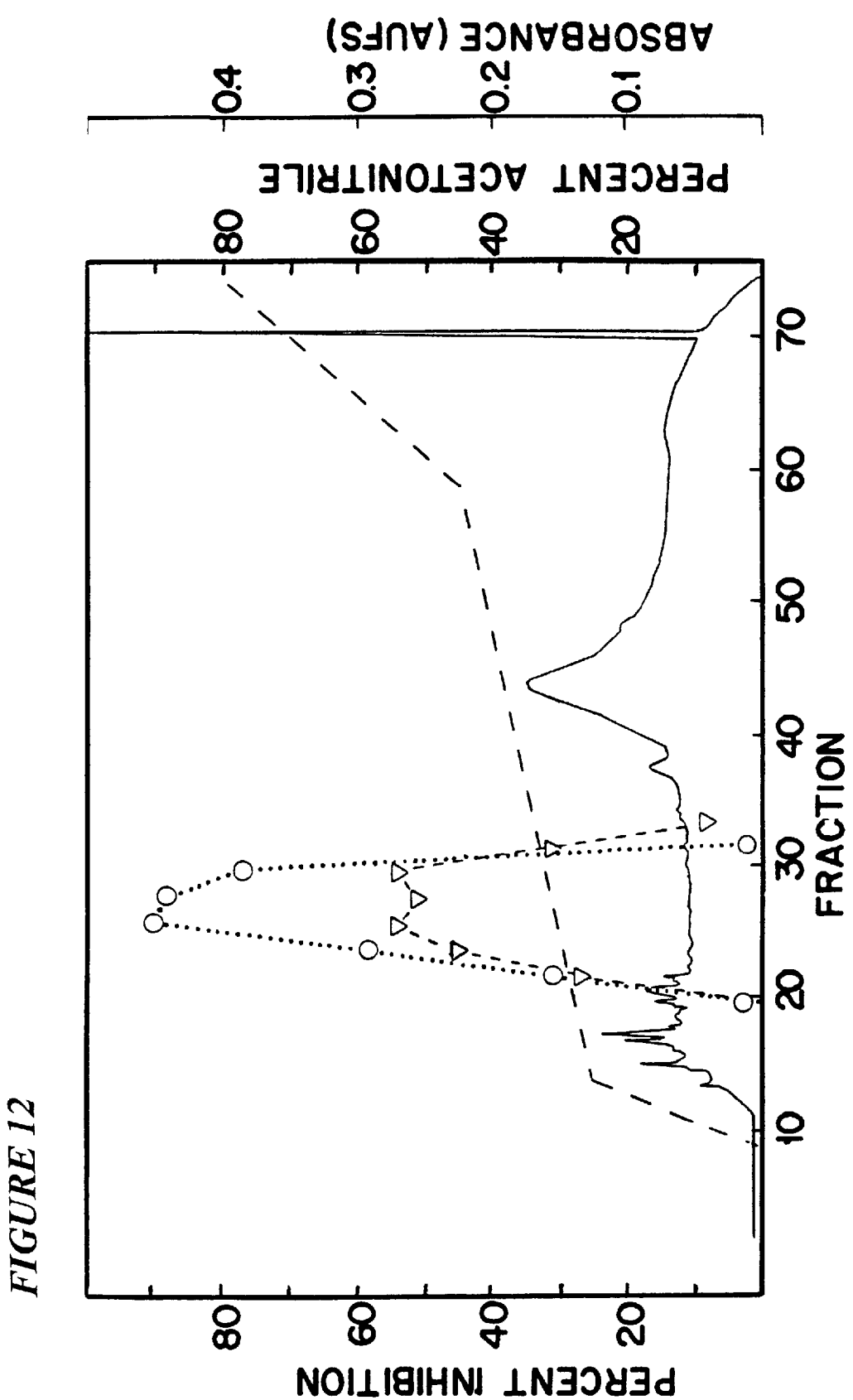
FIG. 12 shows the reverse phase high performance liquid chromatography (HPLC) of active fractions from cation exchange chromatography. Fractions 59 thru 78 derived from cation exchange chromatography on CM-TRISACRYL® of human umbilical cord described in FIG. 11 were pooled, lyophilized, and resuspended in 10 ml of 0.05% trifluoracetic acid (TFA). A total of twenty percent of dialyzed material containing 240 micrograms protein was injected in three separate injections through a Water's U6K injector equipped with a 2 ml sample loop. The sample was then applied onto a $\mu$BOND-APAK® $C_{18}$ column (0.39×30 cm) (Waters 27324). The flow rate was 1 ml/min and the effluent was monitored at 206 nm (————) with a Waters u.v. detector (Waters Model 481) at a sensitivity of 0.5 AUFS. Elution was achieved with a linear 5 min gradient from 0–25% of increasing concentrations of acetonitrile containing 0.05% TFA, followed by a linear 15 min gradient of 25–45% acetonitrile containing 0.05% TFA, followed by a linear 15 min gradient of 45–80% acetonitrile containing 0.05% TFA, followed by a linear 5 min gradient of 80–100% acetonitrile containing 0.05% TFA. A Super-Rac® (LKB 2211) was used to collect 1 ml fractions. Five hundred microliter aliquots of every other fraction were transferred to 12×75 mm polystyrene tubes (Falcon 2058) containing 50 microliters of 1.0 M acetic acid and 50 micrograms of bovine serum albumin (Sigma A0281) and assayed for tumor growth inhibitory activity as described under Materials and Methods. Inhibition of A549 human lung carcinoma cells is shown by open triangles and of mink lung (CCL 64) cells by open circles. The solvent gradient is shown by large dashes (— — —).

FIG. 12 shows fractionation of pooled samples from a CM-TRISACRYL column by HPLC on a µBONDAPAK® C18 column. Following application of the sample, no significant inhibitory activity was observed by linearly increasing acetonitrile concentrations from 0–25%. However, tumor growth inhibitory activity against both A549 (human lung carcinoma) and CCL 64 (mink lung, 0-0) eluted in a single peak between 28–34% acetonitrile (fractions 21–31) while the majority of material absorbing at 206 nm was eluted at lower (fractions 11–19) and at higher (fractions 37–50) acetonitrile concentrations.

An apparent molecular weight of TGI (termed TGI-1 and CM-III and. CM-IV in the initial procedure) was determined by gel filtration chromatography (Sephadex G-50, data not shown) using suitable protein standards of known molecular weights. Thus, in the absence of certain interfering proteins (e.g., hemoglobin) the apparent molecular weight of TGI has been determined to be between 20 kDa and 30 kDa under nondenaturing conditions.

The modified procedure detailed herein describes a powerful and simple procedure for removing inert or interfering compounds from the TGI extracts prepared as described in the initial procedure. Furthermore, the modified procedure improves the efficacy of the various chromatographic steps employed in the isolation of TGI by reducing the amount of chromatographic materials required thus reducing the preparation time of TGI. In addition, and as shown, extraction of TGI from the umbilical cord as described herein allows TGI and other proteins to chromatograph more reproducibly than in the procedure previously described.

TGI isolated according to the modified procedure has been characterized with respect to the chromatographic features on both reverse phase high performance liquid chromatography and CM-TRISACRYL® ion exchange chromatography. TGI has been found to behave similarly to or identically with TGI-1 (compare FIGS. 5 and 12) by RPHPLC, and thus has similar or identical hydrophobic properties and is shown also to behave similarly to or identically with CM-III and CM-IV (compare FIGS. 9 and 11) on a cation exchange resin, thus having similar or identical ionic properties. It is therefore concluded that TGI as isolated in the modified procedure and TGI-1 and CM-III and CM-IV are similar or identical compounds having similar or identical ionic and hydrophobic properties and thus are of similar or identical composition. Therefore, the modified procedure described herein provides a more efficacious method of obtaining a purer form of TGI for further analysis and characterization.

Third Series of Experiments

Materials and Methods

Acidified Ethanol Extraction and Ether/Ethanol Precipitation

The buffers and equipment used were exactly as described in the second series of experiments, for each relevant step in the procedure. Two hundred to four hundred grams (200–400 gr.) of human umbilical cord, either dissected free of vasculature or left intact and chopped into ½ inch pieces were washed free of the majority of blood in PBS-PA at 4° C. The cord was drained by gravity through a sieve and transferred to a chilled food processor at 4° C. for homogenization in a maximum volume of 200 ml of PBS-PA. The tissue was homogenized for fifteen minutes and washed free of blood by repeated centrifugation in 200 ml plastic bottles at 5,000 rpm using an RC-5B centrifuge (Sorvall) equipped with a GSA rotor (Sorvall) for ten minutes with PBS-PA, until the optical. density at 280 nm was less than 0.05 and the pellet obtained, was essentially white in color. The pellet was transferred to a 2 liter glass beaker and suspended in extraction buffer, as described in the first series of experiments, at a final volume of 3 ml per gram of the original wet weight of tissue and stirred for twenty-four hours at 4° C. The suspension was centrifuged in a 1.0 liter plastic centrifuge bottle using a RC-3B centrifuge (Sorvall) equipped with a H6000A rotor (Sorvall) for 30 minutes at 3,500 rpm. The resulting supernatant was transferred to a 2 liter beaker and the pH adjusted first to 5.0 with concentrated ammonium hydroxide, and then to 5.2 by the addition of 2 M ammonium acetate to a final concentration of 1% of the total volume. The solution retained a clear or very slightly yellow tinted appearance.

Following ether/ethanol precipitation, as described previously, the supernatant was siphoned from the flask to within ¾ of an inch above the bottom of the flask containing the flocculent precipitate. The precipitate and remaining ether/ethanol solution was centrifuged in a GSA rotor at 5,000 rpm for 20 minutes in 250 ml plastic conical bottles (Corning #25350) in a Sorvall RC-5B centrifuge. This step in the procedure was designed to decrease the loss of TGI's from the ether/ethanol supernatants immediately above the precipitate. The resulting pellet was suspended in 1.0 M acetic acid and the flask containing the ether/ethanol precipitate was also washed with 1.0 M acetic acid to remove any TGI protein remaining on the wall of the flask. The optical density at 280 nm was between 0.5 and 1.0 and the final volume did not exceed 100 ml for each preparation. The TGI containing protein solution was dialyzed for one day against 1.0 M acetic acid and for one to two days against two changes of 4.0 M ammonium acetate, pH 4.5 using dialysis membranes with a molecular weight cutoff of 3,500 (Spectropor 3).

It should be noted that tumor growth inhibitory activity can also be obtained from acidified ethanol extraction of the tissue with omission of the ether-ethanol precipitation step. However, the specific activity of these preparations is 50% less and the total yield of activity 10–30% less than "standard" preparation utilizing the ether-ethanol precipitation.

Hydrophobic Interaction Chromatography

The dialyzed protein was subjected to hydrophobic interaction chromatography using phenyl-Sepharose® (Pharmacia) as the chromatographic resin. The phenyl-Sepharose® was equilibrated with 4.0 M ammonium acetate, pH 4.5. Following dialysis (at least 24 to 48 hours), the conductivity and pH of the protein solution was measured and dialysis terminated when the conductivity of the dialysate and equilibration buffer were the same. The protein was pumped onto (Microperplex® pump #2132-LKB) the resin contained in a 1.6×2.0 cm chromatography column (K-20-Pharmacia) using 1 ml of resin per 2.0 mg of protein, at 1.0 ml per minute. The column was washed until the $OD_{280}$ was zero and tumor growth inhibitory activity eluted from the column using a decreasing gradient from 4.0 M to 0.04 M ammonium acetate, pH. 4.5 containing an increasing concentration of ethylene glycol (Mallinkrodt) from 0 to 50%. The total volume of the eluting gradient was 10 times the total volume of the resin used for each individual preparation. The bound protein was eluted over approximately fifty fractions. Ten microliters of sample were transferred to a plastic tube (polystyrene) containing 50 micrograms of BSA, for assay of inhibitory activity against both the mink CCL 64 and A549 cell lines, as described in the first series of experiments.

Figure 13:
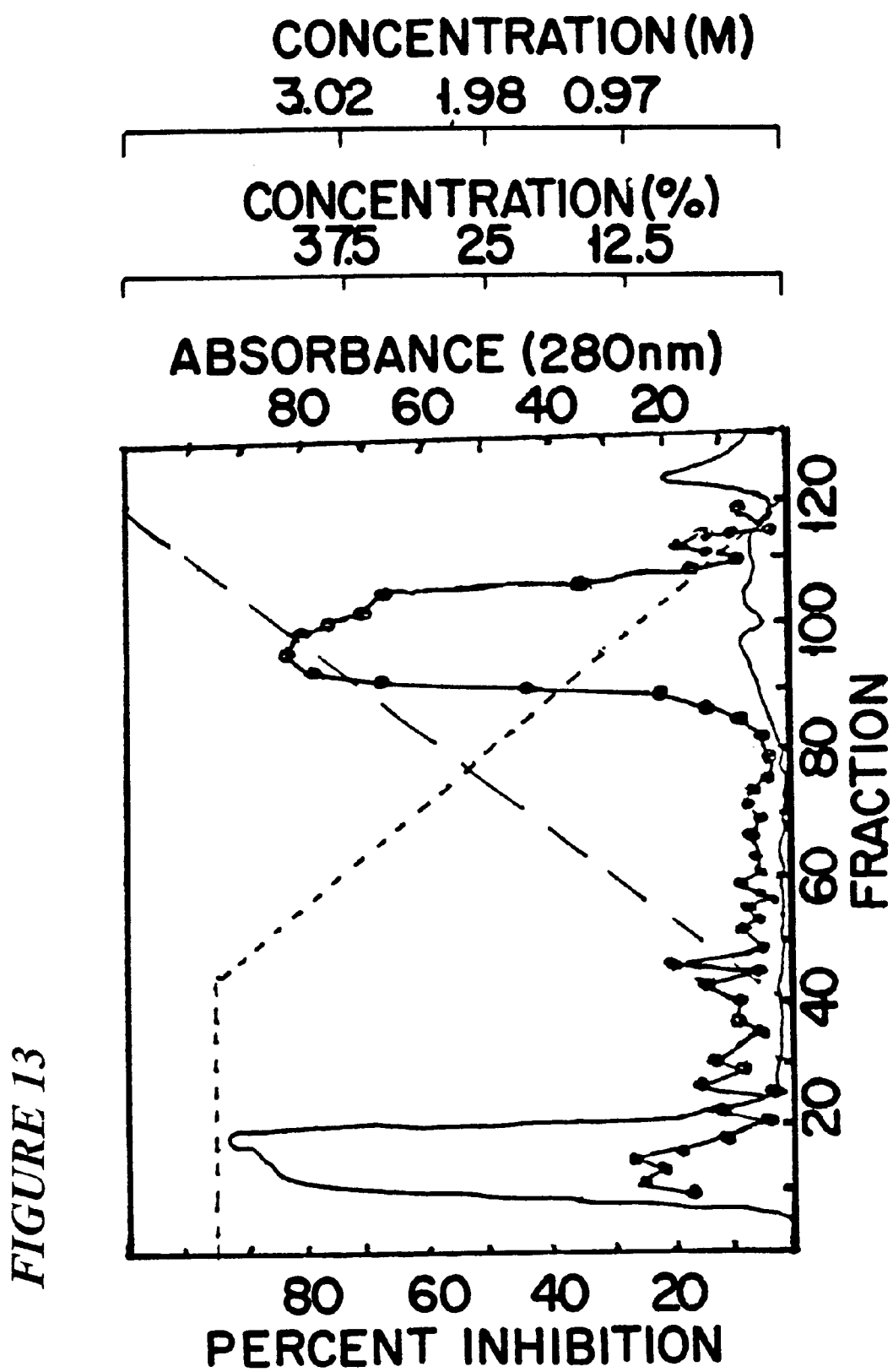
FIG. 13 shows the hydrophobic interaction chromatography phenyl-Sepharose. Phenyl-Sepharose (Pharmacia) was equilibrated with 4.0 M ammonium acetate, pH 4.5 and 15 ml of resin poured into a 1.5×20cm column (Pharmacia). Thirty-one mg of ether ethanol precipitated TGI in 36.0 ml which was equilibrated by dialysis in Spectropor® 3 (molecular weight cutoff 3,500) in 4.0 M ammonium acetate, was applied to the column at a flow rate of 1.0 ml/min. After the absorbance at $OD_{280}$ reached zero, a gradient containing a descending concentration of 4.0 M to 0.04 M ammonium acetate (short broken lines) and an ascending concentration of ethylene glycol (Mallinkrodt) from 0–50% (long broken lines), pH 4.5 was applied through a flow adaptor (Pharmacia AC16). The total volume of the gradient was 150 ml and 1.9 ml fractions were collected by a Redirac® fraction collector (LKB). Thirty microliters of every other fraction was transferred to a sterile plastic 12×75 mm snap-top tubes (Falcon) containing 50 micrograms of bovine serum albumin (Sigma A0281) in 1.0 M acetic acid. Tumor growth inhibitory activity was determined for both CCL 64 mink lung cells and A549 cells as described in the initial procedure. Activity against A549 cells is not shown because the activity profiles were similar. Tumor growth inhibitory activity is plotted as percent inhibition and is illustrated by closed circles. The peak of growth inhibitory activity was eluted at 1.18 M ammonium acetate, 42% ethylene glycol. Protein concentration is indicated as absorbance at 280 nm and was determined using a spectrophotometer (Baush & Lomb, Spectronic® 1001).

As seen in FIG. 13, the tumor growth inhibitory activity began eluting from the column at 1.5 M ammonium acetate, 31% ethylene glycol and was completely eluted from the column by 40 mM ammonium acetate and 50% ethylene glycol. The biologically active fractions were pooled, dialyzed against 0.1 M acetic acid, and lyophilized in a polypropylene 50 ml tube (Scientific Products #C2390-50) or siliconized glass lyophilization flask (Virtis).

Reverse Phase High Pressure Liquid Chromatography

The lyophilized biologically active material was diluted in 1.0 to 3.0 ml of 0.05% trifluoracetic acid (TFA) containing 10% acetonitrile, placed in a 16×100 mm siliconized disposable glass tube, sonicated for two minutes, centrifuged at 3,000 rpm for 10 minutes (Beckman Model TJ-6) to remove insoluble material, and subjected to reverse phase, high pressure liquid chromatography (RPHPLC) using a μBondapak® C18 resin (Waters Assoc. 0.39×30 cm, PN 27324). No more than 1 mg of TGI was applied to each column such that the number of column procedures necessary for each preparation depended on the total protein concentration of the active fraction obtained following chromatography by phenyl-Sepharose. This amount was approximated at $OD_{280}$ using a value of 1.0 optical density units equal to 1.0 mg/ml of protein. The protein was eluted from the column, at 1.0 ml per minute in a stepwise, gradient fashion using 100% acetonitrile containing 0.05% TFA as the eluting mobile phase. The gradient was increased to 25% acetonitrile ($CH_3CN$) in 15 minutes, eluted for 10 minutes at 25% ($CH_3CN$), increased to 27% in two minutes, 17% for 10 minutes, increased to 28% in two minutes, 28% for 10 minutes, increased to 30% over 10 minutes, resulting to 44% in 10 minutes, and to 100% in 10 minutes. The absorbance of protein was monitored at 210 nm and 0.005 ml aliquots were removed from every other 1.0 ml fraction to assay for tumor growth inhibitory activity against both CCL 64 and A549 cell lines. Tumor growth inhibitory activity eluted initially at 27% acetonitrile and continued to elute at 28–30% acetonitrile as shown in FIGS. 14A & 14B. At every step in the purification, the biologically active fractions were pooled and subsequently assayed for total tumor growth inhibitory activity by removing an aliquot and multiplying the activity obtained in the assay by the appropriate dilution factor. The quantity of tumor growth inhibitory activity present in the pool was compared to an aliquot of starting material. Thus, column recoveries of activity and protein (where measurable) could be obtained.

The area designated with arrows (fractions 47–51) in FIG. 14A derived from two separate C18 chromatographic procedures (derived from one phenyl-sepharose column, from one isolation) was pooled and subjected to SDS-PAGE both under non-reducing conditions (FIG. 15A) and in the presence of 0.5% β-Mercaptoethanol (reducing conditions) (FIG. 15B). This area of the chromatogram (FIG. 14A) demonstrated the highest biological activity and lowest amount of contaminating proteins (highest specific activity and lowest absorbance at 210 nm). Experimental details of SDS-PAGE are reported in FIG. 15. In lane 2, under non-reducing conditions (FIG. 15A), the biologically active fractions are shown to contain at least 4 major proteins bands. Lane 1 contains a purified preparation of TGF-β derived from platelets (provided by Bruce Magun, Oregon State Health Science University, Portland, Oreg.). The biological activity that has been ascribed to this protein is the ability to confer anchorage independent growth to normal rat kidney cells (NRK) in a soft agar assay, only in the presence of a growth factor, such as EGF at 2.0–2.5 ng/ml. Thus, its growth promoting activity is directly dependent on other bioactive proteins (Roberts et al., Cold Spring Harbor Conf. Cell Proliferation, 9: 319–332 (1982)); Anzano et al., Anal. Biochem. 125: 217–224 (1982); Cancer Research 42: 4776–4778 (1982).

In our assay for tumor growth inhibitory activity, TGF-β was shown to posses 1–30 units of inhibitory activity per ng of protein. By comparison it appears that one of the protein bands in the TGI preparation FIG. 15A (lane 2) also migrated in the same position of approximately $M_r$=25 kDa as the TGF-β, (lane 1). The same samples electrophoresed in the presence of 5% β-mercaptoethanol, showed that the protein band that had migrated at $M_r$ 26 kDa disappeared and a new band was evident at approximately 12.5 kDa FIG. 15B (lane 2). TGF-β FIG. 15B (lane 1 also changed its migratory position to 13 kDa following reduction. All other proteins in the TGI containing sample remained in the same position of migration and thus were insensitive to reduction. The units of inhibitory activity applied to the gel for each sample was approximately 1,000–1,500 (50 ng) for TGF-β in lane 1 and 10,000 to 20,000 for TGI in lane 2 (FIGS. 15A & B).

Further purification of the TGI biologically active fractions derived from the RPHPLC C18 chromatographic procedure was accomplished by RPHPLC using a CN μBONDAPAK® column (0.39×30 cm Waters PN 84042) (FIG. 16). The biologically active fractions were lyophilized in 16×100 mm siliconized glass tubes, dissolved in 1.0–3.0 ml 0.05% TFA containing 10% propanol and applied to the column. Column elution was achieved at 1.0 ml/minute by using a linear gradient of 2-propanol from 10 to 20% in ten minutes, followed by 20 to 50% in fifteen minutes (0.6%/min.), and finally from 50–100% in 20 minutes.

Iodination of Biologically Active Fractions for Analysis by SDS-PAGE

Active, lyophilized fractions 56, 58, 59–65, 66–68, illustrated in FIG. 18, and approximately 4 ng of TGF-β were iodinated by the chloramine T method (McConahey, P. J. and Dixon, F. J. (1966) Int. Arch. of Allergy 29, 185–189). Each fraction was resuspended in 100 microliters of 0.1 M acetic acid, and 3 microliters of 1.5 M Tris, pH 8.8 was added to adjust the pH to 7.0. Ten microcuries of carrier-free sodium iodide $I^{125}$ Na was added, followed by 2 microliters of chloramine T (Sigman #C9887) at 1.0 mg/ml. The tube was rocked for one minute and the reaction terminated by the addition of 2 microliters of sodium metabisulfite (Sigma #S9000) at 1.0 mg/ml. After two minutes 0.05 ml of each sample was transferred to a siliconized glass tube (10×75 mm) containing 0.05 ml of twice concentrated sample buffer plus 5% β-mercaptoethanol for SDS-PAGE slab gel electrophoresis.

The remainder of the sample was diluted in 0.05 ml of twice concentrated sample buffer and approximately 200, 000 TCA precipitable radioactive counts were applied to individual lanes for SDS-PAGE, FIG. 17). The gel was stained with 0.125% Coomassie Blue for 10 minutes to fix the protein in the gel, and exhaustively destained to remove free radioactive iodine. When the destain solution did not contain detectable label as judged by counting 1.0 ml of destain solution in a gamma counter (Beckman, Riagamma #1294), the gel was dried using a gel dryer (Hoeffer-SE1150) and exposed to x-ray film (Kodak-XAR) for autoradiography (one week).

All lanes to which biologically active TGI was added contained a faint band of protein migrating at $M_r$ 24 kDA. This protein band also migrated directly in a horizontal plane with the $M_r$ 26 kDa band in lane 7 containing 256 inhibitory units of TGF-β derived from platelets (FIG. 17, lane 7 arrow).

In lanes 1, 2, 3 and 5 containing approximately 180, 2,000, 46 and 408 units of tumor growth inhibitory activity respectively, the $M_r$ 25 kDa band was observed while lanes 4 and 6, which did not possess tumor growth inhibitory activity, did not contain this protein band. Lane 2, which contained the most active fractions (from FIG. 16), showed two faint bands at $M_r$ 26 kDa and 30 kDa. Lane 3 appears to have only one band of $M_r$ 26 kDa.

Following the last step of purification of TGI, protein concentration could not be measured because it was below the detection level using standard means of measurement. Therefore, the bands migrating at $M_r$ 26 kDa (from lanes 2, 3 and 7) were excised from the dried gel and counted in a gamma counter in order to extrapolate the protein concentrations applied in lanes 2 and 3. Since it was known that 0.4 ng of TGF-β was applied to the gel which had 5,593 cpm at $M_r$ 26 kDa, then 362 (lane 2) and 195 (lane 3) cpm at the position of 26 kDa equals 26pg and 14pg, respectively. These calculations assume that the number of tyrosines and extent of iodination of each tyorsine were the same.

Although the presence of the $M_r$ 26 kDa band was consistent with the presence of tumor growth inhibitory activity (FIG. 17), the quantity (units) of activity, especially in lane 2, did not correlate with the amount of TGF-β protein, as judged by the intensity of iodinated protein applied to the gel (0.4 ng). Thus, TGI demonstrated at least one log more inhibitory activity than TGF-β.

Since a broad peak of activity was obtained by RPHPLC C18® chromatography, FIG. 14A; and in FIG. 14B it appeared that there may be two peaks of activity, one at 27% and at 28–30%, the area designated by these separate peaks were pooled and chromatographed separately by RPHPLC using a CN column. The slope of the propanol gradient was changed so that the increase in increments of 2-propanol was 0.375% per minute, instead of 0.6% per minute. The shallow gradient was devised to achieve a better separation of active proteins eluting between 40–45% 2-propanol.

FIG. 18 illustrates the elution profile of the CN column of active fractions pooled at 27% acetonitrile (Pool I) from the previous C18 column. The most active fraction (fraction #14) eluted at 40–41% 2-propanol. A lower amount of activity was seen eluting after this peak, as a double peak at approximately 44% 2-propanol. Similarly, rechromatography of the active material derived from the peak of activity pooled at 28–30% acetonitrile (Pool II) from the C18 column, demonstrated peak of activity corresponding to the elution from the CN column at 44% 2-propanol (FIG. 19). The first pool (Pool I) of activity eluting at 27% acetonitrile contained some active material from Pool II eluting at 28–30% acetonitrile, thus a small quantity of this peak of activity was revealed in the chromatogram of Pool I at 40–41% 2-propanol (FIG. 18). Most significantly the further purification of TGI has permitted resolution of two major peaks of TGI activity, eluting at 40–41% for Pool I and 44% for Pool II.

Pool I from the C18 column contained 82% more total inhibitory activity than Pool II.

FIG. 20 is a tracing of the peaks of activity from the two separate chromatographs FIGS. 20 (Pool I), and 21 (Pool II). This FIG. 20 illustrates two distinct peaks of inhibitory activity as the different active fractions from the C18 column Pool I and Pool II.

It was found that preservation of TGI biological activity following chromatography through the C18 column was better achieved if the active fractions were not lyophilized prior to CN chromatography. Therefore, the samples were concentrated by partial lyophilization (not to completion) and stored at −20° C.

II. Tumor Growth Inhibitory Activity from the Conditioned Media of Various Tumor Cell Lines

Effect of Dithiothreitol on TGI Activity from Tumor Cell Conditioned Media

Human tumor A431 (epidermoid carcinoma), A673 (rhabdomyosarcoma) and T24 (bladder carcinoma) cells were grown to confluence on T150 (150 cm$^2$) flasks in 20 ml of complete growth medium containing DMEM supplemented with 10% fetal bovine serum. The confluent monolayers were rinsed twice with Dulbecco's phosphate buffered saline and incubated in 10–12 ml serum-free DMEM per flask for 24 h. Conditioned media (100–115 ml) was collected from 1–4×10$^8$ cells.

An erythroleukemia cell line, K562, was grown in suspension to a cell density of 10$^6$ cells per ml and one liter of serum-free conditioned media was collected. Cellular debris was removed from the conditioned media (RC-5B GSA rotor-Sorvall) by centrifugation at 800 rpm for 60 min. at 4° C. The supernatant was treated with 1 ml of 1 M acetic acid per 100 ml of conditioned media, extensively dialyzed in Spectropor 3 dialysis tubing (Spectrum Medical Laboratories) against multiple changes of 1 M acetic acid, and lyophilized. The lyophilized, acid-treated conditioned media was resuspended in 4 mm HCl at a volume of 5.0 ml for A431, A673 and T24, and 1.5 ml for K562 derived media. Insoluble material was removed by centrifugation in a RC-5B centrifuge (Sorvall, SA 600 rotor) at 3400 rpm for 15 min. at 4° C. and the supernatants transferred to 1.5 ml microfuge tubes. Following centrifugation in an Eppendorf microfuge for 15 min. at 4° C., the supernatants were transferred to 1.5 ml microfuge tubes for storage at −20° C. Protein concentration was determined by absorbance at 280 nm. The tumor growth inhibitory activity of individual samples was tested for sensitivity to reduction by dithiothreitol (DTT). An aliquot each of 0.5 ml was transferred to two tubes containing 4.5 ml of 0.1 M NH$_4$HCO$_3$. One tube received a final concentration of 65 mM DTT, and both tubes were incubated for 2 hours at room temperature. The incubated mixture was then transferred to Spectropor 6 dialysis tubing and dialyzed against 1 M acetic acid for 2 days to remove DTT. The dialyzed samples were then assayed for tumor growth inhibitory activity as described in initial procedures. The effect of DTT on TGI activity derived from conditioned media from the A431, A673, K562 and T24 cell lines using mink cells, CCL 64, and A549 cells as target cells is summarized in Tables 6 and 7, respectively. The table shows the tumor growth inhibitory activity from conditioned media from A673, K562, and T24 against both mink and A549 cells was lost following reduction (Table 6), whereas the tumor growth inhibitory activity from the conditioned media of A431 cells, which showed preferential inhibitory activity against A549 cell, was only slightly reduced following reduction (First column, Table 7).

TABLE 6

EFFECT OF DITHIOTHREITOL (DTT) ON TUMOR GROWTH INHIBITORY ACTIVITY FROM TUMOR CELL CONDITIONED MEDIA USING MINK TARGET CELLS$_1$

| Protein | A431 | | A673 | | K562 | | T24 | |
|---|---|---|---|---|---|---|---|---|
| | PERCENT INHIBITION (%) | | | | | | | |
| μg | −DTT | +DTT | −DTT | +DTT | −DTT | −DTT | +DTT | −DTT |
| 61.8 | 95 | 28 | 95 | 21 | 88 | 13 | 94 | 12 |
| 12.4 | 93 | 19 | 95 | 0 | 91 | 14 | 93 | 21 |
| 2.5 | 70 | 11 | 94 | 0 | 92 | 18 | 92 | 15 |
| 0.5 | 26 | 11 | 87 | 14 | 86 | 0 | 92 | 7 |
| 0.1 | 29 | 6 | 50 | 0 | 49 | 12 | 75 | 1 |

$_1$Conditioned media from A431, A673, K562 and T24 cells was treated with 65 mM dithiothreitol (DTT) and tested for tumor growth inhibitory activity against target cells compared to control.

TABLE 7

EFFECT OF DITHIOTHREITOL ON TUMOR GROWTH
INHIBITORY ACTIVITY FROM TUMOR CELL CONDITIONED
MEDIA USING A549 TARGET CELLS

PERCENT INHIBITION (%)

| Protein | A431 | | A673 | | K562 | | T24 | |
|---|---|---|---|---|---|---|---|---|
| µg | −DTT | +DTT | −DTT | +DTT | −DTT | +DTT | −DTT | +DTT |
| 61.8 | 75 | 45 | 71 | 8 | 74 | 12 | 79 | 28 |
| 12.4 | 69 | 56 | 70 | 2 | 71 | 2 | 77 | 11 |
| 2.5 | 49 | 42 | 58 | 4 | 61 | 0 | 76 | 20 |
| 0.5 | 28 | 35 | 34 | 0 | 36 | 9 | 60 | 2 |
| 0.1 | 10 | 10 | 7 | 1 | 14 | 0 | 47 | 5 |

1 Conditioned media from A431, A673, K562 and T24 cells was treated with 65 mM dithiothreitol (DTT) and tested for tumor growth inhibitory activity against A549 compared to control.

Reverse Phase HPLC of A431 Conditioned Media

Lyophilized conditioned media from $4 \times 10^8$ A431 cells (110 ml) was processed as previously described, except 5.0 ml of 4 mM HCl was used to solubilize the lyophilized material. The insoluble precipitate was removed by centrifugation as described and protein concentration determined. An aliquot of 0.2 ml (680 µg protein) was added to 1.8 ml of 0.1 M ammonium bicarbonate or this same buffer containing 65 mM DTT. Following incubation for 2 hours at room temperature, both the reduced and non-reduced samples were lyophilized and resuspended in 2.0 ml of 0.05% trifluoroacetic (TFA) for RPHPLC. Following injection onto a C18 semipreparative column, the proteins were eluted at 1.0 ml per minute using a linear gradient of acetonitrile from 0–50% in 50 minutes. An aliquot of 1.0 ml was removed from each 2.0 ml fraction to assay for growth inhibitory activity against both mink and A549 cell lines as described in the initial procedures. FIG. 21 illustrates that there are two peaks of inhibitory activity, one that elutes at 25% acetonitrile, which inhibits both CCL 64 and A549 cells, and one that elutes at 30–36% acetonitrile, which shows preferential inhibitory activity toward the A549 cell line. Following DTT treatment (FIG. 22), the first peak of activity (25% acetonitrile) is no longer present, while the activity that is selective for A549 cells retained activity.

Conclusions from the "Third Series of Experiments"

I. It was already demonstrated by the Second Series of Experiments referred to as the "modification procedure" that removal of blood and vasculature from umbilical cord yielded approximately a 100-fold increase in specific activity of the TGI over First Series of Experiments (Table 5). In the Third Series of Experiments, referred to as "alternate procedure", it was shown that only removal of blood, but not the vasculature was necessary to obtain TGI with the same average degree of specific activity as indicated by the Second Series of Experiments. In fact, the vascular tissue from umbilical cord, dissected free form the stromal tissue, demonstrated tumor growth inhibitory activity of similar to the umbilical stromal tissue alone (data not shown). It was further shown that tumor growth inhibitory activity could be recovered without ether/ethanol precipitation of the extracted material.

The volume of acidified ethanol per gram of tissue used for extraction was 50% less than described for both the initial procedure and modified procedure. Thus, the total volume of extracted protein was less, therefore requiring ½ the amount of ether and ethanol used for precipitation. This minimized the amount of protein that would remain on the flask walls. Moreover, the amount of 1.0 M acetic acid necessary to dissolve the precipitate and wash the flask was smaller so that final volumes were kept to a minimum. The obvious advantage is the minimization of protein/activity loss, thereby creating a more efficient method of extraction, including less reagents required. Also, chopping whole cord rather than dissecting cord shortened the tedious preparation time considerably. The average specific activity of the final preparation derived from 200–400 grams of umbilical cord (wet weight) prior to further purification by chromatographic techniques was approximately $1–3.0 \times 10^6$ units/40–50 mg (see Table 8).

TABLE 8

SUMMARY OF PURIFICATION OF TGI FROM UMBILICAL CORD

| | Step | Protein (mg) | Units | Units/mg | Fold | % Recovery Units |
|---|---|---|---|---|---|---|
| 1. | ether/ethanol* precipitate | 20–50 | $1–3 \times 10^6$ | $5 \times 10^4$ | 1 | 100 |
| 2. | phenol Sepharose | 1–3 | $1–5 \times 10^6$ | $1–2 \times 10^6$ | 20–40 | 100 |
| 3. | RPHPLC-C18 | 0.02 | $0.2–2.3 \times 10^6$ | $1–2 \times 10^9$*** | $2–4 \times 10^4$ | 60–100 |
| 4. | RPHPLC-CN | N.D.** | $0.05–1.5 \times 10^6$ | $0.1–1 \times 10^{10}$*** | $2–4 \times 10^6$ | 1–10 |

*from 200–400 gr. wet tissue
**N.D., not detectable
***estimated because protein concentrations were undetectable These results are within the range of the experimental results reported for the "modified procedure" and therefore, represent the same range of improvement in protein recoveries and specific activities compared to the initial procedure (Table 5). Thus, the overall efficiency of extraction was improved approximately 5-fold as reported in the "modified procedure".

Table 8 summarizes the current procedure utilized to obtain active TGI from human umbilical cord. Between 60 to 100% recovery of units of activity was observed through the first two steps of purification (HIC and RPHPLC on C18). This represents a 40,000 increase in specific activity of $1.\times10^6$ units/microgram. ($2.3\times10^6$ total units from 300 g wet umbilical cord). It was observed that contaminating proteins probably aided in the stabilization of biological activity of TGI, because as the purification ensued, activity became more labile. The greatest loss of recovery occurred following lyophilization of the active fraction obtained after RPHPLC on the C18 column. This greatly reduced the total number of units applied to the CN column in the final step of purification. This loss was ameliorated by concentrating the active fractions by lyophilization, but not to completion. The recovery of units from this final step of purification was between 60–100%.

Previously in the "initial procedure", chromatograms varied foremost of the preparations, thus, causing difficulty in devising subsequent steps for improvement. The current methodology described in both the modified and alternate procedure demonstrate reproducibility of all chromatograms, yields of proteins, and yields of activity at each step, utilizing material derived from individual umbilical cord preparations. This improvement is a direct result of the removal of hemoglobin (denatured), before acidified, ethanol extraction, and the more efficient removal of other contaminating proteins during the first chromatographic step using phenyl-Sepharose.

The use of hydrophobic interaction chromatography (HIC) using phenyl-Sepharose as the first chromatographic step in the purification procedure proved to be a major improvement in overall yield of activity (total units) and specific activity (units/mg). Following ion exchange chromatography by CM-Trisacryl®, a specific activity of $4.2\times 10^4$ units per mg was obtained, while phenyl-Sepharose chromatography produced TGI with a specific activity of $1.07\times10^6$ u/mg. At this step, phenyl-Sepharose chromatography introduced approximately a 20-fold purification into the procedure. However, the TGI containing protein obtained by phenyl-Sepharose chromatography demonstrated 26 times greater specific activity than TGI containing material derived from CM-Trisacryl chromatography.

Experiments have been devised to improve the overall yield (inhibitory units) and specific activity of the TGI-containing protein so that there would be adequate biologically active material present to subject the protein to as many steps necessary for purification to homogeneity. Both the removal of blood in the "modification procedure" and the use of phenyl-Sepharose chromatography in the "alternate procedure" have aided greatly in accomplishment of this goal. The introduction of phenyl-Sepharose chromatography into the purification procedure has provided material with higher specific activity ($1-2\times10^6$ units/microgram) which permitted further purification of a minimal amount of starting material (wet tissue weight) and requiring less steps toward the final purification to homogeneity. One peak of TGI activity, eluting at 1.5 M ammonium acetate, 37% ethylene glycol, was obtained following phenyl-Sepharose chromatography (FIG. 13). This was also a major improvement in the isolation of TGI in the "modification procedure" using CM Trisacryl®, compared to the initial procedure (FIG. 7).

Another improvement introduced into the purification of TGI's by the "alternate procedure" was the use of a stepwise elution by acetonitrile from C18 RPHHPLC (FIG. 14A & 14B) rather than a linear gradient used in the "initial and modification procedures" (FIG. 12). Elution of the column in this fashion allows approximately 90% of the biologically inactive contaminants to be separated from the major peak of activity. Of most significance is that two hundred to four hundred grams of wet cord material provides sufficiently less protein following chromatography on phenyl-Sepharose, to apply the entire preparation to a maximum of three and a minimum of two RPHPLC C18 and analytical columns using no more than 1.0 mg for each (FIG. 14A.& 14B).

The ability to obtain larger quantities of a more highly purified biologically active protein following RPHPLC on a C18 resin is directly related to the isolation of tumor growth inhibitory activity of high specific activity from phenyl-Sepharose chromatography. Following chromatography by CM-Trisacryl® (modification procedure), only 20% of the total biologically active fraction could be subjected to one RPHPLC (C18), while generally 50% of the total biologically active, pooled fraction from phenyl Sepharose chromatography could be applied at one time to a C18 column. In these individual comparative experiments, the starting material for chromatography using CM TRISACRYL® was 9.9 mg and for phenyl-Sepharose was 42 mg, thus if the same amount of starting material was used for CM-TRISACRYL®, only 4.7% of the total preparation could have been utilized in the following C18 step. Because a greater amount of inhibitory activity could be applied to the C18 column, 100 times less sample (0.005 ml compared to 0.5 ml), was used to achieve the same degree of inhibitory activity. At this point in the procedure, the most biologically active fractions were resolved into six major protein bands by SDS-PAGE using silver stain.

Following HPLC on the C18 column, protein concentration could not be determined because the amount of available protein was below the resolution of standard techniques ($OD_{280}$ or Lowry). Thus, it was assumed that protein concentration was less than 20 micrograms/ml. To further purify TGI, the active fractions were pooled, lyophilized and applied to a RPHPLC CN column. Using a 2-propanol gradient of 0.6% increase in solvent per minute, the activity was shown to be displaced to the right of most of the protein (FIG. 16). Various active fractions were iodinated and separated by SDS-PAGE. The fractions demonstrating the most biological activity (FIG. 16, Fraction 59–65) illustrated in lane 2, contained two isotopically labeled bands, one of 25 kDa and one of 30 kDa and in lane 3 fractions 66–68 contained a homogeneous band at 25 kDa. Fraction #58 lane 7 is active but contains at least 5 bands. Fraction #56 which is the major peak of protein and is not biologically active contained all of the protein bands in fraction #58 except that 26 kDa band (FIG. 17, lane 1).

Three major conclusions can be deduced from the gel presented in FIG. 17. One, a 26 kDa protein is always present in fractions containing biologically active material and similarly it is always absent in fractions that are not biologically active. Two, the TGI demonstrates a similar qualitative activity to an ubiquitous protein derived from platelets and other tissues designated as TGF-$\beta$, in that it migrates by SDS-PAGE as a protein of $M_r$ 25 kDa as shown in FIG. 15B and FIG. 17. Three, the active fractions demonstrating the most biological activity in FIG. 17, lane 2, (2,068 units), does not compare intensity (iodinated protein) to the appearance of the 25 kDa band for TGF-β, observed in lane 7 containing 256 units of inhibitory activity. This implies a quantitative difference in specific activity.

The use of a stepwise gradient elution from the C18 column with acetonitrile resolved two peaks of activity, one eluting at 27% and one at 28–30% (FIGS. 14A & 14B). Following the combination of individual fractions into two separate pools, Pool I (27%) and Pool II (28–30%), from a column demonstrating a similar profile as shown in FIGS. 14A & 14B, the pools were applied to a RPHPLC CN column using a more shallow gradient than shown in FIG. 16 (0.37%/min. compared to 0.6%/min.). Pool I eluted at 40–41% 2-propanol (FIG. 18) and Pool II at 44% 2-propanol (FIG. 18). It is important to note that, as expected, the more hydrophobic protein eluting from the C18 column (Pool II) continued to elute more hydrophobically from the CN column. Thus, two distinct peaks of growth inhibitory activity have been obtained using the "alternate procedure" of protein purification. The first peak of activity, Pool I, contains 82% more inhibitory units than Pool II.

A purified protein, derived from platelets, designated as TGF-β, is biologically active in our inhibitory assay but consistently possesses 10–100 fold less activity than Pool I. Since activity in all cases, Pool I, Pool II, and TGF-β is consistent with presence of a protein band of $M_r$ 26 kDa (FIGS. 15 and 17), one can assume that all these proteins may be similar or belong to a family of growth inhibitory and/or growth modulating proteins. Alternatively, because of the differential elution of these proteins on both C18 and CN resins, and the greater specific activity of the TGIs, the TGIs may be entirely different than TGF-β (elevation of TGF-β profile not shown). Further biochemical characterization (amino acid sequencing) should resolve this question. In conclusion, it appears that the TGI's are better than (inhibitor activity) and different from (eluting position) TGF-β derived from platelets used for comparison by this study.

The conditioned media from A431 contained two types of growth inhibitory activity. One TGI elutes at approximately 25% acetonitrile and inhibits both A549 and CCl 64 mink cells. The selectivity of inhibition of this TGI is similar to what is observed for TGI-1 and TGI-2 in human umbilical cord extracts. The second TGI eluting between 30–36% acetonitrile shows a greater specificity for inhibiting A549 cells over mink cells.

Applicants presently contemplate a family of discrete entities which share certain common characteristics. Each family member is a polypeptide dimer, bound by disulfide bonds, with a molecular weight of 26,000 daltons which demonstrates tumor growth inhibitory activity against both a mink lung cell line (CCL 64) and a human carcinoma cell line (A549) in monolayer cultures.

The family comprises the novel discrete factors TGI-1 and TGI-2 and the previously disclosed factors TIF-1 and TGF-β. It is presently contemplated that TIF-1 and TGF-β are the same polypeptide which may be distinct from both TGI-1 and TGI-2. TGI-1 and TGI-2 being discrete cannot both be the same as TGF-β. TGI-1 and TGI-2 each have a specific activity greater than TGF-β. Both TGI-1 and TGI-2 elute differently from TGF-β on high pressure liquid chromatography on a CN column with 2-propanol. Further, TGI-1 and TGI-2 elute differently from each other on high pressure liquid chromatography on a CN column with 2-propanol.

Two separate factors CM-1 and a polypeptide derived from conditioned media of human tumor cell line (A549) are also disclosed. Because both have the property of substantially inhibiting the growth of a human tumor cell line (A549) but not of an established mink lung cell line (CCL 64) it is contemplated that CM-1 may be the same as the TGI derived from conditioned media from A431 cells. It is also contemplated that CM-1 may be similar to TIF-2 of an earlier patent.

Fourth Series of Experiments

Isolation and Sequence Determination of a Gene Encoding a Protein Having Tumor Growth Inhibitory Activity Cloning of TGF-β1

The sequence of TGF-β1 CDNA is published (Derynck, R., et al., Nature, 316, 701–705). Based on this sequence, we synthesized a 25 mer oligonucleotide probe (TGGTGTCCAGGGCTCGGCGGTGCCG) which was used to isolate a TGF-β1 CDNA from a commercial lambda-gtII human placenta library (Clonetech®). For these, and the following experiments, standard molecular biological techniques were employed (e.g., Maniatis, T., et al. (1982) Molecular Cloning, a laboratory manual, Cold Spring Harbor Lab). By restriction mapping and partial sequence analysis, the clone was shown to contain the complete coding sequence for the 390 amino acid TGF-β1 precursor but to lack some untranslated sequences from both the 5' and 3'0 ends (439 bp from the 5' end and approximately 200 bp from the 3' end).

Bacterial Expression of TGF-β1

Segments of the TGF-β1 gene were expressed in *E. coli* as trpE::TGF-β1 fusion proteins using two related inducible expression vectors: pATH II (Spindler et al. (1984) J. Virol. 49: 132–141) and pKS-1 (a pATH 11 derivative). The pATH 11::TGF-β1 construct was made by cloning a Bal I-Sal I fragment into the multiple cloning site of pATH 11. The Bal I-Sal I fragment encodes amino acid residues 249–391 of TGF-β1. The pKS-1::TGF-β1 construct was made by cloning a Nae I-Sal I fragment into the multiple cloning site of pKSl.

The Nae I-Sal I fragment encodes the TGF-β1 amino acid residues 25–391 (FIG. 23).

Bacteria (*E. coli* RRI) containing the expression plasmids were grown overnight into 1 ml M9 media (for 1 liter: 10 g $Na_2HPO_4$ & $H_2O$, 3 g $KH_2PO_4$, 0.5 g NaCl, 1 g $NH_4Cl$, 5 g casamino acids, 1 ml $MgSO_4$, 0.2 ml 0.5 M $CaCl_2$, 5 ml 40% glucose, 10 ml 1 mg/ml thiamine $B_1$) supplemented with 50 μg/ml ampicillin and 20 ng/ml tryptophan. A half ml of the overnight culture was diluted into 5 ml M9 media supplemented with ampicillin and grown for one hour at 30° C. with great aeration. The expression of the protein was induced by adding 12.5 μl of 2 mg/ml indole arcylic acid (IAA) and grown another 2 hours at 30° C. One ml was centrifuged (supernatant is the soluble fraction) and the pellet was resuspended in 100 μl TEN buffer (50 mM Tris-HCl pH 7.5, 0.5 mM EDTA, 0.3 M NaCl). Then subsequently were added:

10 μl 10 mg/ml lysozyme, 15 minutes on ice.

2 μl 10% NP-40, 10 minutes on ice.

150 μl 1.5 M9 NaCl, 12 mM $MgCl_2$ and 0.4 μl 1.9 mg/ml DNase, 1 hour on ice.

Then the insoluble fraction was collected by spinning 5 minutes in a microfuge. The pellet was washed twice with 100 μl TEN buffer and finally dissolved in 50 μl 0.01 M Na phosphate pH 7.2, 1% β-mercaptoethanol, 1% SDS, 6M urea and incubated 30 minutes at 37° C.

Following standard SDS-PAGE and Coomassie Blue staining, the constructed expression plasmids were found to produce fusion proteins with the predicted molecular weights (53 kd and 45 kd). Both proteins in a Western Blot (Towbin, et al. (1979) Proc Natl. Acad. Sci. 76: 4350–4354) reacted with a commercial (R and D Systems Inc.) polyclonal antisera against TGF-β1.

Cloning of the Gene Encoding the Protein Having Tumor Growth Inhibitory Activity To identify sequences with homology to TGF-β1 a Pvu II-Pvu II probe, containing most of the mature form of the TGF-β1 cDNA sequence, was 32P labelled and used to screen a Southern blot (Southern, (1975) J. Mol. Biol. 98: 503–517) of total human DNAs digested with Eco RI, Hind III or Sst I using standard methods. In each digest, two bands were present at a low stringency wash (2.5×SSC, 65° C.) (FIG. 24). When the wash stringency was increased (0.01× SSC, 65° C.) only one hybridizing band remained in each digest (FIG. 24). The strongly hybridizing band is likely TGF-β1 and the weakly hybridizing band is a related gene which also encodes a protein having tumor growth inhibitory activity. The nucleotide sequence encoding this protein having tumor growth inhibitory activity and its amino acid sequence are shown in FIG. 29.

To isolate the gene encoding the protein having tumor growth inhibitory activity with homology to TGF-β1 the Pvu II-Pvu II probe from the TGF-β1 clone was used to screen a human phage library constructed from the DNA of a chronic myelocytic leukemia cell line (K562). Two genomic loci, which correspond to TGF-β1 and the related gene encoding a protein having tumor growth inhibitory activity (FIG. 29), were cloned and the pUC subclones of phages were mapped by restriction enzyme analysis (FIG. 25 and 26). Construction of the K562 library, screening and isolation of recombinant clones was carried out essentially according to the procedures of Grosveld, et al. (1981) Gene 13: 227–237.

The phage DNA clone containing the sequence encoding the protein related to TGF-β1 and with tumor growth inhibitory activity was cut with Sau 3A and the restriction fragments cloned into M13. The recombinant plaques were screened with the Sma I-Pvu II probe of TGF-β1. Six hybridizing genomic clones were sequenced by the method of Sanger, et al. (1977) Proc. Natl. Acad. Sci. 74: 5463–5467, and a region of approximately 130 bp was found to be homologous to TGF-β1 cDNA (FIG. 27). When the amino acid sequence of TGF-β1 and the related gene cloned in these experiments were compared they were found to be 82% homologous.

To obtain a repeat free probe of the TGF-β1 gene encoding the protein having tumor growth inhibitory activity, various restriction fragments from Bam HI-Bam HI subclone of this gene were hybridized to TGF-β1 cDNA, as well as to total human DNA. A BamHI-TaqI fragment of the gene encoding the protein having tumor growth inhibitory activity was found to hybridize specifically to the TGF-β1 cDNA. The position of this fragment in the gene encoding the protein having tumor growth inhibitory activity is shown in FIG. 28.

The Bam HI-Taq I unique probe of the sequence encoding the protein having tumor growth inhibitory activity was used to screen the lambda-gtII human placenta CDNA library (Clonetech®). Two strongly hybridizing clones, as well as four weakly hybridizing clones, were isolated. By DNA sequence analysis the weakly hybridizing clones were shown to correspond to the TGF-β1 (FIG. 31). One strongly hybridizing clone was isolated and a 1.7 kb EcoRI insert was subcloned into pUC 8. The restriction map of this clone is shown in FIG. 30.

Restriction fragments for this clone were subcloned into M13 and sequenced by the method of Sanger, et al. The deduced amino acid sequence of this gene exhibits extensive homology with a family of genes (Massague, J. (1987) Cell 49, 437–438) including TGF-β1, TGF-β2, glioblastoma T-cell supressor factor (G-TsF) factor, inhibin/activin, Mullerian Inhibitive Substance (MIS) and decapentaplegic transcript complex of Drosophila with the six cysteine residues being conserved throughout. The comparison with TGF-β1 and TGF-β2 is shown in FIG. 31. The cDNA sequence (FIG. 29) encoding the protein having tumor growth inhibitory activity corresponded with the sequence from genomic DNA (FIG. 27) encoding the protein having tumor growth inhibitory activity.

A 17 kb genomic DNA fragment containing the sequence of the gene encoding the protein having tumor growth inhibitory activity has been cloned (see FIG. 26). Hybridizing 5' and 3' portions of the 1.7 kb CDNA clone which encodes the protein having tumor growth inhibitory activity with the genomic locus of the protein having tumor growth inhibitory activity revealed that the 1.7 kb cDNA sequence is completely contained in the genomic clone. Taking into account that the full length message of the protein having tumor growth inhibitory activity is 3.5 kb, additional 5' and 3' flanking sequences may be isolated to obtain the complete gene. This is done by screening genomic phage and cosmid libraries with probes unique to the gene encoding the protein having tumor growth inhibitory activity.

In TGF-β1 the sequence R-R (as indicated at position −1 and −2 in FIG. 31) represents the proteolytic cleavage site which generates the mature protein. In the related protein having tumor growth inhibitory activity, the sequence R-K-K-R likely represents the corresponding cleavage site.

In the region N terminal to the predicted cleavage site, TGF-β1 and the related gene encoding the protein having tumor growth inhibitory activity exhibit only 7% homology. Both proteins, however, contain the sequence R-G-D-L in this region which is likely recognized by the fibronectin receptor.

In order to determine which cell line types express the related gene encoding the protein having tumor growth inhibitory activity, Northern hybridization was carried out using a 5' terminal Eco RI-Bgl II probe (FIG. 32). This revealed a mRNA of approximately 3.5 kb in A673 (a rhabdomyosarcoma), A498 (a kidney carcinoma) and a faintly hybridizing signal in A549 (a lung adenocarcinoma).

A genomic probe from the 3' region of the related gene encoding the protein having tumor growth inhibitory activity (corresponding to downstream of the presumed site of proteolytic cleavage) was then used to screen the same Northern blot. Three strong hybridization signals were observed in both A673 and A498, corresponding to TGF-β1 (2.5 kb), the related protein having tumor growth inhibitory activity (3.5 kb) and, another related gene (4.2 kb) (FIG. 33). These results are consistent with the fact that this probe would be predicted to cross react with sequences homologous to the protein having tumor growth inhibitory activity.

Northern blot analysis of A673, A549 and A498 cell lines using a Pst I-Bal I TGF-β1 probe was then performed. This probe should be highly specific for TGF-β1 since it contains sequences corresponding to those N terminal to the proteolytic cleavage site, a region where TGF-β1 exhibits little homology to other members of this gene family. As predicted, based on the known 2.5 kb size of TGF-β1 mRNA, a strong hybridization to a 2.5 kb mRNA band was observed in all three cell lines. Several weakly hybridizing bands are also observed at 4.2 kb and 3.5. kb (FIG. 34).

Northern blot analysis of A673, A549 and A498 cell lines were then screened using TGF-β1 cDNA containing the complete coding sequence of the TGF-β1 precursor. This probe is predicted to cross hybridize with homologous sequences to TGFβ1. As predicted, there was strong hybridization to a 2.5 kb mRNA band corresponding to TGF-β1 and a 4.2 kb mRNA band possibly corresponding to TGF-β2 (FIG. 35).

Northern blot analysis of mRNA from human umbilical cord-and A673 cell line were also screened using an Eco RI-Bgl II cDNA fragment of the related gene encoding the protein having tumor growth inhibitory activity as a probe (FIG. 36). The figure includes the result with a actin probe acting as a control to normal mRNA levels in each lane. Normalized to actin mRNA levels, the cord expresses the highest level of mRNA of the gene encoding the protein having tumor growth inhibitory activity of any cell type so far examined (FIG. 36).

Southern blot analysis was performed on a variety of different tumor DNAs digested with Eco RI and hybridized with a Sma I-Ava I CDNA fragment of the TGF-β1 related gene encoding the protein having tumor growth inhibitory activity as a probe at low (2.5×SSC, 65° C.) and high (0.3×SSC, 65° C.) stringency washes. Southern blot indicates the possible presence of other loci related to the gene encoding the protein having tumor growth inhibitory activity, as the probe hybridizes with two bands (3 kb and 12 kb) which are only observed under conditions of washing at low stringency.

To obtain a full length cDNA clone of the gene encoding the potein having tumor growth inhibitory activity, a blot of the Okayama-Berg cDNA library from human fibroblasts was screened with the 5' Eco RI-Bgl II probe of the 1.7 kb cDNA clone of the gene encoding the protein having tumor growth inhibitory activity. A hybridizing band of 3.2 kb is visible at moderate wash stringency 0.3×SSC, 65° C.

Production of Antibodies with Specificity for the TQF-β1 Related Protein Having Tumor Growth Inhibitory Activity Chimeric bacterial proteins have been constructed that contain the C terminal 150 amino acids of the protein having tumor growth inhibitory activity fused to a small region of the trpE gene. Such a fusion protein was found to be recognized by an antibody that was produced against a peptide derived from amino acid numbers 9 to 28 of the mature form of the protein having tumor growth inhibitory activity. The antibody recognizes the trp::protein having tumor growth inhibitory activity fusion protein to a much higher degree than a trp::TGF-β fusion protein and the peptide specifically competes with the protein having tumor growth inhibitory activity for the binding of the anti-body.

DNA sequences that code for TGF-β1 related protein having tumor growth inhibitory activity were cloned into a pKS vector. This vector is a pATH II derivative that contains the inducible trp promoter and a multiple cloning site. The resulting constructs produce a chimeric protein consisting of the first 22 amino acids of the trpE gene, the C terminal 150 amino acids of the protein having tumor growth inhibitory activity. Transformants containing these clones were screened primarily by restriction endonuclease analysis and ultimately for production of the chimeric protein by SDS polyacrylamide gel electrophoresis. The protein products of 3 clones, p116, p134, and p135, are shown in FIG. 37. These cells were grown in defined media until they reached early log phase and then incubated for 3 hours either in the presence or absence of the trpE inducer indoleacrylic acid (IAA). The cells were then collected, lysed and their proteins electrophoresed on a 12.5% SDS polyacrylamide gel. FIG. 37 is a photograph of one such gel that had been stained with Coomassie blue. As can be seen, lysates pll6 and p135 produce a protein of about 19,000 Dalton molecular weight whose relative abundance increases in the presence of IAA. In contrast, pl34 does not produce this protein species. Both pll6 and pl35 contain plasmids that, by restriction analysis, have the sequences of the protein having tumor growth inhibitory activity cloned in the orientation that should produce a 19,500 Dalton molecular weight fusion protein. The p134 plasmid was found to have the sequences of the protein having tumor growth inhibitory activity in the opposite orientation.

The trpE::protein having tumor growth inhibitory activity fusion protein was used to test the specificity of an antibody that used a peptide homologous to part of the protein having tumor growth inhibitory activity as an antigen. A polypeptide was synthesized corresponding to residues 9 through 28 of the mature protein having tumor growth inhibitory activity, except that residue 9 in the sequence, arginine, was replaced by serine. The peptide was purified by RPHPLC, and coupled to keyhole limpet hemocyanin for use as an immunogen in rabbits.

Thirty-three days following the first injection (500 μg) the antisera were screened by standard ELISA using 100 ng of peptide per well. One rabbit demonstrated a signal of 1.0 OD units at a 1:25 dilution of the antibody. Ten days after this rabbit was first bled, a boost of 250 mg of coupled antigen was given. The following bleed 20 days after the first bleed showed a 20-fold increase in antibody response to the peptide antigen. Forty days after the initial bleed (3rd bleed) a signal of 1.0 OD unit was achieved at a 1:8000 dilution of the antisera, a 16-fold increase in antibody titer over the second bleed. This antibody also showed little cross-reactivity with a homologous peptide derived from TGF-β1 sequences. The TGF-β1 derived peptide consisted of amino acid numbers 4 to 19 of the mature TGF-β1 protein. Of the 11 common amino acids, residues 9–19, 7 are conserved between the protein having tumor growth inhibitory activity and TGF-β1.

To determine if the peptide recognizing antibody could recognize the protein having tumor growth inhibitory activity, the antibody was used in Western blot analysis against a fusion protein of the protein having tumor growth inhibitory activity and a TGF-β1 fusion. As seen in FIG. 38, the anti-peptide antibody reacted strongly with the fusion protein of the protein having tumor growth inhibitory activity while it reacted only weakly with a trp::TGF-β1 fusion protein. Both fusion proteins were recognized by a commercially available anti-TGF-β1 antibody (R and D systems) (FIG. 38).

As can be seen in FIG. 38, the anti-peptide antibody recognizing the protein having tumor growth inhibitory activity also has a high level of background reactivity to bacterial proteins. To reduce this cross reactivity, we purified the antibody on a CNBr-Sepharose column containing the original peptide used as an antigen. The antibody retained its high titer to the peptide of the protein having tumor growth inhibitory activity and low cross reactivity to the homologous peptide TGF-β1 (data not shown). The purified peptide antibody was then tested by Western blot analysis for its cross-reactivity with TGF-β1. The results are shown in FIG. 39. The purified antibody reacts very strongly with the fusion protein of the protein having tumor growth inhibitory activity (lane 2)and with a higher molecular weight protein species, while the hybridization to other bacterial proteins was found to be greatly reduced compared to the unpurified antibody (FIG. 38). The purified antibody exhibits negligible reactivity with either the TGF-β1 fusion protein (lane 1) or purified, TGF-β1 obtained commercially (R and D systems) (lanes 3 and 6). A competition experiment was also performed where the purified antibody was preincubated with a 300 fold molar excess of the peptide (lanes 4, 5 and 6). Preincubation of the antibody with excess peptide for 60 minutes at room temperature considerably reduced hybridization to the fusion protein of the protein having tumor growth inhibitory activity (lane 5) but not to trace background reactivity exhibited against the TGF-β1 fusion protein or to other bacterial proteins (lane 4). Thus the antipeptide antibody specifically recognizes proteins containing sequences of the protein having tumor growth inhibitory activity.

Eucaryotic Expression of TGF-β1 Fused with the Protein Having Tumor Growth Inhibitory Activity Human recombinant TGF-β1 has been expressed in monkey COS cells. Sequences encoding the complete precursor of the TGF-β1 cDNA were cloned down stream from a SV40 promoter using the pSVL® eukaryotic expression vector (obtained from Pharmacia). This construct was transfected into COS cells using a standard calcium phosphate precipitation method, Graham and van der Eb (1973) Virology 52, 456–467. After transfection, approximately 4×10⁶ cells were grown in serum free media for two days. The conditioned media was then collected, acidified and tested for biological activity. Conditioned media from TGF-β1 transfected cells was found to inhibit the growth of a monolayer mink lung test cell line (CCL 64) by 59% as compared to conditioned media from COS cells transfected with the pSVL vector alone which inhibited growth of CCL 64 cells by only 32%.

Since a full length clone for the sequences encoding the protein having tumor growth inhibitory activity is not currently available for expression analysis, a chimeric TGF-β1::protein having tumor growth inhibitory activity fusion construct was made by substituting 3' sequences of the TGF-β1 precursor with sequences encoding the protein having tumor growth inhibitory activity. Given the homology between these two proteins and the conserved position of their cysteine residues, when such a construct is transfected into Cos cells the novel fusion protein may be processed into the biologically active mature protein having tumor growth inhibitory activity. Additional constructs, which consist of the trp E::gene encoding the protein having tumor growth inhibitory activity fusion cloned under the regulatory sequences of either the SV40 promoter or the long terminal repeat of the mouse mammary tumor virus (MMTV) have been made and may be tested for biological activity in transient transfection experiments.

CONCLUSION FROM THE FOURTH SERIES OF EXPERIMENTS

In the Fourth Series of Experiments TGF-β1 was cloned and used to isolate a related gene encoding a protein having tumor growth inhibitory activity. Although it has not yet been determined which of TGI-1 or TGI-2 corresponds to the protein related to TGF-β1 and having tumor growth inhibitory activity, one skilled in the art would understand that such a correspondence exists although the exact nature of this corresponding remains to be clarified.

What is claimed is:

1. An isolated nucleic acid comprising a nucleic acid encoding a polypeptide of 112 amino acids having the amino acid sequence shown in FIGS. 29A–29B beginning with alanine at position 1 and ending with serine at position 112.

2. An isolated nucleic acid having a nucleotide sequence identical to the nucleotide sequence of the 1.7 kilobase Eco RI insert contained within the plasmid deposited under ATCC Designation No. 40939.

3. A recombinant nucleic acid vector comprising a nucleic acid encoding a polypeptide of 112 amino acids having the amino acid sequence shown in FIGS. 29A–29B beginning with alanine at position 1 and ending with serine position 112.

4. The recombinant nucleic acid vector of claim 3, wherein the vector comprises DNA having the sequence shown in FIGS. 29A–29B beginning with the guanine of the GCT codon corresponding to alanine at position 1 and ending with the cytosine of the AGC codon corresponding to serine at position 112.

5. A recombinant nucleic acid vector consisting of a nucleic acid having the nucleic acid sequence shown in FIGS. 29A–29B beginning with the guanine of the GCT codon corresponding to alanine at position 1 and ending with the cytosine of the AGC codon corresponding to serine at position 112 and a vector nucleic acid.

6. A recombinant nucleic acid vector of claim 3 or 5, wherein the vector is a plasmid.

7. A host cell transformed with the recombinant vector of claim 3 or 5.

8. A method for producing a protein comprising culturing the host cell of claim 7, under conditions suitable to express the protein in the host cell and recovering the protein so expressed.

9. A bacterial host cell of claim 7.

10. A method for producing a protein comprising culturing the host cell of claim 9 under conditions suitable to express the protein in the host cell and recovering the protein so expressed.

11. A eucaryotic host cell of claim 7.

12. A method for producing a protein comprising culturing the host cell of claim 11, under conditions suitable to express the protein in the host cell and recovering the protein so expressed.

13. An isolated nucleic acid sequence comprising a nucleic acid encoding a protein comprising a heterologous polypeptide sequence fused to a polypeptide of 112 amino acids comprising the amino acid sequence shown in FIGS. 29A–29B beginning with alanine at position 1 and ending with serine at position 112.

14. A recombinant nucleic acid vector comprising nucleic acid encoding a heterologous polypeptide sequence fused to a polypeptide of 112 amino acids comprising the amino acid sequence shown in FIGS. 29A–29B beginning with alanine at position 1 and ending with serine at position 112.

15. The recombinant nucleic acid vector of claim 14, wherein the nucleic acid polypeptide of 112 amino acids comprises a DNA having the sequence shown in FIGS. 29A–29B beginning with the guanine of the GCT codon corresponding to alanine at position 1.

16. The recombinant nucleic acid vector of claim 14, wherein the vector is a plasmid.

17. The recombinant nucleic acid vector of claim 15, wherein the vector is a plasmid.

18. A host cell transformed with the recombinant nucleic acid vector of claim 14.

19. A host cell transformed with the recombinant nucleic acid vector of claim 15.

20. A method of producing a protein comprising culturing the host cell of claim 18, under conditions suitable to express the protein in the host cell and recovering the protein so expressed.

21. A method of producing a protein comprising culturing the host cell of claim 19, under conditions suitable to express the protein in the host cell and recovering the protein so expressed.

* * * * *